US010590384B2

(12) United States Patent
Choi et al.

(10) Patent No.: US 10,590,384 B2
(45) Date of Patent: Mar. 17, 2020

(54) LUTERIAL AND METHOD FOR ISOLATING AND CULTURING THE SAME

(71) Applicant: LUTERION CO., LTD., Gyeonggi-do (KR)

(72) Inventors: Won Cheol Choi, Gyeonggi-do (KR); Young Ah Kwon, Seoul (KR); Suk Hoon Choi, Seoul (KR); Chang Hoon Choi, Seoul (KR)

(73) Assignee: LUTERION CO., LTD., Gyeonggi-Do (KR)

( * ) Notice: Subject to any disclaimer, the term of this patent is extended or adjusted under 35 U.S.C. 154(b) by 56 days.

(21) Appl. No.: 15/633,283

(22) Filed: Jun. 26, 2017

(65) Prior Publication Data

US 2018/0051252 A1    Feb. 22, 2018

Related U.S. Application Data

(63) Continuation-in-part of application No. 15/109,114, filed as application No. PCT/KR2014/004197 on May 9, 2014.

(30) Foreign Application Priority Data

Jan. 14, 2014  (KR) ........................ 10-2014-0004525

(51) Int. Cl.
| G01N 33/48 | (2006.01) |
| C12N 5/078 | (2010.01) |
| C12N 5/076 | (2010.01) |
| A61K 35/14 | (2015.01) |
| C12N 13/00 | (2006.01) |
| A61K 35/52 | (2015.01) |
| A61K 35/38 | (2015.01) |
| A61K 35/28 | (2015.01) |
| A61K 35/20 | (2006.01) |
| G06G 7/58 | (2006.01) |

(52) U.S. Cl.
CPC ............ *C12N 5/0634* (2013.01); *A61K 35/14* (2013.01); *A61K 35/20* (2013.01); *A61K 35/28* (2013.01); *A61K 35/38* (2013.01); *A61K 35/52* (2013.01); *C12N 5/061* (2013.01); *C12N 13/00* (2013.01); *C12N 2529/00* (2013.01)

(58) Field of Classification Search
None
See application file for complete search history.

(56) References Cited

U.S. PATENT DOCUMENTS 9,128,101 B2    9/2015  Halbert et al.
2013/0203081 A1  8/2013  Rak et al.

2013/0337440 A1  12/2013  Antes et al.
2014/0162888 A1   6/2014  Kuslich et al.
2016/0324896 A1  11/2016  Choi et al.

FOREIGN PATENT DOCUMENTS

| EP | 3021119 A1 | 5/2016 |
| EP | 3096141 A1 | 11/2016 |
| JP | 05034338 B2 | 5/1993 |
| JP | 05034339 B2 | 5/1993 |
| JP | 2008-505104 A | 2/2008 |
| JP | 2016-526688 A | 9/2016 |
| KR | 100663888 | 12/2006 |
| KR | 10-2013-0056855 A | 5/2013 |
| WO | 2009100029 A1 | 8/2009 |
| WO | 2011127219 A1 | 10/2011 |
| WO | 2013122950 A1 | 8/2013 |
| WO | 2015005553 A1 | 1/2015 |

OTHER PUBLICATIONS

Barry, O., et al., "Mechanisms of Cellular Activation by Platelet Microparticles", "Thrombosis and Haemostasis", Aug. 1999, pp. 794-800, vol. 82.
Barry, O., et al., "Arachidonic Acid in Platelet Microparticles Up-Regulates Cyclooxygenase-2-Dependent Prostaglandin Formation Via a Protein Kinase C/Mitogen-Activated Protein Kinase-Dependent Pathway", "The Journal of Biological Chemistry", Mar. 12, 1999, pp. 7545-7556, vol. 274, No. 11.
Lee, Y., et al., "Exosomes and Microvesicles: Extracellular Vesicles for Genetic Information Transfer and Gene Therapy", "Human Molecular Genetics", Aug. 7, 2012, p. R125-R134, vol. 21, No. 1.
Loke, K., et al., "Potential Role of eNOS in the Therapeutic Control of Myocardial Oxygen Consumption by Ace Inhibitors and Amlodipine", "Cardiovascular Research", 2001, pp. 86-93, vol. 49, No. 1.
Morales-Ruiz, M., et al., "Sphingosine 1-Phosphate Activates AKT, Nitric Oxide Production, and Chemotaxis Through a Gi Protein/Phosphoinositide 3-Kinase Pathway in Endothelial Cells", "The Journal of Biological Chemistry", Jun. 1, 2001, pp. 19672-19677, vol. 276, No. 22.
Seeger, H., Blutuntersuchung im Dunkelfeld und ihre Glaubwurdigkeit, URL:https://www.dunkelfeld-blutdiagnostik.de/cms/NS_Blutuntersuchung-im-Dunkelfeld-G laubwuerdigkeit.html, Nov. 11, 2007.
Seeger, H., Blutuntersuchung im Dunkelfeld und ihre Glaubwurdigkeit, URL:https://www.dunkelfeld-blutdiagnostik.de/cms/NS_Blutuntersuchung-im-Dunkelfeld-G laubwuerdigkeit.html, Nov. 11, 2007, Page(s) Machine Translation.

*Primary Examiner* — Eric S Dejong
(74) *Attorney, Agent, or Firm* — Hultquist, PLLC; Steven J. Hultquist

(57) ABSTRACT

The present disclosure relates to luterial, which is a mitochondrial-like unidentified nano-sized particle derived from a body fluid, and to a method for isolating the same.

10 Claims, 51 Drawing Sheets
(47 of 51 Drawing Sheet(s) Filed in Color)
Specification includes a Sequence Listing.

Rhodamine 123 Positive by Zeiss LSM-780

Real Time Recording(CCD) Mito-tracker Positive

FIG. 8
Life Cycling A
Normal (Fission)
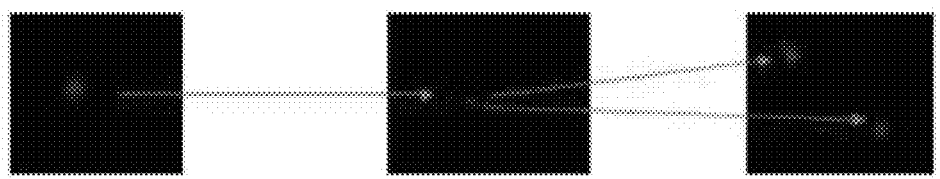
Life Cycling B
Abnormal (Fusion or Coagulation)
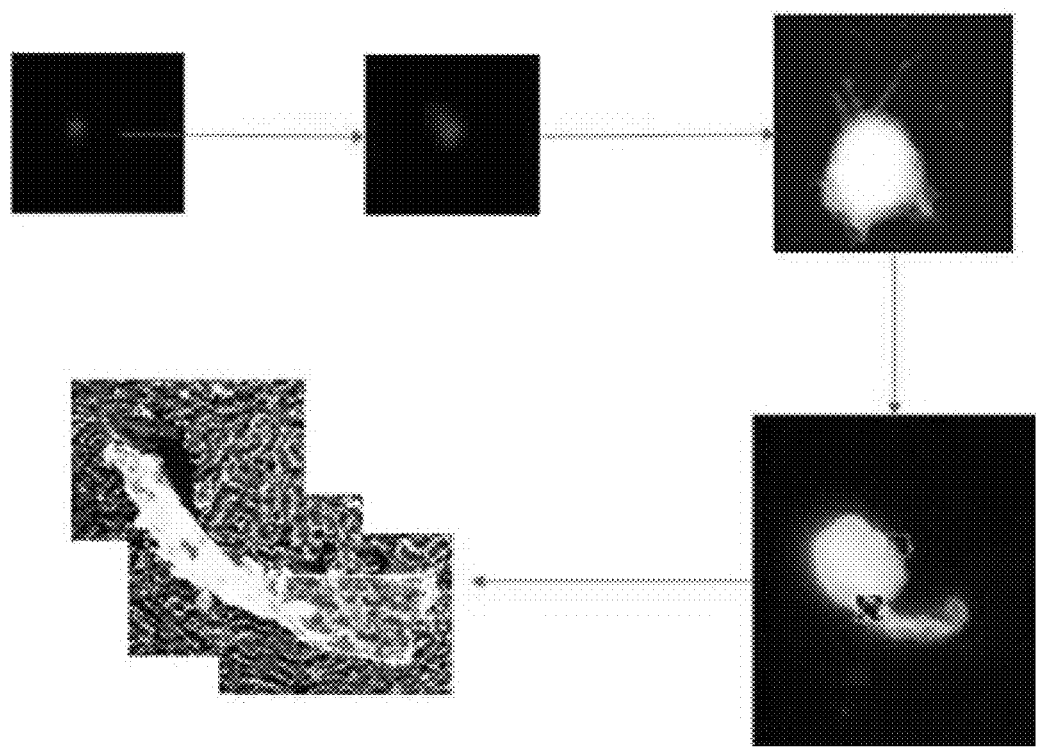

FIG. 10A
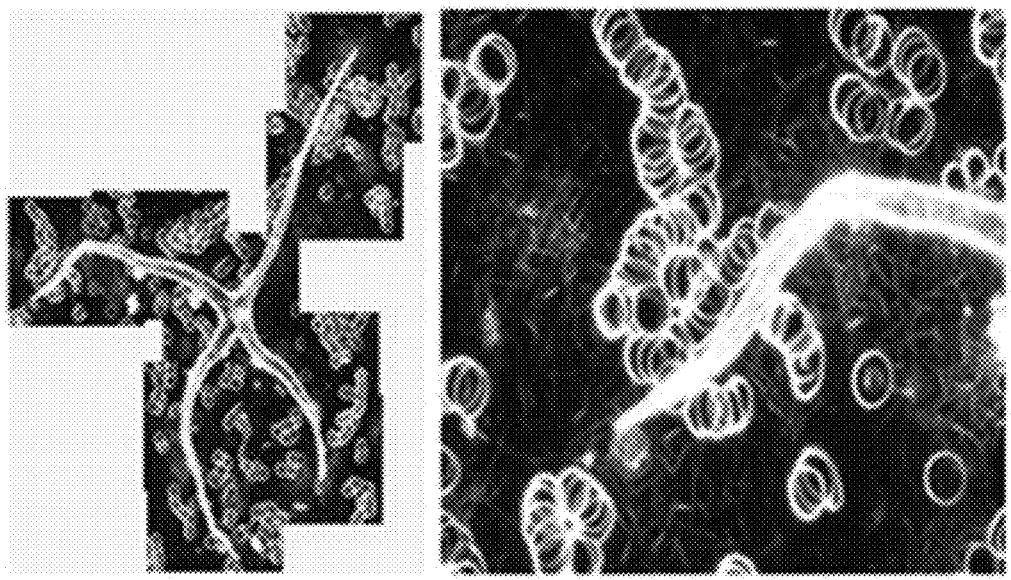
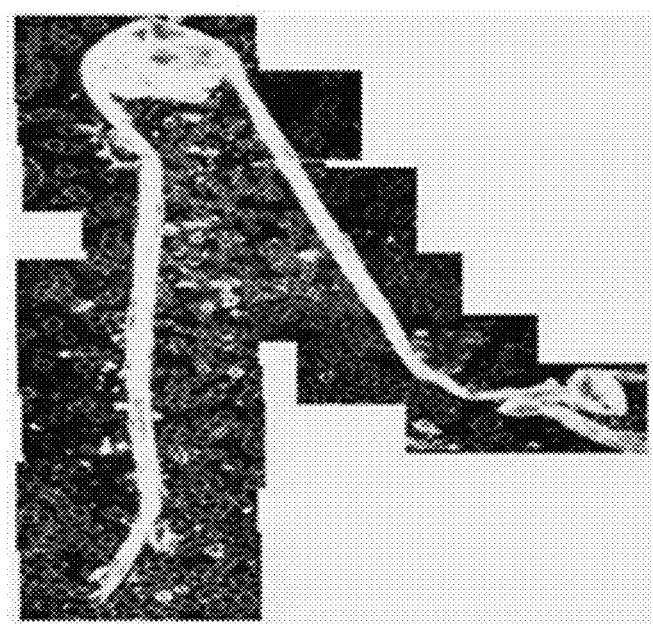

DAPI / Mitotracker Red / Rhodamine123 Positive
(TCS-SP Leica)

FIG. 13
Rhodamine + DAPI staining
Transmission optical image 100x
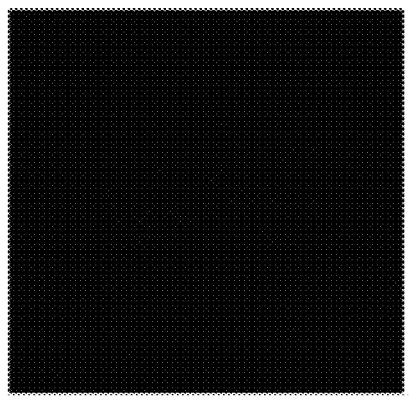
Fluorescence optical image 100x
Rhodamine stained
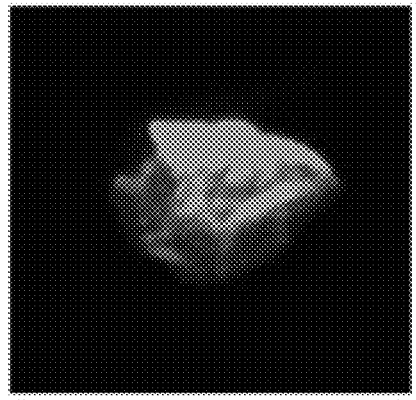
Fluorescence optical image 100x
DAPI stained
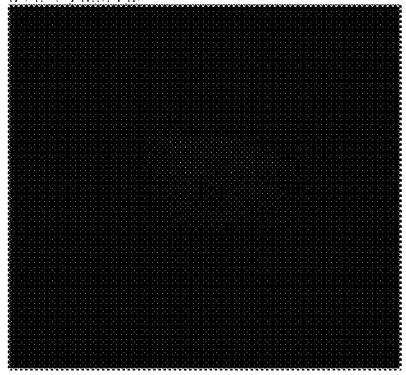
Fluorescence optical image with scratch
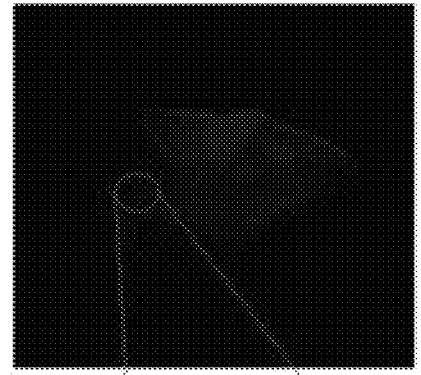
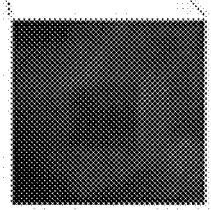
Magnification of the scratch.
It can be seen that the button of
the scratch is still DAPI positive.

FIG. 15
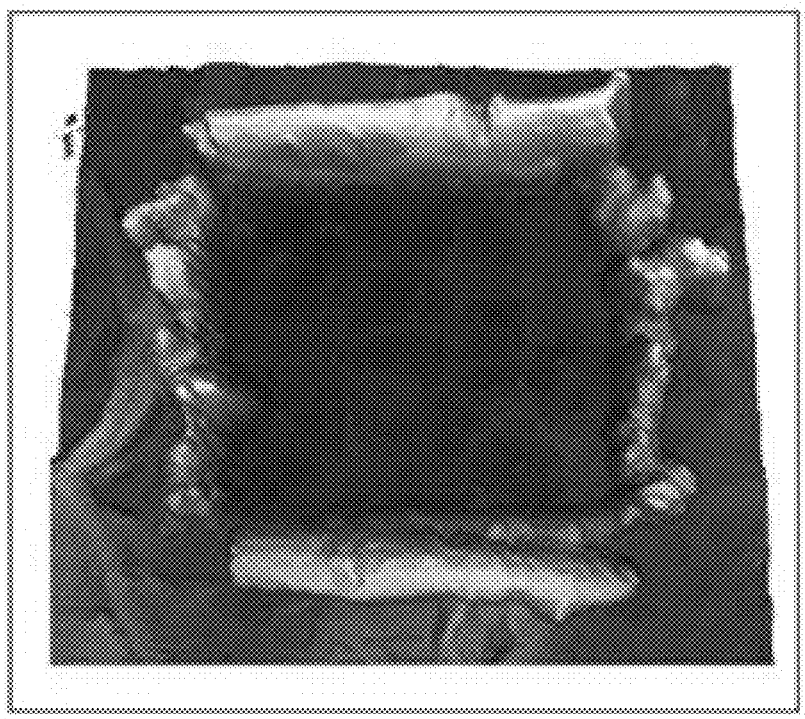
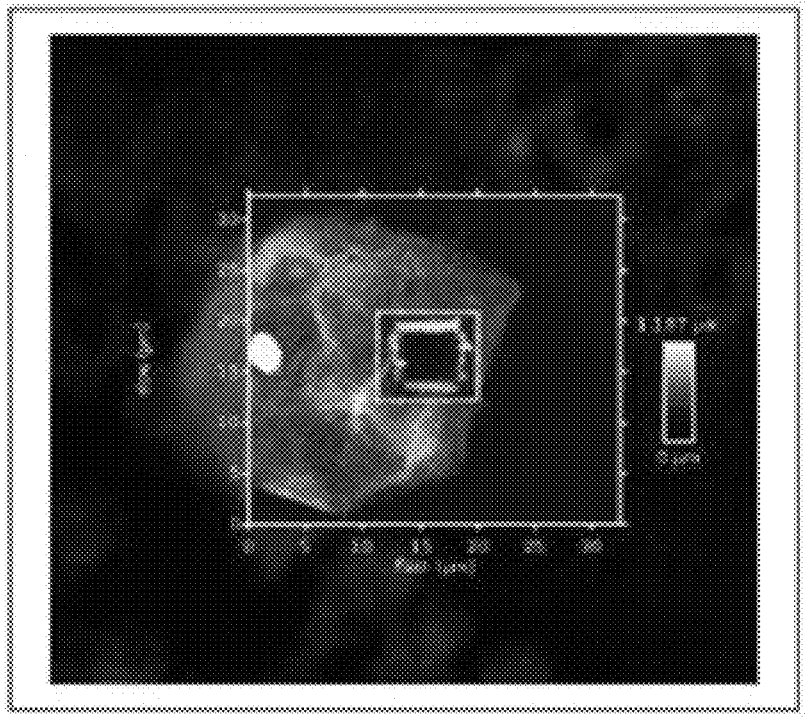

| | Sample Name | Conc. (Nanodrop) (ng/ul) | 260/280 | Volume (ul) | Total amount (ng) | QC Result |
|---|---|---|---|---|---|---|
| 1 | L(Luterial)KN-B (PCRpurification) | 12.389 | 1.806 | 23 | 284.947 | pass |

DNA Isolation,
performed by Jun
in Boston, 2013
(<100~1200nm)

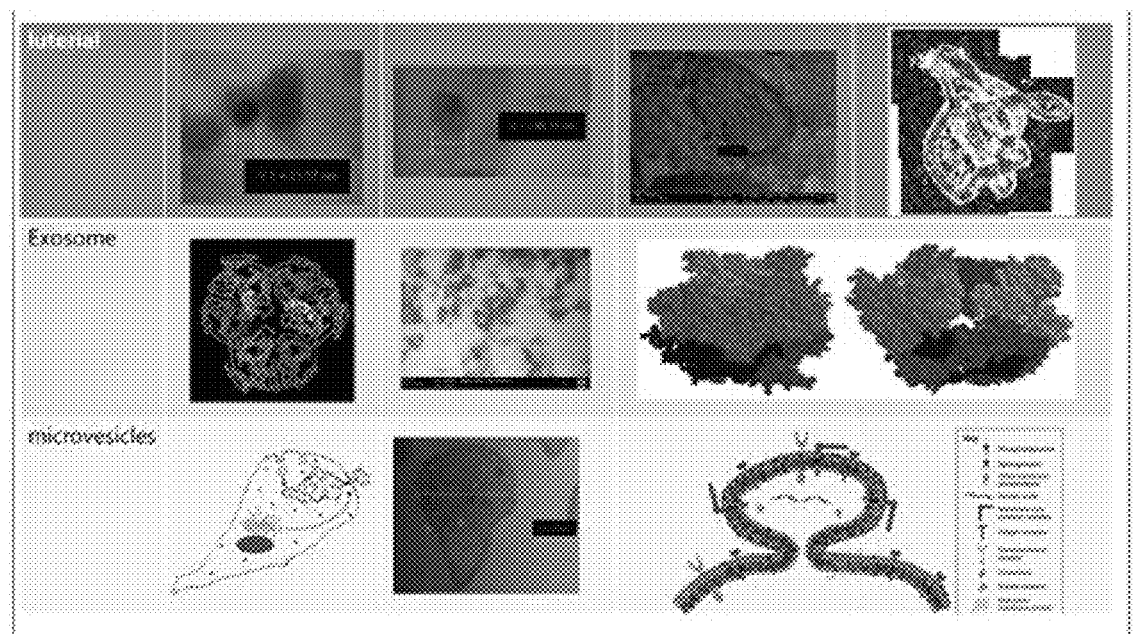

DKU20140414 Fr#2

Phylum
- Proteobacteria(99.87%)
- Firmicutes(0.02%)
- Bacteroidetes(0.07%)
- Streptophyta(0.02%)
- Fusobacteria(0.02%)

Family
- Halomonadaceae(99.79%)
- Ralstonia_f(0.03%)
- Moraxellaceae(0.01%)
- Burkholderiaceae(0.02%)
- Sphaerotilus_f(0.01%)
- Staphylococcaceae(0.01%)
- Streptococcaceae(0.01%)
- Chitinophagaceae(0.05%)
- Prevotellaceae(0.02%)
- ETC(0.06%)

FIG. 25A
DKU20140313DNA
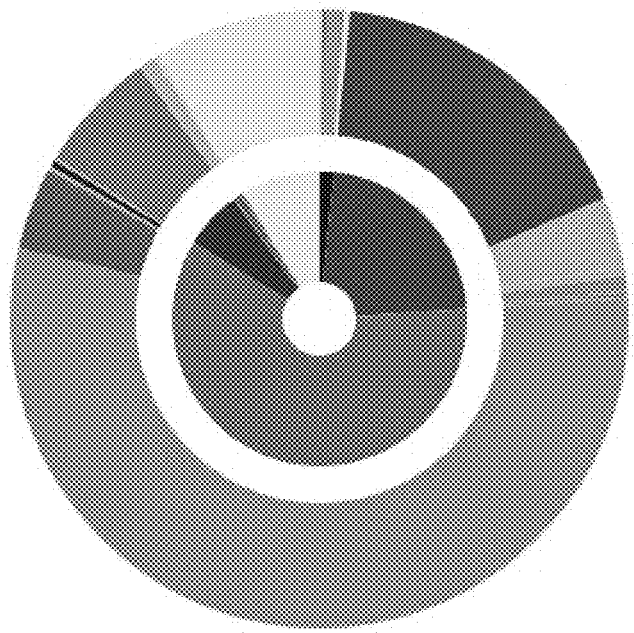
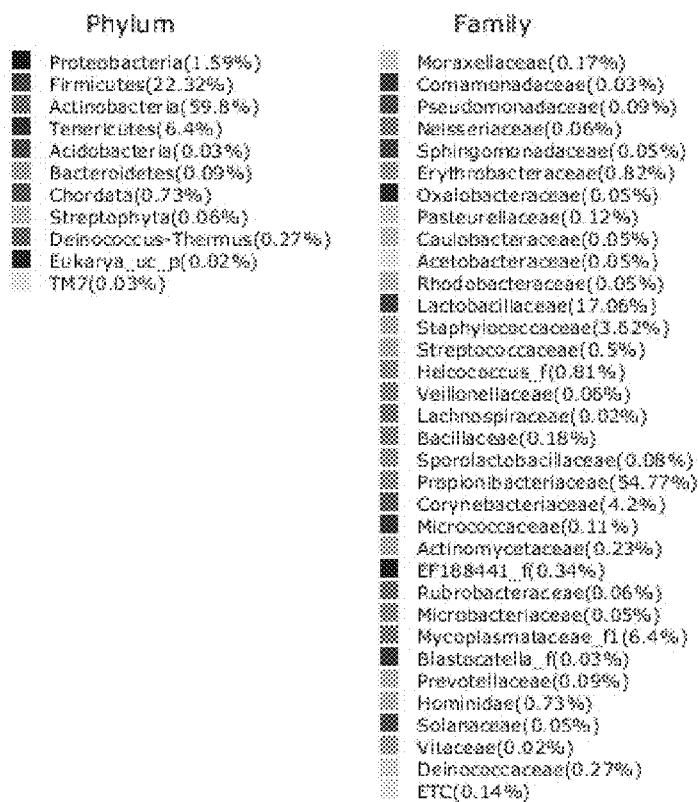

SEQUENCE LISTING

```
<160> NUMBER OF SEQ ID NOS: 28

<210> SEQ ID NO 1
<211> LENGTH: 51
<212> TYPE: DNA
<213> ORGANISM: Artificial Sequence
<220> FEATURE:
<223> OTHER INFORMATION: Primer, B16S-F

<400> SEQUENCE: 1
cctatcccct gtgtgccttg gcagtctcag acgagtttga tcmtggctca g          51

<210> SEQ ID NO 2
<211> LENGTH: 51
<212> TYPE: DNA
<213> ORGANISM: Artificial Sequence
<220> FEATURE:
<223> OTHER INFORMATION: Primer, Bif16S-F

<400> SEQUENCE: 2
cctatcccct gtgtgccttg gcagtctcag acgggttcga ttctggctca g          51

<210> SEQ ID NO 3
<211> LENGTH: 56
<212> TYPE: DNA
<213> ORGANISM: Artificial Sequence
<220> FEATURE:
<223> OTHER INFORMATION: Primer, B16-7-4

<400> SEQUENCE: 3
ccatctcatc cctgcgtgtc tccgactcag agagctgacw ttaccgcggc tgctgg     56

<210> SEQ ID NO 4
<211> LENGTH: 56
```

```
<212> TYPE: DNA
<213> ORGANISM: Artificial Sequence
<220> FEATURE:
<223> OTHER INFORMATION: Primer, B16-7-7

<400> SEQUENCE: 4
ccatctcatc cctgcgtgtc tccgactcag tcagatgacw ttaccgcggc tgctgg      56

<210> SEQ ID NO 5
<211> LENGTH: 56
<212> TYPE: DNA
<213> ORGANISM: Artificial Sequence
<220> FEATURE:
<223> OTHER INFORMATION: Primer, B16-7-8

<400> SEQUENCE: 5
ccatctcatc cctgcgtgtc tccgactcag cgatgagacw ttaccgcggc tgctgg      56

<210> SEQ ID NO 6
<211> LENGTH: 56
<212> TYPE: DNA
<213> ORGANISM: Artificial Sequence
<220> FEATURE:
<223> OTHER INFORMATION: Primer, B16-7-12

<400> SEQUENCE: 6
ccatctcatc cctgcgtgtc tccgactcag tctgcagacw ttaccgcggc tgctgg      56

<210> SEQ ID NO 7
<211> LENGTH: 56
<212> TYPE: DNA
<213> ORGANISM: Artificial Sequence
<220> FEATURE:
<223> OTHER INFORMATION: Primer, B16-7-13

<400> SEQUENCE: 7
ccatctcatc cctgcgtgtc tccgactcag agcgatgacw ttaccgcggc tgctgg      56

<210> SEQ ID NO 8
<211> LENGTH: 57
<212> TYPE: DNA
<213> ORGANISM: Artificial Sequence
<220> FEATURE:
<223> OTHER INFORMATION: Primer, B16-8-3

<400> SEQUENCE: 8
ccatctcatc cctgcgtgtc tccgactcag atgctgagac wttaccgcgg ctgctgg     57

<210> SEQ ID NO 9
<211> LENGTH: 57
<212> TYPE: DNA
<213> ORGANISM: Artificial Sequence
<220> FEATURE:
<223> OTHER INFORMATION: Primer, B16-8-4

<400> SEQUENCE: 9
ccatctcatc cctgcgtgtc tccgactcag tacagcagac wttaccgcgg ctgctgg     57

<210> SEQ ID NO 10
<211> LENGTH: 57
<212> TYPE: DNA
<213> ORGANISM: Artificial Sequence
<220> FEATURE:
<223> OTHER INFORMATION: Primer, B16-8-18

<400> SEQUENCE: 10
```
ccatctcatc cctgcgtgtc tccgactcag atcgtgtgac wttaccgcgg ctgctgg    57

<210> SEQ ID NO 11
<211> LENGTH: 57
<212> TYPE: DNA
<213> ORGANISM: Artificial Sequence
<220> FEATURE:
<223> OTHER INFORMATION: Primer, B16-8-21

<400> SEQUENCE: 11
ccatctcatc cctgcgtgtc tccgactcag ctacacagac wttaccgcgg ctgctgg    57

<210> SEQ ID NO 12
<211> LENGTH: 58
<212> TYPE: DNA
<213> ORGANISM: Artificial Sequence
<220> FEATURE:
<223> OTHER INFORMATION: Primer, B16-9-4

<400> SEQUENCE: 12
ccatctcatc cctgcgtgtc tccgactcag cgtgtactga cwttaccgcg gctgctgg   58

<210> SEQ ID NO 13
<211> LENGTH: 58
<212> TYPE: DNA
<213> ORGANISM: Artificial Sequence
<220> FEATURE:
<223> OTHER INFORMATION: Primer, B16-9-5

<400> SEQUENCE: 13
ccatctcatc cctgcgtgtc tccgactcag ctgtctacga cwttaccgcg gctgctgg   58

<210> SEQ ID NO 14
<211> LENGTH: 58
<212> TYPE: DNA
<213> ORGANISM: Artificial Sequence
<220> FEATURE:
<223> OTHER INFORMATION: Primer, B16-9-8

<400> SEQUENCE: 14
ccatctcatc cctgcgtgtc tccgactcag agtcactaga cwttaccgcg gctgctgg   58

<210> SEQ ID NO 15
<211> LENGTH: 58
<212> TYPE: DNA
<213> ORGANISM: Artificial Sequence
<220> FEATURE:
<223> OTHER INFORMATION: Primer, B16-9-12

<400> SEQUENCE: 15
ccatctcatc cctgcgtgtc tccgactcag agctcactga cwttaccgcg gctgctgg   58

<210> SEQ ID NO 16
<211> LENGTH: 59
<212> TYPE: DNA
<213> ORGANISM: Artificial Sequence
<220> FEATURE:
<223> OTHER INFORMATION: Primer, B16-10-6

<400> SEQUENCE: 16
ccatctcatc cctgcgtgtc tccgactcag atcacgtgcg acwttaccgc ggctgctgg  59

<210> SEQ ID NO 17
<211> LENGTH: 59
<212> TYPE: DNA
<213> ORGANISM: Artificial Sequence

```
<220> FEATURE:
<223> OTHER INFORMATION: Primer, B16-10-7

<400> SEQUENCE: 17
ccatctcatc cctgcgtgtc tccgactcag atagctctcg acwttaccgc ggctgctgg      59

<210> SEQ ID NO 18
<211> LENGTH: 59
<212> TYPE: DNA
<213> ORGANISM: Artificial Sequence
<220> FEATURE:
<223> OTHER INFORMATION: Primer, B16-10-8

<400> SEQUENCE: 18
ccatctcatc cctgcgtgtc tccgactcag agtgagctcg acwttaccgc ggctgctgg      59

<210> SEQ ID NO 19
<211> LENGTH: 59
<212> TYPE: DNA
<213> ORGANISM: Artificial Sequence
<220> FEATURE:
<223> OTHER INFORMATION: Primer, B16-10-9

<400> SEQUENCE: 19
ccatctcatc cctgcgtgtc tccgactcag agtctgactg acwttaccgc ggctgctgg      59

<210> SEQ ID NO 20
<211> LENGTH: 60
<212> TYPE: DNA
<213> ORGANISM: Artificial Sequence
<220> FEATURE:
<223> OTHER INFORMATION: Primer, B16-11-1

<400> SEQUENCE: 20
ccatctcatc cctgcgtgtc tccgactcag tcatatacgc gacwttaccg cggctgctgg     60

<210> SEQ ID NO 21
<211> LENGTH: 60
<212> TYPE: DNA
<213> ORGANISM: Artificial Sequence
<220> FEATURE:
<223> OTHER INFORMATION: Primer, B16-11-2

<400> SEQUENCE: 21
ccatctcatc cctgcgtgtc tccgactcag tagatagtgc gacwttaccg cggctgctgg     60

<210> SEQ ID NO 22
<211> LENGTH: 60
<212> TYPE: DNA
<213> ORGANISM: Artificial Sequence
<220> FEATURE:
<223> OTHER INFORMATION: Primer, B16-11-3

<400> SEQUENCE: 22
ccatctcatc cctgcgtgtc tccgactcag acgtctctac gacwttaccg cggctgctgg     60

<210> SEQ ID NO 23
<211> LENGTH: 60
<212> TYPE: DNA
<213> ORGANISM: Artificial Sequence
<220> FEATURE:
<223> OTHER INFORMATION: Primer, B16-11-4

<400> SEQUENCE: 23
ccatctcatc cctgcgtgtc tccgactcag ctagagacac tacwttaccg cggctgctgg     60
```

<210> SEQ ID NO 24
<211> LENGTH: 16569
<212> TYPE: DNA
<213> ORGANISM: Unknown
<220> FEATURE:
<223> OTHER INFORMATION: Luterial genome sequence
<220> FEATURE:
<221> NAME/KEY: misc_feature
<222> LOCATION: (3107)..(3107)
<223> OTHER INFORMATION: n is a, c, g, or t

<400> SEQUENCE: 24

| | | | | | |
|---|---|---|---|---|---|
| gatcacaggt | ctatcaccct | attaaccact | cacgggagct | ctccatgcat | ttggtatttt | 60 |
| cgtctggggg | gtatgcacgc | gatagcattg | cgagacgctg | gagccggagc | accctatgtc | 120 |
| gcagtatctg | tctttgattc | ctgcctcatt | ctattattta | tcgcacctac | gttcaatatt | 180 |
| acgggcgaac | atacttacta | aagtgtgtta | attaattaat | gcttgtagga | cataataata | 240 |
| acaattgaat | gtctgcacag | ccactttcca | cacagacatc | ataacaaaaa | atttccacca | 300 |
| aaccccccct | cccccgcttc | tggccacagc | acttaaacac | atctctgcca | aaccccaaaa | 360 |
| acaaagaacc | ctaacaccag | cctaaccaga | tttcaaattt | tatcttttgg | cggtatgcac | 420 |
| ttttaacagt | caccccccaa | ctaacacatt | attttcccct | cccactccca | tactactaat | 480 |
| ctcatcaata | caaccccgc | ccatcctacc | cagcacacac | acaccgctgc | taacccccata | 540 |
| ccccgaacca | accaaacccc | aaagacaccc | ccacagtttt | atgtagctta | cctcctcaaa | 600 |
| gcaatacact | gaaaatgttt | agacgggctc | acatcacccc | ataaacaaat | aggtttggtc | 660 |
| ctagcctttc | tattagctct | tagtaagatt | acacatgcaa | gcatcccgt | tccagtgagt | 720 |
| tcaccctcta | aatcaccacg | atcaaaagga | acaagcatca | agcacgcagc | aatgcagctc | 780 |
| aaaacgctta | gcctagccac | accccacgg | gaaacagcag | tgattaacct | ttagcaataa | 840 |
| acgaaagttt | aactaagcta | tactaacccc | agggttggtc | aatttcgtgc | cagccaccgc | 900 |
| ggtcacacga | ttaacccaag | tcaatagaag | ccggcgtaaa | gagtgtttta | gatcaccccc | 960 |
| tccccaataa | agctaaaact | cacctgagtt | gtaaaaaact | ccagttgaca | caaaatagac | 1020 |
| tacgaaagtg | gctttaacat | atctgaacac | acaatagcta | agacccaaac | tgggattaga | 1080 |
| taccccacta | tgcttagccc | taaacctcaa | cagttaaatc | aacaaaactg | ctcgccagaa | 1140 |
| cactacgagc | cacagcttaa | aactcaaagg | acctggcggt | gcttcatatc | cctctagagg | 1200 |
| agcctgttct | gtaatcgata | aaccccgatc | aacctcacca | cctcttgctc | agcctatata | 1260 |
| ccgccatctt | cagcaaaccc | tgatgaaggc | tacaaagtaa | gcgcaagtac | ccacgtaaag | 1320 |
| acgttaggtc | aaggtgtagc | ccatgaggtg | gcaagaaatg | ggctacattt | tctaccccag | 1380 |
| aaaactacga | tagcccttat | gaaacttaag | ggtcgaaggt | ggatttagca | gtaaactaag | 1440 |
| agtagagtgc | ttagttgaac | agggccctga | agcgcgtaca | caccgcccgt | caccctcctc | 1500 |
| aagtatactt | caaaggacat | ttaactaaaa | cccctacgca | tttatataga | ggagacaagt | 1560 |
| cgtaacatgg | taagtgtact | ggaaagtgca | cttggacgaa | ccagagtgta | gcttaacaca | 1620 |
| aagcacccaa | cttacactta | ggagatttca | acttaacttg | accgctctga | gctaaaccta | 1680 |
| gccccaaacc | cactccacct | tactaccaga | caaccttagc | caaaccattt | acccaaataa | 1740 |
| agtataggcg | atagaaattg | aaacctggcg | caatagatat | agtaccgcaa | gggaaagatg | 1800 |
| aaaaattata | accaagcata | atatagcaag | gactaacccc | tataccttct | gcataatgaa | 1860 |
| ttaactagaa | ataactttgc | aaggagagcc | aaagctaaga | cccccgaaac | cagacgagct | 1920 |
| acctaagaac | agctaaaaga | gcacacccgt | ctatgtagca | aaatagtggg | aagatttata | 1980 |

```
ggtagaggcg acaaacctac cgagcctggt gatagctggt tgtccaagat agaatcttag    2040
ttcaacttta aatttgccca cagaaccctc taaatcccct tgtaaattta actgttagtc    2100
caaagaggaa cagctctttg gacactagga aaaaaccttg tagagagagt aaaaaattta    2160
acacccatag taggcctaaa agcagccacc aattaagaaa gcgttcaagc tcaacaccca    2220
ctacctaaaa aatcccaaac atataactga actcctcaca cccaattgga ccaatctatc    2280
accctataga agaactaatg ttagtataag taacatgaaa acattctcct ccgcataagc    2340
ctgcgtcaga ttaaaacact gaactgacaa ttaacagccc aatatctaca atcaaccaac    2400
aagtcattat taccctcact gtcaacccaa cacaggcatg ctcataagga aaggttaaaa    2460
aaagtaaaag gaactcggca atcttaccc cgcctgttta ccaaaaacat cacctctagc    2520
atcaccagta ttagaggcac cgcctgccca gtgacacatg tttaacggcc gcggtaccct    2580
aaccgtgcaa aggtagcata atcacttgtt ccttaaatag ggacctgtat gaatggctcc    2640
acgagggttc agctgtctct tactttaac cagtgaaatt gacctgcccg tgaagaggcg    2700
ggcataacac agcaagacga gaagacccta tggagcttta atttattaat gcaaacagta    2760
cctaacaaac ccacaggtcc taaactacca aacctgcatt aaaaatttcg gttggggcga    2820
cctcggagca gaacccaacc tccgagcagt acatgctaag acttcaccag tcaaagcgaa    2880
ctactatact caattgatcc aataacttga ccaacggaac aagttaccct agggataaca    2940
gcgcaatcct attctagagt ccatatcaac aatagggttt acgacctcga tgttggatca    3000
ggacatcccg atggtgcagc cgctattaaa ggttcgtttg ttcaacgatt aaagtcctac    3060
gtgatctgag ttcagaccgg agtaatccag gtcggtttct atctacnttc aaattcctcc    3120
ctgtacgaaa ggacaagaga aataaggcct acttcacaaa gcgccttccc ccgtaaatga    3180
tatcatctca acttagtatt atacccacac ccacccaaga cagggtttg ttaagatggc    3240 agagcccggt aatcgcataa aacttaaaac tttacagtca gaggttcaat tcctcttctt    3300
aacaacatac ccatggccaa cctcctactc ctcattgtac ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aacccgccac atctaccatc accctctaca tcaccgcccc gaccttagct    3540
ctcaccatcg ctcttctact atgaaccccc ctccccatac caacccct ggtcaacctc    3600 aacctaggcc tcctatttat tctagccacc tctagcctag ccgtttactc aatcctctga    3660
tcagggtgag catcaaactc aaactacgcc ctgatcggcg cactgcgagc agtagcccaa    3720
acaatctcat atgaagtcac cctagccatc attctactat caacattact aataagtggc    3780
tcctttaacc tctccaccct tatcacaaca caagaacacc tctgattact cctgccatca    3840
tgacccttgg ccataatatg atttatctcc acactagcag agaccaaccg aaccccttc    3900 gaccttgccg aaggggagtc cgaactagtc tcaggcttca acatcgaata cgccgcaggc    3960
cccttcgccc tattcttcat agccgaatac acaaacatta ttataataaa caccctcacc    4020
actacaatct tcctaggaac aacatatgac gcactctccc ctgaactcta cacaacatat    4080
tttgtcacca agaccctact tctaacctcc ctgttcttat gaattcgaac agcataccc    4140 cgattccgct acgaccaact catacacctc ctatgaaaaa acttcctacc actcacccta    4200
gcattactta tatgatatgt ctccataccc attacaatct ccagcattcc ccctcaaacc    4260
taagaaatat gtctgataaa agagttactt tgatagagta aataatagga gcttaaaccc    4320
```

```
ccttatttct aggactatga gaatcgaacc catccctgag aatccaaaat tctccgtgcc    4380
acctatcaca ccccatccta aagtaaggtc agctaaataa gctatcgggc ccatacccccg   4440 aaaatgttgg ttatacccctt cccgtactaa ttaatcccct ggcccaaccc gtcatctact   4500
ctaccatctt tgcaggcaca ctcatcacag cgctaagctc gcactgattt tttacctgag    4560
taggcctaga aataaacatg ctagctttta ttccagttct aaccaaaaaa ataaaccctc    4620
gttccacaga agctgccatc aagtatttcc tcacgcaagc aaccgcatcc ataatccttc    4680
taatagctat cctcttcaac aatatactct ccggacaatg aaccataacc aatactacca   4740
atcaatactc atcattaata atcataatag ctatagcaat aaaactagga atggcccccct   4800 ttcacttctg agtcccagag gttacccaag gcaccccttct gacatccggc ctgcttcttc   4860
tcacatgaca aaaactagcc cccatctcaa tcatatacca aatctctccc tcactaaacg    4920
taagccttct cctcactctc tcaatcttat ccatcatagc aggcagttga ggtggattaa    4980
accaaaccca gctacgcaaa atcttagcat actcctcaat tacccacata ggatgaataa    5040
tagcagttct accgtacaac cctaacataa ccattcttaa tttaactatt tatattatcc    5100
taactaccac cgcattccta ctactcaact aaaactccag caccacgacc ctactactat    5160
ctcgcacctg aaacaagcta acatgactaa caccccttaat tccatccacc ctcctctccc    5220
taggaggcct gccccccgcta accggctttt tgcccaaatg ggccattatc gaagaattca    5280
caaaaaacaa tagcctcatc atccccacca tcatagccac catcaccctc cttaacctct    5340
acttctacct acgcctaatc tactccacct caatcacact actccccata tctaacaacg    5400
taaaaataaa atgacagttt gaacatacaa aaccccacccc attcctcccc acactcatcg   5460
cccttaccac gctactccta cctatctccc cttttatact aataatctta tagaaattta    5520
ggttaaatac agaccaagag ccttcaaagc cctcagtaag ttgcaatact taatttctgt    5580
aacagctaag gactgcaaaa ccccactctg catcaactga acgcaaatca gccactttaa    5640
ttaagctaag cccttactag accaatggga cttaaaccca caaacactta gttaacagct    5700
aagcacccta atcaactggc ttcaatctac ttctcccgcc gccgggaaaa aaggcgggag    5760
aagccccggc aggtttgaag ctgcttcttc gaatttgcaa ttcaatatga aaatcacctc    5820
ggagctggta aaaagaggcc taaccccctgt ctttagattt acagtccaat gcttcactca    5880
gccattttac ctcaccccca ctgatgttcg ccgaccgttg actattctct acaaaccaca    5940
aagacattgg aacactatac ctattattcg gcgcatgagc tggagtccta ggcacagctc    6000
taagcctcct tattcgagcc gagctgggcc agcaggcaa ccttctaggt aacgaccaca    6060
tctacaacgt tatcgtcaca gcccatgcat ttgtaataat cttcttcata gtaatacccca   6120 tcataatcgg aggctttggc aactgactag ttcccctaat aatcggtgcc cccgatatgg    6180
cgtttccccg cataaacaac ataagcttct gactcttacc tccctctctc ctactcctgc    6240
tcgcatctgc tatagtggag gccggagcag gaacaggttg aacagtctac cctcccttag    6300
cagggaacta ctcccacccct ggagcctccg tagacctaac catcttctcc ttacacctag    6360
caggtgtctc ctctatctta ggggccatca atttcatcac aacaattatc aatataaaac    6420
cccctgccat aacccaatac caaacgcccc tcttcgtctg atccgtccta atcacagcag    6480
tcctacttct cctatctctc ccagtcctag ctgctggcat cactatacta ctaacagacc    6540
gcaacctcaa caccaccttc ttcgaccccg ccggaggagg agaccccatt ctataccaac    6600
acctattctg atttttcggt cacccctgaag tttatattct tatcctacca ggcttcggaa    6660
taatctccca tattgtaact tactactccg gaaaaaaaga accatttgga tacataggta    6720
```

-continued

```
tggtctgagc tatgatatca attggcttcc tagggtttat cgtgtgagca caccatatat    6780
ttacagtagg aatagacgta gacacacgag catatttcac ctccgctacc ataatcatcg    6840
ctatccccac cggcgtcaaa gtatttagct gactcgccac actccacgga agcaatatga    6900
aatgatctgc tgcagtgctc tgagcccrag gattcatctt tcttttcacc gtaggtggcc    6960
tgactggcat tgtattagca aactcatcac tagacatcgt actacacgac acgtactacg    7020
ttgtagccca cttccactat gtcctatcaa taggagctgt atttgccatc ataggaggct    7080
tcattcactg atttccccta ttctcaggct acaccctaga ccaaacctac gccaaaatcc    7140
atttcactat catattcatc ggcgtaaatc taactttctt cccacaacac tttctcggcc    7200
tatccggaat gccccgacgt tactcggact accccgatgc atacaccaca tgaaacatcc    7260
tatcatctgt aggctcattc atttctctaa cagcagtaat attaataatt ttcatgattt    7320
gagaagcctt cgcttcgaag cgaaaagtcc taatagtaga agaaccctcc ataaacctgg    7380
agtgactata tggatgcccc ccaccctacc acacattcga agaacccgta tacataaaat    7440
ctagacaaaa aaggaaggaa tcgaaccccc caaagctggt ttcaagccaa ccccatggcc    7500
tccatgactt tttcaaaaag gtattagaaa accatttcta tactttgtc aaagttaaat    7560
tataggctaa atcctatata tcttaatggc acatgcagcg caagtaggtc tacaagacgc    7620
tacttcccct atcatagaag agcttatcac ctttcatgat cacgccctca taatcatttt    7680
ccttatctgc ttcctagtcc tgtatgccct tttcctaaca ctcacaacaa aactaactaa    7740
tactaacatc tcagacgctc aggaaataga aaccgtctga actatcctgc ccgccatcat    7800
cctagtcctc atcgccctcc catccctacg catcctttac ataacagacg aggtcaacga    7860
tccctctctt accatcaaat caattggcca ccaatggtac tgaacctacg agtacaccga    7920
ctacggcgga ctaatcttca actcctacat acttccccca ttattcctag aaccaggcga    7980
cctgcgactc cttgacgttg acaatcgagt agtactcccg attgaagccc ccattcgtat    8040
aataattaca tcacaagacg tcttgcactc atgagctgtc cccacattag cttaaaaac    8100
agatgcaatt cccggacgtc taaaccaaac cactttcacc gctacacgac cggggggtata    8160
ctacggtcaa tgctctgaaa tctgtggagc aaaccacagc ttcatgccca tcgtcctaga    8220
attaattccc ctaaaaatct ttgaaatagg gcccgtattt accctatagc accccctcta    8280
ccccctctag agcccactgt aaagctaact tagcattaac cttttaagtt aaagattaag    8340
agaaccaaca cctctttaca gtgaaatgcc ccaactaaat actaccgtat ggcccaccat    8400
aattacccc atactcctta cactattcct catcacccaa ctaaaaatat aaacacaaa    8460
ctaccaccta cctccctcac caaagcccat aaaaataaaa aattataaca aaccctgaga    8520
accaaaatga cgaaaatct gttcgcttca ttcattgccc ccacaatcct aggcctaccc    8580
gccgcagtac tgatcattct atttcccccct ctattgatcc ccacctccaa atatctcatc    8640
aacaaccgac taatcaccac ccaacaatga ctaatcaaac taacctcaaa acaaatgata    8700
gccatacaca acactaaagg acgaacctga tctcttatac tagtatccctt aatcattttt    8760
attgccacaa ctaacctcct cggactcctg cctcactcat ttacaccaac cacccaacta    8820
tctataaacc tagccatggc catccccta tgagcgggca cagtgattat aggctttcgc    8880
tctaagatta aaaatgccct agcccacttc ttaccacaag gcacacctac accccttatc    8940
cccatactag ttattatcga aaccatcagc ctactcattc aaccaatagc cctggccgta    9000
cgcctaaccg ctaacattac tgcaggccac ctactcatgc acctaattgg aagcgccacc    9060
```

```
ctagcaatat caaccattaa ccttccctct acacttatca tcttcacaat tctaattcta   9120
ctgactatcc tagaaatcgc tgtcgcctta atccaagcct acgttttcac acttctagta   9180
agcctctacc tgcacgacaa cacataatga cccaccaatc acatgcctat catatagtaa   9240
aacccagccc atgaccccta cagggcccc tctcagccct cctaatgacc tccggcctag    9300
ccatgtgatt tcacttccac tccataacgc tcctcatact aggcctacta accaacacac   9360
taaccatata ccaatgatgg cgcgatgtaa cacgagaaag cacataccaa ggccaccaca   9420
caccacctgt ccaaaaaggc cttcgatacg ggataatcct atttattacc tcagaagttt   9480 tttttcttcgc aggattttc tgagcctttt accactccag cctagcccct acccccccaat  9540 taggagggca ctggccccca acaggcatca ccccgctaaa tcccctagaa gtcccactcc   9600
taaacacatc cgtattactc gcatcaggag tatcaatcac ctgagctcac catagtctaa   9660
tagaaaacaa ccgaaaccaa ataattcaag cactgcttat tacaatttta ctgggtctct   9720 attttacccct cctacaagcc tcagagtact tcgagtctcc cttcaccatt tccgacggca   9780
tctacggctc aacatttttt gtagccacag gcttccacgg acttcacgtc attattggct   9840
caactttcct cactatctgc ttcatccgcc aactaatatt tcactttaca tccaaacatc   9900
actttggctt cgaagccgcc gcctgatact ggcattttgt agatgtggtt tgactatttc   9960
tgtatgtctc catctattga tgagggtctt actcttttag tataaatagt accgttaact  10020
tccaattaac tagttttgac aacattcaaa aaagagtaat aaacttcgcc ttaatttaa   10080 taatcaacac cctcctagcc ttactactaa taattattac attttgacta ccacaactca  10140
acggctacat agaaaaatcc acccttacg agtgcggctt cgaccctata tcccccgccc   10200
gcgtcccttt ctccataaaa ttcttcttag tagctattac cttcttatta tttgatctag  10260
aaattgccct ccttttaccc ctaccatgag ccctacaaac aactaacctg ccactaatag  10320
ttatgtcatc cctcttatta atcatcatcc tagccctaag tctggcctat gagtgactac  10380
aaaaaggatt agactgaacc gaattggtat atagtttaaa caaaacgaat gatttcgact  10440
cattaaatta tgataatcat atttaccaaa tgcccctcat ttacataaat attatactag  10500
catttaccat ctcacttcta ggaatactag tatatcgctc acacctcata tcctccctac  10560
tatgcctaga aggaataata ctatcgctgt tcattatagc tactctcata accctcaaca  10620
cccactccct cttagccaat attgtgccta ttgccatact agtctttgcc gcctgcgaag  10680
cagcggtggg cctagcccta ctagtctcaa tctccaacac atatggccta gactacgtac  10740
ataacctaaa cctactccaa tgctaaaact aatcgtccca acaattatat tactaccact  10800
gacatgactt tccaaaaaac acataaatttg aatcaacaca accacccaca gcctaattat  10860
tagcatcatc cctctactat ttttaaccaa atcaacaac aacctattta gctgttcccc  10920 aacctttttcc tccgacccc taacaacccc cctcctaata ctaactacct gactcctacc  10980
cctcacaatc atggcaagcc aacgccactt atccagtgaa ccactatcac gaaaaaaact  11040
ctacctctct atactaatct ccctacaaat ctccttaatt ataacattca cagccacaga  11100
actaatcata ttttatatct tcttcgaaac cacacttatc cccaccttgg ctatcatcac  11160
ccgatgaggc aaccagccag aacgcctgaa cgcaggcaca tacttcctat tctacaccct  11220
agtaggctcc cttcccctac tcatcgcact aatttacact cacaacaccc taggctcact  11280
aaacattcta ctactcactc tcactgccca agaactatca aactcctgag ccaacaactt  11340
aatatgacta gcttacacaa tagcttttat agtaaagata cctctttacg gactccactt  11400
atgactccct aaagcccatg tcgaagcccc catcgctggg tcaatagtac ttgccgcagt  11460
```

```
actcttaaaa ctaggcggct atggtataat acgcctcaca ctcattctca acccctgac   11520 aaaacacata gcctacccct tccttgtact atccctatga ggcataatta taacaagctc   11580
catctgccta cgacaaacag acctaaaatc gctcattgca tactcttcaa tcagccacat   11640
agccctcgta gtaacagcca ttctcatcca aaccccctga agcttcaccg gcgcagtcat   11700
tctcataatc gcccacgggc ttacatcctc attactattc tgcctagcaa actcaaacta   11760
cgaacgcact cacagtcgca tcataatcct ctctcaagga cttcaaactc tactcccact   11820
aatagctttt tgatgacttc tagcaagcct cgctaacctc gccttacccc ccactattaa   11880
cctactggga gaactctctg tgctagtaac cacattctcc tgatcaaata tcactctcct   11940
acttacagga ctcaacatac tagtcacagc cctatactcc ctctacatat ttaccacaac   12000 acaatgggc tcactcaccc accacattaa caacataaaa ccctcattca cacgagaaaa   12060
caccctcatg ttcatacacc tatcccccat tctcctccta tccctcaacc ccgacatcat   12120
taccgggttt tcctcttgta atatagtttt aaccaaaaca tcagattgtg aatctgacaa   12180
cagaggctta cgaccccta tttaccgaga aagctcacaa gaactgctaa ctcatgcccc   12240
catgtctaac aacatggctt tctcaacttt taaaggataa cagctatcca ttggtcttag   12300
gccccaaaaa ttttggtgca actccaaata aaagtaataa ccatgcacac tactataacc   12360
accctaaccc tgacttccct aattccccc atccttacca ccctcgttaa ccctaacaaa   12420
aaaaactcat accccatta tgtaaaatcc attgtcgcat ccacctttat tatcagtctc   12480
ttccccacaa caatattcat gtgcctagac caagaagtta ttatctcgaa ctgacactga   12540
gccacaaccc aaacaaccca gctctcccta agcttcaaac tagactactt ctccataata   12600
ttcatccctg tagcattgtt cgttacatgg tccatcatag aattctcact gtgatatata   12660
aactcagacc caaacattaa tcagttcttc aaatatctac tcatcttcct aattaccata   12720
ctaatcttag ttaccgctaa caacctattc caactgttca tcggctgaga gggcgtagga   12780
attatatcct tcttgctcat cagttgatga tacgcccgag cagatgccaa cacagcagcc   12840
attcaagcaa tcctatacaa ccgtatcggc gatatcggtt tcatcctcgc cttagcatga   12900
tttatcctac actccaactc atgagaccca caacaaatag cccttctaaa cgctaatcca   12960
agcctcaccc cactactagg cctcctccta gcagcagcag gcaaatcagc ccaattaggt   13020
ctccacccct gactccctc agccatagaa ggccccaccc cagtctcagc cctactccac   13080
tcaagcacta tagttgtagc aggaatcttc ttactcatcc gcttccaccc cctagcagaa   13140
aatagcccac taatccaaac tctaacacta tgcttaggcg ctatcaccac tctgttcgca   13200
gcagtctgcg cccttacaca aaatgacatc aaaaaaatcg tagccttctc cacttcaagt   13260
caactaggac tcataatagt tacaatcggc atcaaccaac cacacctagc attcctgcac   13320
atctgtaccc acgccttctt caaagccata ctatttatgt gctccgggtc catcatccac   13380
aaccttaaca atgaacaaga tattcgaaaa ataggaggac tactcaaaac catacctctc   13440
acttcaacct ccctcaccat tggcagccta gcattagcag gaatacccttt cctcacaggt   13500 ttctactcca aagaccacat catcgaaacc gcaaacatat catacacaaa cgcctgagcc   13560
ctatctatta ctctcatcgc tacctccctg acaagcgcct atagcactcg aataattctt   13620
ctcaccctaa caggtcaacc tcgcttcccc acccttacta acattaacga aaataacccc   13680
accctactaa accccattaa acgcctggca gccggaagcc tattcgcagg atttctcatt   13740
actaacaaca tttccccgc atccccttc caaacaacaa tcccctcta cctaaaactc   13800
```

-continued

```
acagccctcg ctgtcacttt cctaggactt ctaacagccc tagacctcaa ctacctaacc    13860
aacaaactta aaataaaatc cccactatgc acattttatt tctccaacat actcggattc    13920
taccctagca tcacacaccg cacaatcccc tatctaggcc ttcttacgag ccaaaacctg    13980
cccctactcc tcctagacct aacctgacta gaaaagctat tacctaaaac aatttcacag    14040
caccaaatct ccacctccat catcacctca acccaaaaag gcataattaa actttacttc    14100
ctctctttct tcttcccact catcctaacc ctactcctaa tcacataacc tattcccccg    14160
agcaatctca attacaatat atacaccaac aaacaatgtt caaccagtaa ctactactaa    14220
tcaacgccca taatcataca aagccccgc accaatagga tcctcccgaa tcaaccctga    14280
cccctctcct tcataaatta ttcagcttcc tacactatta aagtttacca caaccaccac    14340
cccatcatac tctttcaccc acagcaccaa tcctacctcc atcgctaacc ccactaaaac    14400
actcaccaag acctcaaccc ctgaccccca tgcctcagga tactcctcaa tagccatcgc    14460
tgtagtatat ccaaagacaa ccatcattcc ccctaaataa attaaaaaaa ctattaaacc    14520
catataacct cccccaaaat tcagaataat aacacacccg accacaccac taacaatcaa    14580
tactaaaccc ccataaatag gagaaggctt agaagaaaac cccacaaacc ccattactaa    14640
acccacactc aacagaaaca aagcatacat cattattctc gcacggacta caaccacgac    14700
caatgatatg aaaaaccatc gttgtatttc aactacaaga acaccaatga ccccaatacg    14760
caaaactaac cccctaataa aattaattaa ccactcattc atcgacctcc cccacccatc    14820
caacatctcc gcatgatgaa acttcggctc actccttggc gcctgcctga tcctccaaat    14880
caccacagga ctattcctag ccatgcacta ctcaccagac gcctcaaccg ccttttcatc    14940
aatcgcccac atcactcgag acgtaaatta tggctgaatc atccgctacc ttcacgccaa    15000
tggcgcctca atattcttta tctgcctctt cctacacatc gggcgaggcc tatattacgg    15060
atcatttctc tactcagaaa cctgaaacat cggcattatc ctcctgcttg caactatagc    15120
aacagccttc ataggctatg tcctcccgtg aggccaaata tcattctgag gggccacagt    15180
aattacaaac ttactatccg ccatcccata cattgggaca gacctagttc aatgaatctg    15240
aggaggctac tcagtagaca gtcccaccct cacacgattc tttacctttc acttcatctt    15300
gcccttcatt attgcagccc taacaacact ccacctccta ttcttgcacg aaacgggatc    15360
aaacaacccc ctaggaatca cctcccattc cgataaaatc accttccacc cttactacac    15420
aatcaaagac gccctcggct tacttctctt ccttctctcc ttaatgacat taacactatt    15480
ctcaccagac ctcctaagcg acccagacaa ttataccccta gccaacccct aaacacccc    15540 tccccacatc aagcccgaat gatatttcct attcgcctac acaattctcc gatccgtccc    15600
taacaaacta ggaggcgtcc ttgccctatt actatccatc ctcatcctag caataatccc    15660
catcctccat atatccaaac aacaaagcat aatatttcgc ccactaagcc aatcactta    15720 ttgactccta gccgcagacc tcctcattct aacctgaatc ggaggacaac cagtaagcta    15780 ccctttacc atcattggac aagtagcatc cgtactatac ttcacaacaa tcctaatcct    15840
aataccaact atctccctag ttgaaaacaa aatactcaaa tgggcctgtc cttgtagtat    15900
aaactaatac accagtcttg taaccggag atgaaaacct ttttccaagg acaaatcaga    15960 gaaaagtct ttaactccac cattagcacc caaagctaag attctaatt aaactattct    16020 ctgttctttc atggggaagc agatttgggt accaccaaag tattgactca cccatcaaca    16080
accgctatgt atttcgtaca ttactgccag ccaccatgaa tattgtacgg taccataaat    16140
acttgaccac ctgtagtaca taaaaaccca atccacatca aaacccctc cccatgctta    16200
```

```
caagcaagta cagcaatcaa ccctcaacta tcacacatca actgcaactc caaagccacc    16260
cctcacccac taggatacca acaaacctac ccacccttaa cagtacatag tacataaagc    16320
cattcaccgt acatagcaca ttacagtcaa atcccttctc gtccccatgg atgacccccc    16380
tcagataggg gtcccttgac caccatcctc cgtgaaatca atatcccgca caagagtgct    16440
actctcctcg ctccgggccc ataacacttg ggggtagcta aagtgaactg tatccgacat    16500
ctggttccta cttcagggcc ataaagccta aatagcccac acgttcccct taaataagac    16560
atcacgatg                                                            16569

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ctcctcaaag caatacactg                                                  20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tgggtggttg gtgtaaatga                                                  20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
acgagtacac cgactacggc                                                  20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
aggctaagcg ttttgagctg                                                  20
```

LUTERIAL AND METHOD FOR ISOLATING AND CULTURING THE SAME

CROSS-REFERENCE TO RELATED APPLICATIONS

This is a continuation-in-part application under 35 U.S.C. § 120 of U.S. patent application Ser. No. 15/109,114 filed Jun. 29, 2016, which in turn is a U.S. national phase under the provisions of 35 U.S.C. § 371 of International Patent Application No. PCT/KR14/004197 filed May 9, 2014, which in turn claims priority of Korean Patent Application No. 10-2014-0004525 filed Jan. 14, 2014. The disclosures of U.S. patent application Ser. No. 15/109,114, International Patent Application No. PCT/KR14/004197, and Korean Patent Application No. 10-2014-0004525 are hereby incorporated herein by reference in their respective entireties, for all purposes.

TECHNICAL FIELD

The present invention relates to luterial which is a mitochondrial-like unidentified nano-sized particle derived from a body fluid and to a method for isolating the same.

BACKGROUND ART

Micro-substances such as microvesicles in blood have previously been recognized as substance having no special function. However, various experimental data have demonstrated that microvesicles also have biological activity. For example, it was found that platelet-derived microvesicles function to stimulate certain cells through vesicular surface proteins (CD154, RANTES and/or PF-4; Thromb. Haemost. (1999) 82:794; J. Biol. Chem. (1999) 274:7545), and it was reported that physiologically active lipids (e.g., HTET or arachidonic acid) in platelet microvesicles have certain effects on certain target cells (J. Biol. Chem. (2001) 276; 19672; Cardiovasc. Res. (2001) 49(5):88). Thus, because the characteristics (e.g., size, surface antigens, determination of cell-of-origin, payload) of substances such as vesicles present in biological samples, can provide a diagnostic, prognostic or theranostic readout, there remains a need to identify biological markers that can be used to detect and treat disease. Accordingly, there has been an attempt to use RNA and other biological markers associated with vesicles as well as the characteristics of vesicles to provide a diagnosis, prognosis, or theranosis (see WO 2011/127219).

Meanwhile, cancer is a disease in which cells grow abnormally to interfere with the functions of normal cells, and typical examples thereof include lung cancer, gastric cancer (GC), breast cancer (BRC), colorectal cancer (CRC) and the like, but cancer can actually occur in any tissue. In the past, the diagnosis of cancer was based on the external change of biological tissue caused by the growth of cancer cells, but in recent years, it has been attempted to perform diagnosis and detection using trace biomolecules (glycol chain, DNA, etc.) present in blood, biological tissue or cells. However, the cancer diagnostic method that is most commonly used is a diagnostic method that uses either a tissue sample obtained through biopsy or imaging. Biopsy, however, causes great pain in the patient, is costly, and requires a long time for diagnosis of cancer. In addition, if a patient has cancer, the cancer can metastasize during biopsy, and in the case of a site from which a tissue sample cannot be obtained through biopsy, there is a disadvantage in that the diagnosis of disease is impossible before a tissue suspected of having the disease is extracted by a surgical operation. Meanwhile, in diagnosis based on imaging, cancer is diagnosed based on X-ray imaging, nuclear magnetic resonance (NMR) imaging employing an imaging agent having a disease-targeting agent attached thereto, or the like. However, this imaging-based diagnostic method has disadvantages in that an erroneous diagnosis may result from the low skill of a clinical physician or an interpreting physician and in that the method greatly depends on the precision of an imaging device. Furthermore, the imaging-based diagnostic method has a disadvantage in that it is difficult to detect disease in an early stage, because even the most precise device cannot detect a tumor having a size of several mm or less. In addition, the imaging-based diagnostic method has disadvantages in that, because a patient or a person suspected of having disease is exposed to high-energy electromagnetic waves for imaging, which can cause a genetic mutation, the method can cause another disease, and in that the number of diagnoses by imaging is limited.

In other words, biopsy for cancer diagnosis is time-consuming, costly, inconvenient, and causes pain. For this reason, there is a need for a method capable of significantly reducing the number of unnecessary biopsy procedures, as well as a method capable of diagnosing cancer at an early stage.

Under such circumstances, the present inventors found that a disease can be diagnosed and predicted by observing the characteristics of a micro-substance present in a body fluid discharged from a patient. The content of this finding was filed for a patent on Jul. 12, 2013 (Korean Patent Application No. 10-2013-0082060). The present inventors named the unidentified nano-sized particle a "luterial".

However, a technology of efficiently isolating and culturing the micro-substance luterial so as to be capable of being clinically applied has not been known.

Accordingly, the present inventors have developed a method capable of effectively isolating the unidentified nano-sized particle luterial present in a body fluid discharged from a patient or a normal person and have characterized luterial isolated by this method, thereby completing the present invention.

DISCLOSURE OF INVENTION

Technical Problem

It is an object of the present invention to provide a method for isolating and culturing luterial present in a body fluid discharged from a patient or a normal person.

Another object of the present invention is to provide luterial which has integrative characteristics corresponding to those of an intermediary between a prokaryote and an eukaryote, shows a positive fluorescence staining reaction with Janus Green B, Mitotracker Red and Rhodamine 123, is mobile, and has the ability to produce ATP.

Technical Solution

To achieve the above object, the present invention provides a method for isolating luterial from body fluid comprising one or more of the following characteristics:

(a) it shows a positive staining reaction with Janus green B, Acridine Orange and Rhodamine 123 in a fluorescence test;

(b) in an optimal environment (pH 7.2-7.4), it expresses beta-proteobacteria-derived and gamma-proteobacteria-derived genes and has a size of 30-800 nm;

(c) in an acidic environment, it expresses not only beta-proteobacteria-derived and gamma-proteobacteria-derived genes, but also eukaryote Streptophyta genes and grows to a size of 400 nm-2000 nm or more;

(d) it is involved in ATP production in normal conditions;

(e) it is a cell or cell-like structure completely different from mitochondria or exosomes;

(f) it is circular or oval in shape in a normal status, and patient-derived luterial has a size (long axis diameter: 800 nm or more) greater than that of normal-status luterial and is mutated to form mutant luterial having a non-uniform morphology;

(g) it has a double-layered, multiple layered ring-like membrane structure or a mixed form of double-layered and multiple layered membrane structure and is adherent;

(h) it can be present inside or outside cells;

(i) it is mobile and undergoes fusion and/or fission events;

(j) mutant luterial bursts in a certain condition and has sternness after bursting;

(k) it has a function of regulating p53 gene and telomeres;

(l) express at least one protein selected from the group consisting of CD14, CD24, CD29, CD34, CD39, CD44, CD45 (CD45RA/CD45RO), CD73, CD90, CD105, CD133, CD173, CD326, CD332, OCT4, ND1 (OXPHOS complex I), CO1 (OXPHOS complex IV), ATP6 (OXPHOS complex V), ATP8 (OXPHOS complex V), RNR1, RNR2 and 7S; and (m) found in the fraction with 0.99 or less density in 5-70%, preferably 15-60% sucrose density gradient.

The present invention also provides a method for isolating luterial comprising a polynucleotide sequence having at least 99% sequence identity to polynucleotide sequence of SEQ ID NO: 24 (sequence of Luterial genome map) or a complementary polynucleotide sequence thereto.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2B: 50.1-85.1 nm, an ultra-high resolution microscope (SR-GSD) image after staining with Mito-tracker Red; FIG. 2C: 76.5 nm, a transmission electron microscope image; FIG. 2D: 160 nm, a transmission electron microscope image; FIG. 2E: 170-230 nm, a transmission electron microscope image, a multiple-membrane structure; FIG. 2F: 234 nm, an image after staining with Janus green B; FIG. 2G: 250 nm, an atomic force microscope image; FIG. 2H: 361 nm, a transmission electron microscope image; FIG. 2I: 650.1 nm, a transmission electron microscope image; and FIG. 2J: a laser scanning microscope image of luterial having a size of 5 μm or more after staining with DAPI (4',6-diamidino-2-phenylindole).

FIG. 7B: after 1 second; FIG. 7C: after 3 seconds).

FIG. 8 shows life cycling A of normal luterial and life cycling B of mutated luterial.

FIGS. 10A and 10B show luterial isolated from the cancer patient body fluid. Specifically, FIG. 10A shows cancer patient-derived luterial while forming elongated branches, and FIG. 10B shows cancer patient-derived luterial stained with DAPI (4',6-diamidino-2-phenylindole), Mito-tracker and Rhodamine 123.

FIG. 13 depicts images showing the results of scratching luterial with an atomic force microscope probe and removing the membrane.

FIG. 15 depicts images showing the results of scratching luterial with an atomic force microscope probe, and then observing DNA through a DAPI-stained image.

In FIG. 19, the exosome has a size of 20-120 nm, an unclear membrane and a relatively light internal color, and the luterial has a size of 20-800 nm and a distinct membrane or a packed internal structure.

FIG. 20 depicts photographs comparing the morphology between luterial, exosome and microvesicle.

FIG. 21 depicts transmission electron microscope (TEM) images of a luterial library described in an example of the present invention.

FIG. 24B: 100-200 nm; FIG. 24C: 200-400 nm; FIG. 24D: 400-800 nm).

FIGS. 25A through 25D show percentage of bacterial homology of luterial DNA as determined by 16S rRNA sequencing of luterials having various sizes, derived from blood and sperm which are in a fatigue and disease status (pH: 7.0 or less) (FIG. 25A: 100 nm or less; FIG. 25B: 100-200 nm; FIG. 25C: 200-400 nm; and FIG. 25D: 400-800 nm).

BEST MODE FOR CARRYING OUT THE INVENTION

Figure 1:
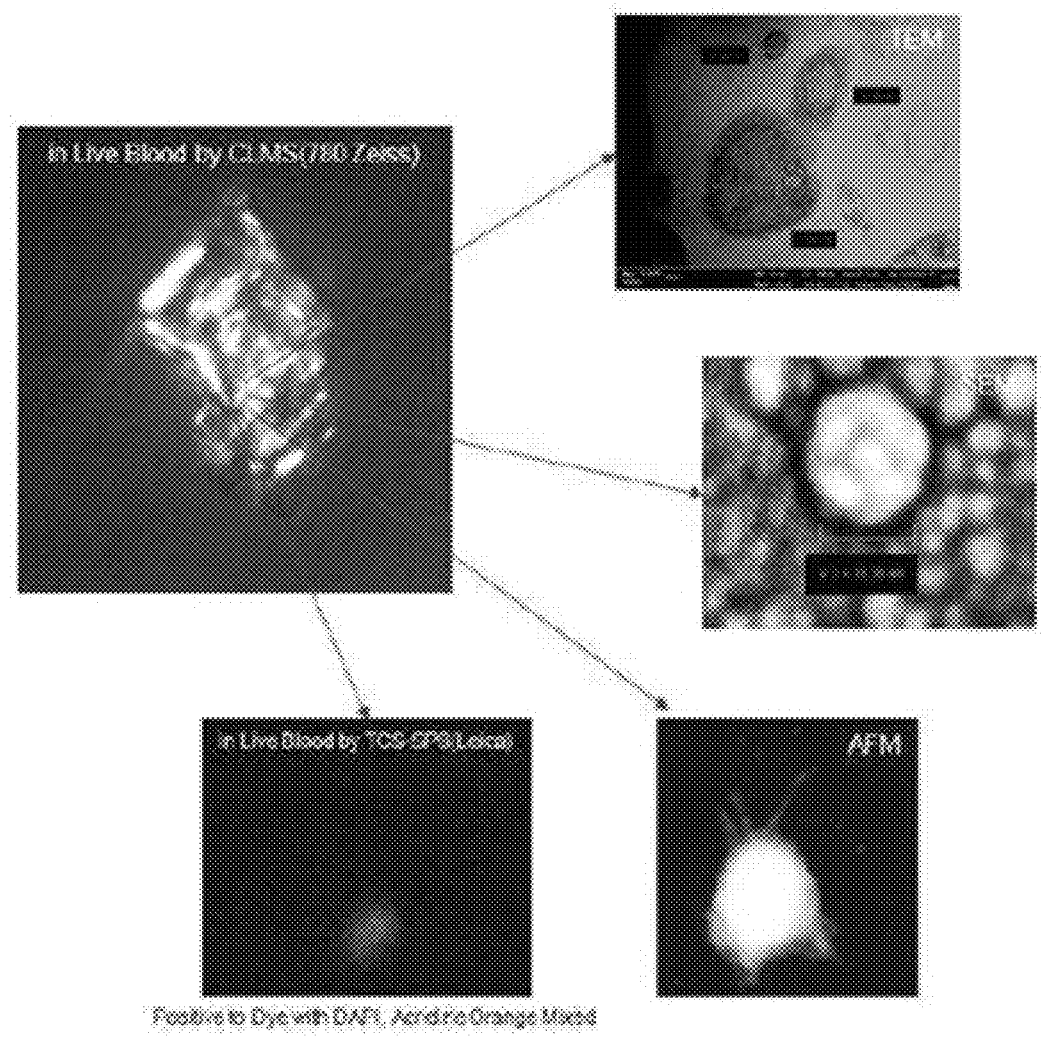
FIG. 1 shows images of the blood-derived unidentified nano-sized particle luterial imaged with a confocal laser scanning microscope (Zeiss), a transmission electron microscope, a scanning electron microscope, an atomic force microscope and a confocal scanner (Leica TCS-SP8).
Figure 2A:
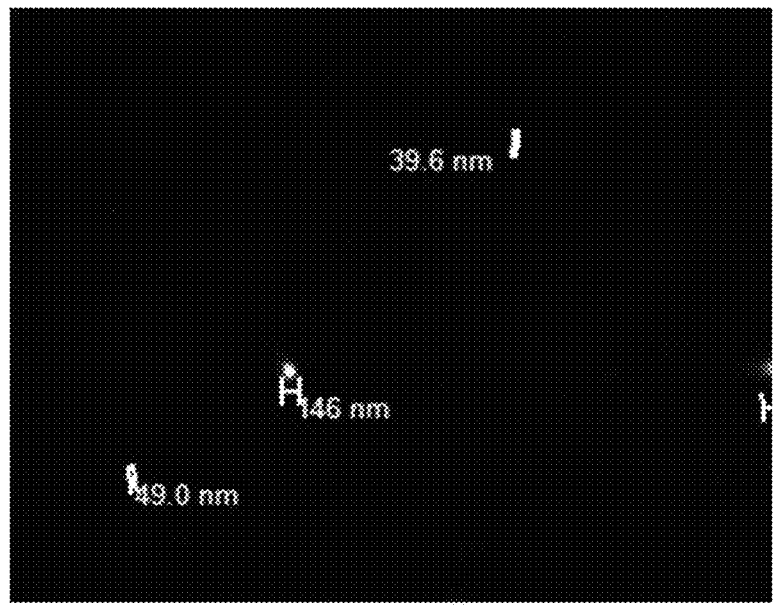
FIGS. 2A through 2J depict images showing the shape or morphology of luterial with various sizes (FIG. 2A: 39.6-49.0 nm, an ultra-high resolution microscope (SR-GSD) image after staining with Mito-tracker Red.
Figure 2B:
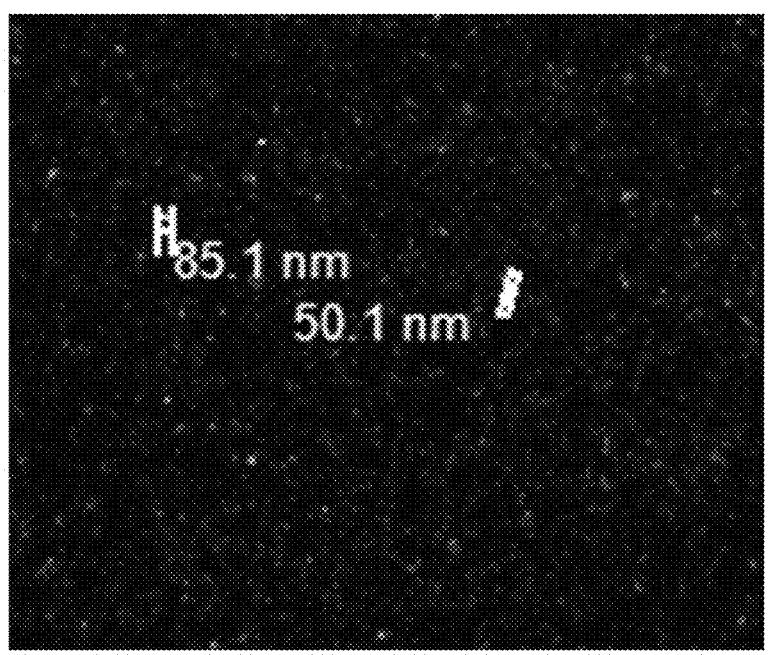
Figure 2C:
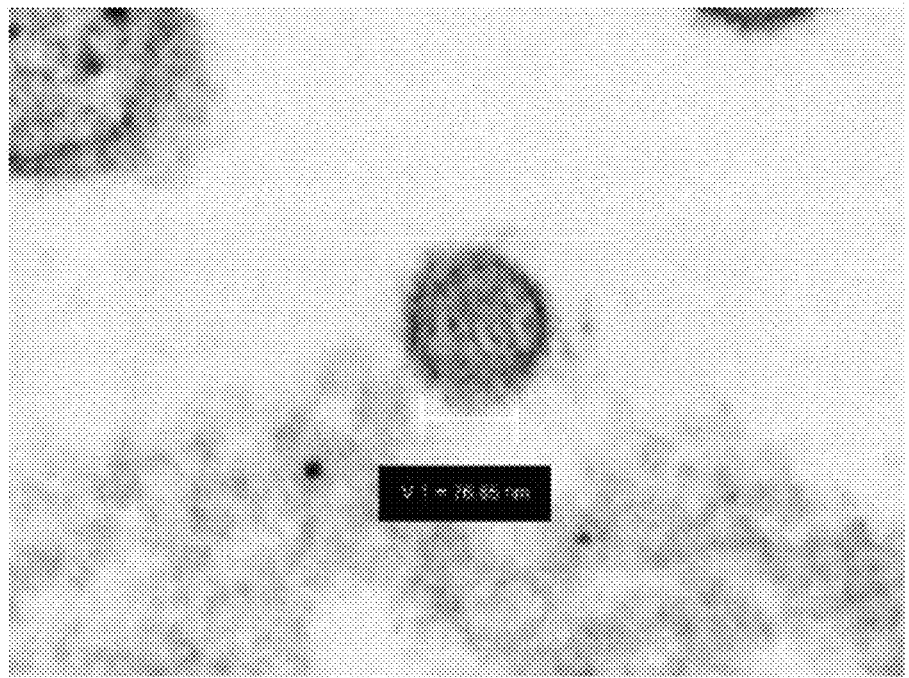
Figure 2D:
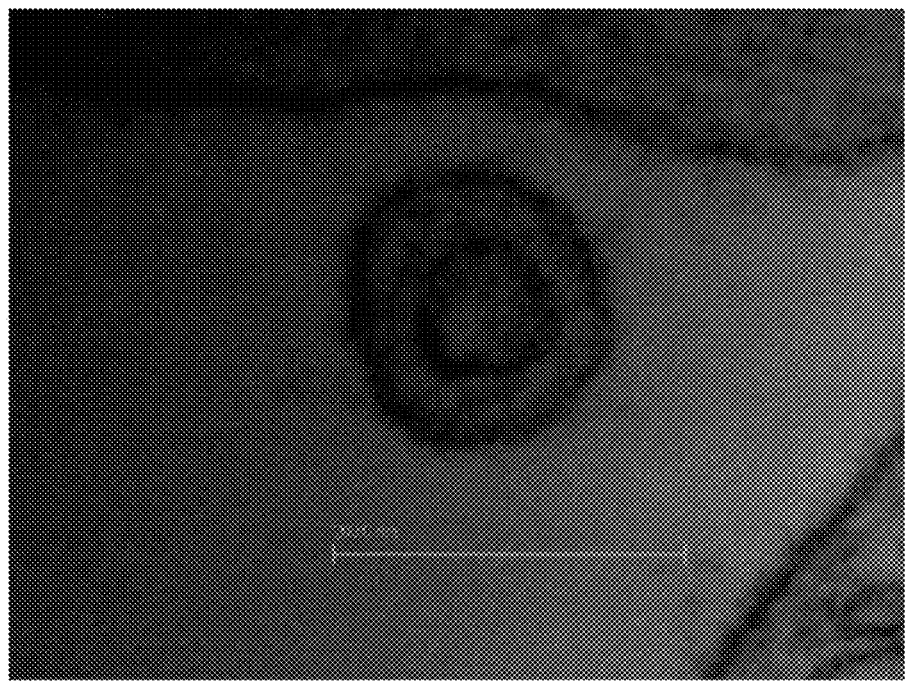
Figure 2E:
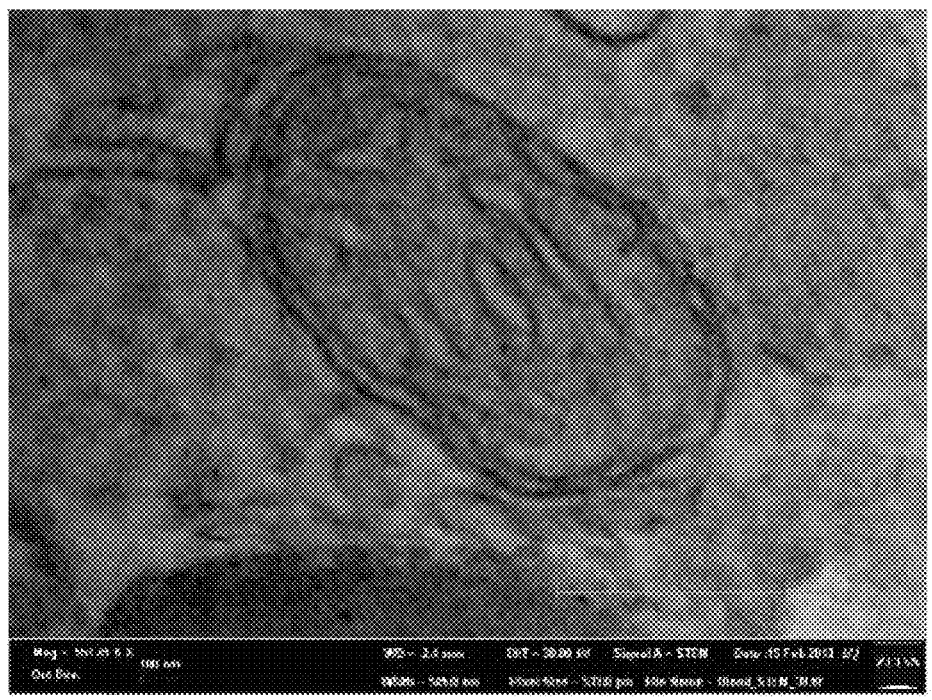
Figure 2F:
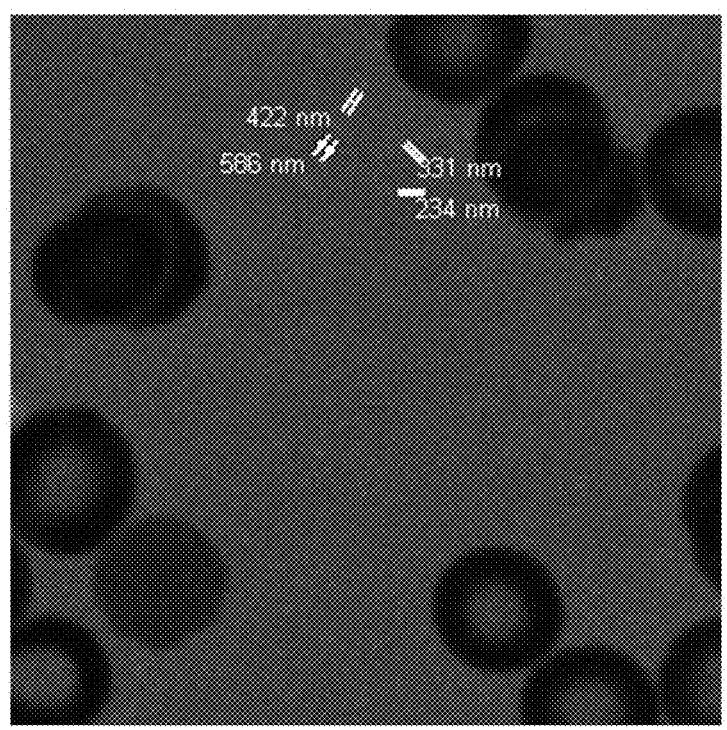
Figure 2G:
Figure 2H:
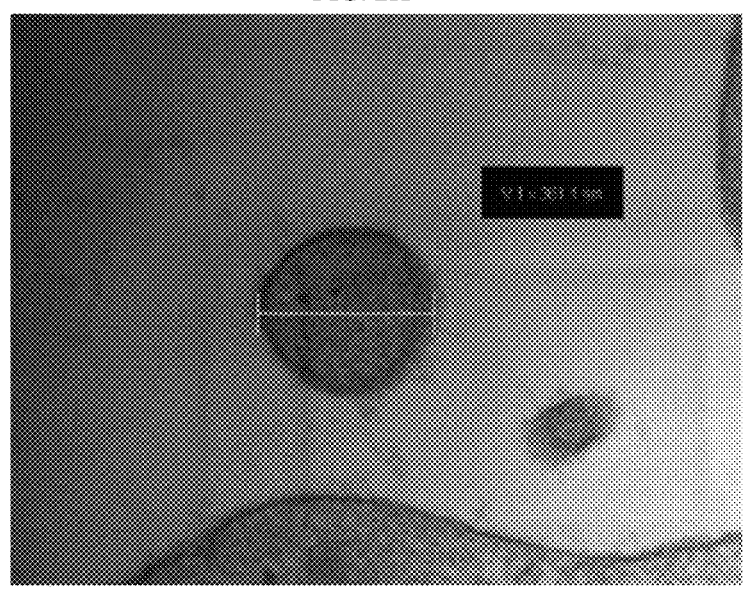
Figure 2I:
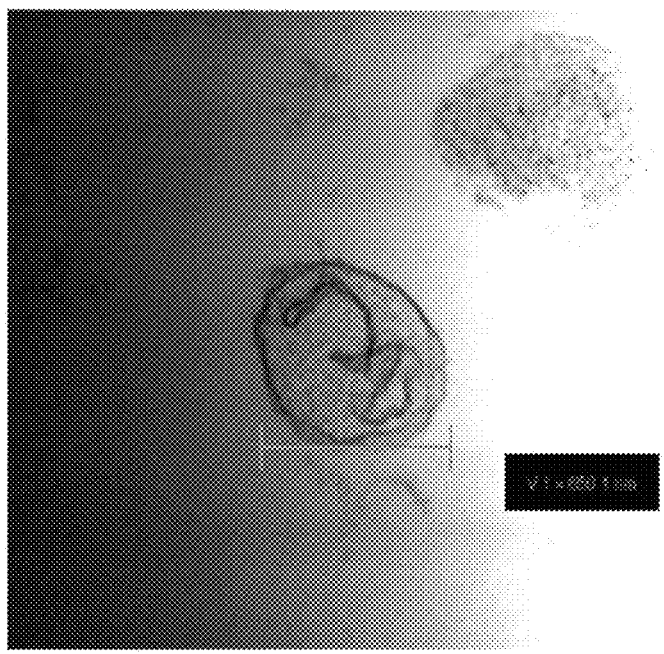
Figure 2J:
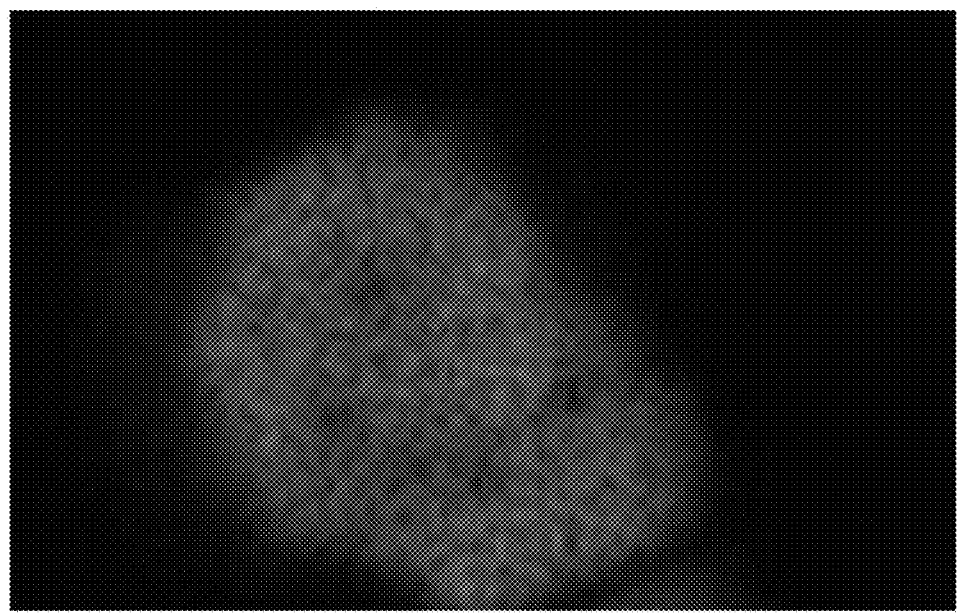
Figure 3:
FIG. 3 is an image showing the results of staining luterial with Rhodamine 123 and then observing whether the luterial would be positively stained.
Figure 4:
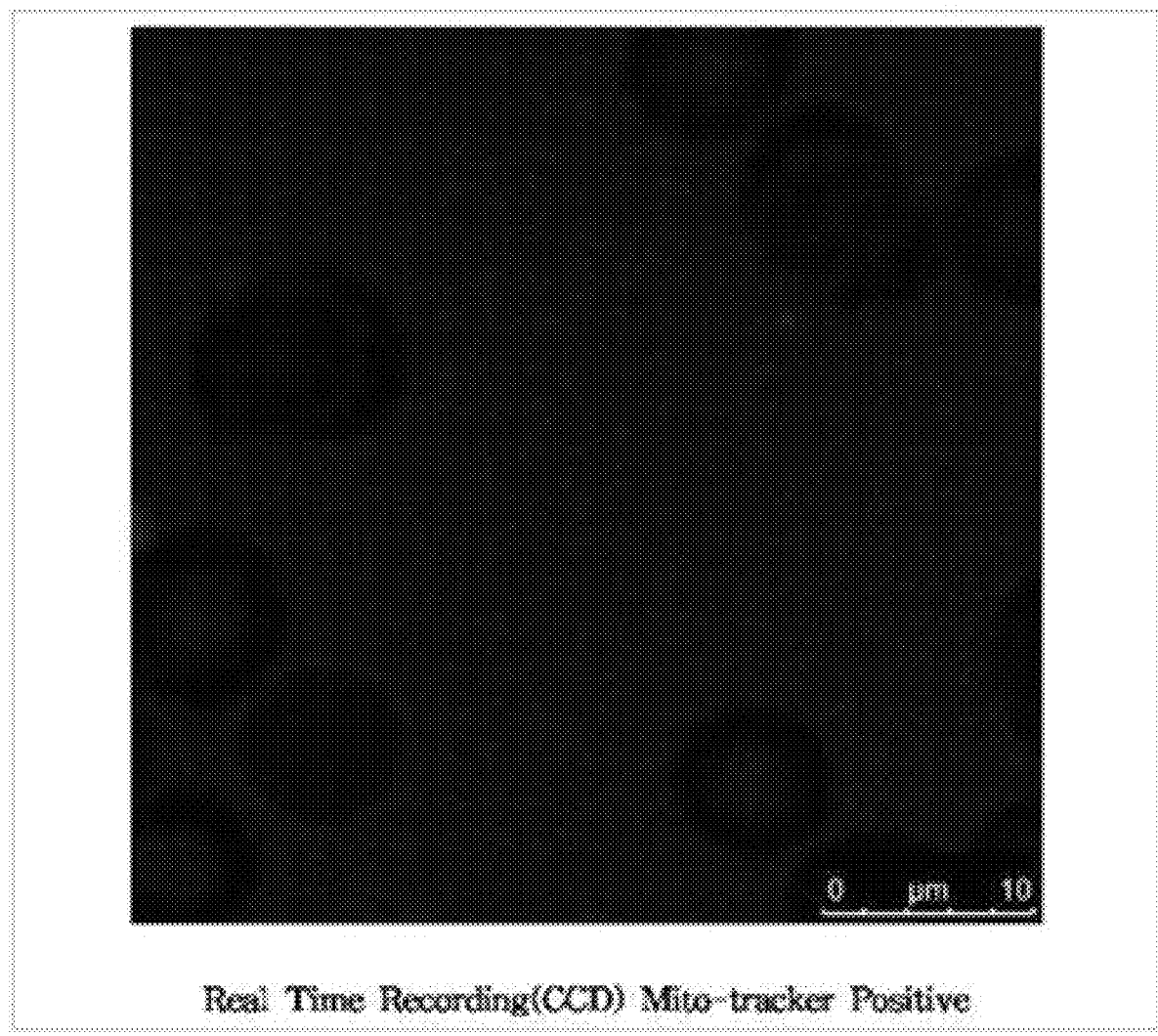
FIG. 4 is an image showing the results of staining luterial with Mito-tracker and then observing whether the luterial would be positively stained.

Unless defined otherwise, all technical and scientific terms used herein have the same meaning as commonly understood by a skilled expert in the field to which the invention pertains. Generally, the nomenclature used herein and the experiment methods, which will be described below, are those well known and commonly employed in the the technical field to which the invention pertains.

As used herein, the term "luterial" named by the present inventors refers to a living organism present in animals and means a fine substance having a size ranging from a size similar to that of virus to about 800 nm (20-800 nm, 20~400 nm at normal fission stage, 50~400 nm at fusion stage/800 nm or more at abnormal fusion stage). Luterial has the following characteristics: (1) it is a cell or cell-like structure having integrative characteristics corresponding to those of an intermediary between a prokaryote and an eukaryote; (2) it is present in body fluids, including blood, sperm, intestinal juices, saliva, cellular fluids, etc.; (3) it shows a positive staining reaction with Janus green B, Acridine Orange and Rhodamine 123 in afluorescence staining test; (4) in an optimal environment (pH 7.2-7.4), it has the property of expressing genes homologous to beta-proteobacteria and gamma-proteobacteria and has a size of 30-800 nm; (5) in an acidic environment, it expresses not only genes homologous to beta-proteobacteria and gamma-proteobacteria, but also eukaryotic genes (particularly Streptophyta genes), and grows to a size of 400-2000 nm or more; (6) it is involved in ATP production under normal conditions; and (7) it is a cell or cell-like structure which differs from mitochondria and completely differs from exosomes. The luterial is present in blood (plasma, serum, Red blood cells, white blood cells, platelets, etc.) derived from mammals (including humans), saliva, lymphatic duct, breast milk (in particular, colostrum), umbilical cord blood, brain cells, spinal cord, bone marrow, majority of cells including hematopoietic cells, stem cells, reproductive cells (eggs, sperm, semen, vaginal fluid, etc.), in horns in case of animals with horns, and fluid from plants.

Luterial according to the present invention is distinctive from exosome and/or microvesicle, in a view that only luterial shows self-motility.

Further, at least one protein selected from the group consisting of CD14, CD24, CD29, CD34, CD39, CD44, CD45 (CD45RA/CD45RO), CD73, CD90, CD105, CD133, CD173, CD326, CD332, OCT4, ND1 (OXPHOS complex I), CO1 (OXPHOS complex IV), ATP6 (OXPHOS complex V), ATP8 (OXPHOS complex V), RNR1, RNR2 and 7S is(are) specifically expressed in Luterial. The specifically expressed proteins in luterial could function as a marker and based on the expression of the maker, luterial might be separated from other membrane-bound vesicles termed extracellular vesicles (EVs), such as exosome and/or microvesicle.

Luterial according to the present invention comprises a polynucleotide sequence having at least 99% sequence identity to polynucleotide sequence of SEQ ID NO: 24 (sequence of luterial genome map) or a complementary polynucleotide sequence thereto.

In addition, luterial according to the present invention shows at least 99% sequence identity to that of mitochondria as a result of WGS (Whole Genome Sequencing), and shows 16 luterial specific point variations, when compared to those of mitochondria, according to genome map.

Luterial specific point variations compared to those of mitochondria are in positions of 150, 183, 309, 4793, 4833, 5108, 7867, 8200, 8701, 11914, 14569, 15323, 15497, 15860, 16325 and 16519 of sequence as set forth in SEQ ID NO:24. Luterial specific point variations at 16 positions might be described as follows:

T in position 150,
G in position 183,
CC or CCC in position 309,
G in position 4793,
G in position 4833,
CC or CCC in position 5108,
T in position 7867,
C in position 8200,
G in position 8701,
A in position 11914,
A in position 14569,
A in position 15323,
A in position 15497,
G in position 15860,
C in position 16325, and
C in position 16519 of sequence as set forth in SEQ ID NO:24.

TABLE 1

| Position | Point Variations | |
|---|---|---|
| | Mitochondria | Luterial |
| 150 | C | T |
| 183 | A | G |
| 309 | C | CC, CCC |
| 4793 | A | G |
| 4833 | A | G |
| 5108 | T | CC, CCC |
| 7867 | C | T |
| 8200 | T | C |
| 8701 | A | G |
| 11914 | G | A |
| 14569 | G | A |
| 15323 | G | A |
| 15497 | G | A |
| 15860 | A | G |
| 16325 | T | C |
| 16519 | T | C |

Figure 28:
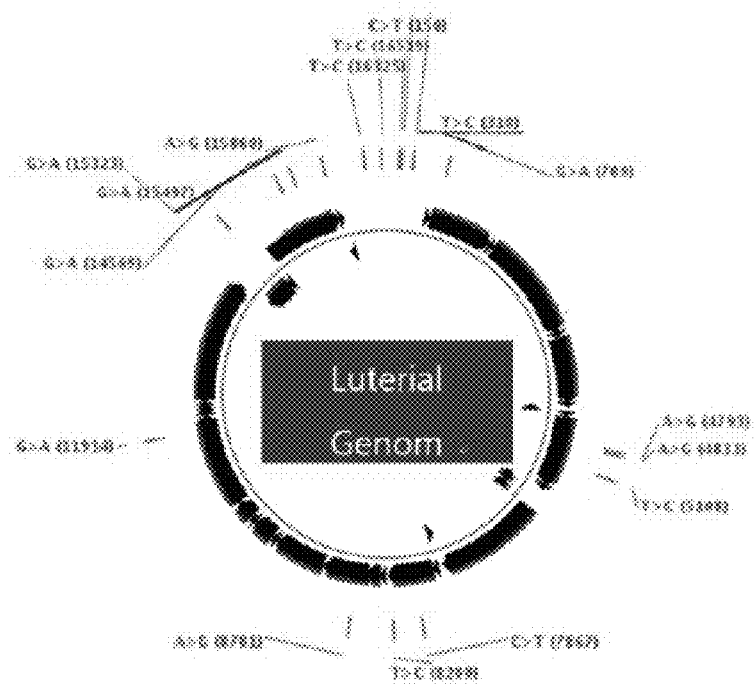
FIG. 28 shows genome map of subject 1 indicating sequence of luterial (SEQ ID NO: 24) and point variations in luterial specific bases, which are distinctive from sequences of mitochondria collected from the same subject.
Figure 29:
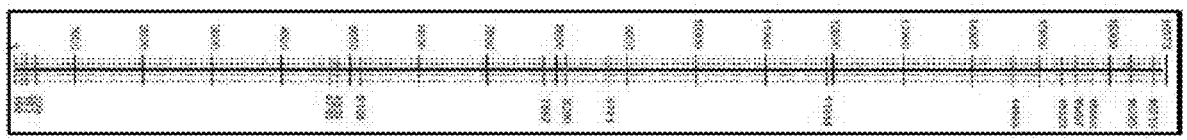
FIG. 29 shows genome map indicating positions of point variations in luterial specific bases, when compared to sequences of mitochondria, and positions of point variations in 16 luterial specific bases, existing in common through the various subjects.

Innate genome map of luterial with variations in 16 luterial specific bases is shown in FIG. 28 and luterial specific 16 bases in sequence of luterial (SEQ ID NO: 24) are shown in FIG. 29.

Meanwhile, luterial according to the present invention is distinctive from exosome and/or mitochondria, in a view that luterials according to the present invention express proteins (such as surface antigens) different from those expressed in exosome and/or mitochondria.

For example, ATP related proteins such as ND1 (OXPHOS complex I), CO1 (OXPHOS complex IV), ATP6 (OXPHOS complex V), ATP8 (OXPHOS complex V), RNR1, RNR2 and/or 7S are expressed in luterial.

Biomarkers such as CD14, CD24, CD29, CD34, CD39, CD44, CD45 (CD45RA/CD45RO), CD73, CD90, CD105, CD133, CD173, CD326, CD332, and/or OCT4 are specifically expressed in luterial. Above mentioned biomarkers expressed in luterial are not observed in mitochondria, and biomarkers such as CD63 and/or CD81, which are not expressed in luterial, are observed in exosome and biomarkers specifically expressed in luterial are not observed in exosome. Luterial according to the present invention is distinctive from exosome and/or mitochondria, in a view that luterial according to the present invention express biomarkers different from those expressed in exosome and/or mitochondria.

Luterial according to the present invention might be living organism is present in intracellular and/or extracellular condition, which could survive under strong acid and/or strong alkali condition, and having motility without bursting at 200,000 g or more in spin of ultracentrifugation.

Innate characteristic of luterial according to the present invention is described in Table 2 as follows:

TABLE 2

| | Method | target | Exosome | hLTL | Mito | Platelet |
|---|---|---|---|---|---|---|
| Protein | Western Blot | Flotillin | + | − | | |
| | | CD9 | + | − | | |
| | | CD63 | + | − | | |
| | | CD81 | + | − | | |
| | | VDAC | − | + | + | |
| | | CD332 | − | + | | |
| | | CD39 | + | + | | |
| | | CD73 | + | + | | |
| | | CD42 | − | − | − | + |
| Mobility ( >after 1400,000 g) | +Motile | Motile | | + | | |
| PCR | qRT PCR (RNA --→ cDNA) | GAPDH | | | | |
| | | NADH | | | | |
| | | MT ATP6 | | | | |
| Density | Gradient | Sucrose | 1.03~ | 0.9~0.992 | | |
| DNA | Southern Blot | DNA | | + | + | |
| RNA | Northern Blot | RNA | | + | + | |
| | | 12SrRNA | | + | + | |
| | | 16SrRNA | | + | + | |
| | | 18SrRNA | | | | |
| | | 28SrRNA | | | | |
| Embryo Stem Cell | (Immuno Fluorescence) | CD44 | | | | |
| | | CD326 | | | | |
| | | CD133 | | | | |
| | | OCT-4 | | | | |
| Mitochondria Homology | Capillary Seq (WGA) | | | | | |
| gDNA seq (a-b-r Proteobacteria Homology) | WGS | | | | | |
| ProteoBacteria γ Homology | Metagenomics | | | | | |
| Protoemics (ABC Transporter) | Maldi | | | | | |
| Spin | 200K(g) | Pellete supernadant | | | | |

"+" addressed in Table 2 shows positive results in having referenced marker, RNA sequence or character, "−" addressed in Table 2 shows negative results in not having referenced marker, RNA sequence or character.

Luterial according to the present invention might have further variations in respective individuals. The variations, for example, could include polymorphisms having at least two alleles at one locus, and single or more base(s) in specific position of innate genome map could be different and distinctive among respective individuals. Polymorphism might include single nucleotide polymorphism (SNP), which is a variation in a single nucleotide that occurs at a specific position in the genome. For example, polymorphism might include at least two alleles occurring with frequency of 1% or more, 5% or 10% or more.

The alleles might refer to one of a number of alternative forms of the same gene or same genetic locus, and alleles might be used for showing polymorphism. Single nucleotide polymorphism, for example, might have biallelic polymorphic site.

Normal luterials have a size of 20-800 nm, for example 20-400 nm in case of fission, 50-400 nm in case of fusion, and mutant luterials formed by fusion have a size of a few tens of micrometers. The term "luterial" may refer to proto mitochondria containing mRNA, miRNA and DNA. Luterial is unique in that it does not dissolve in digestive fluid and infiltrates into blood.

It is expected that luterial will be closely associated with not only signal transduction, cell differentiation and cell death, but also the regulation of cell cycling and cell growth. The present inventors have found that luterial is closely associated with the diagnosis of cancer.

Normal luterial is expected to function to prevent the growth of cancer cells and return cells to a healthy immune state, and the functions thereof are performed by its RNAi (RNA interference) activity that works to normalize genes. When an information system in RNA in the blood of healthy people or animals deviates from a normal status and directs to produce a protein that causes an abnormal disease, luterial will deliberately interfere with the information system so as to inhibit the development of diseases such as cancer. When luterial grows to a size of 200-500 nm or more, it will also be involved in energy metabolism, and when luterial is irradiated with light having a certain wavelength, it will function to amplify light energy in response and will act like chlorophyll. Thus, if luterial does not perform normal functions, it can cause a serious disorder in homeostasis and ATP production and can cause diseases in both respiration and energy metabolism.

Mutant luterials that cannot perform normal functions as described above show phenomena and characteristics different from those of normal luterials and have various sizes or shapes. Specifically, normal luterials ceases to grow after they form double spores, but mutant luterials that are found in the blood of cancer patients or patients with chronic diseases have the property of growing infinitely, similar to stem cells, and thus have a size ranging from 600-800 nm to 200 μm (200,000 nm) or even bigger. In addition, similarly to viruses, luterials show unique characteristics that could enter and grow inside erythrocytes, leukocytes, platelets or the like or aggregate with other luterials.

Thus, it is expected that diseases can be diagnosed or treated by observing the morphological or biochemical characteristics of luterial and thereby promising its wide use in countless applications. However, luterial isolated from body fluids discharged from animals (including humans) is difficult to observe as it quickly disintegrates in vitro or undergoes morphological changes. Furthermore even the normal luterial is changed into mutant luterial within 24 hours under an abnormal environment, making it difficult to accurately diagnose or treat diseases.

In the present invention, the unidentified nano-sized particle luterial present in body fluids isolated from patients or normal people was isolated by two methods.

Therefore, in one aspect, the present invention is directed to a method for isolating luterial from a body fluid.

A first method according to the present invention is a method for isolating luterial from blood, comprising the steps of: (1) separating platelet and blood-derived substances having a size greater than that of platelet from blood; (2) centrifuging the blood after the removal of platelet and the blood-derived substances having a size greater than that of platelet; (3) isolating luterial from a resultant supernatant obtained from centrifugation; and (4) washing the isolated luterial.

Step (1) may comprise a step of passing the blood through a filter having a pore size of 0.8-1.2 μm and removing unfiltered substances. Step (2) may comprise a step of repeatedly centrifuging the blood at 1,200-5,000 rpm for 5-10 minutes to remove general microvesicles such as exosomes and recovering the supernatant. Step (3) may comprise a step of irradiating visible light to the supernatant obtained by the centrifugation and isolating mobile luterial particles, which are gathered toward light, by pipetting. The blood used in step (1) may be derived from humans among mammals. Luterial is autofluorescent and mobile, and thus luterial particles in the supernatant can be isolated by pipetting the visualized luterial under a dark-field microscope or a confocal microscope with the assistance of irradiation of visible light. Luterial isolated in step (3) may be passed through a filter having a pore size of 20 nm, and an unfiltered portion may be washed out with PBS for isolation of luterial. Because luterial has a long axis diameter of 20 nm or more, blood-derived substances smaller than luterial can be removed by the above-described procedure.

A second method according to the present invention is a method for isolating luterial from a body fluid such as blood or sperm, comprising the steps of: centrifuging the body fluid to provide a supernatant, and filtering the supernatant through a filter having a pore size of 2-5 μm, thereby obtaining a filtered solution; and centrifuging the filtered solution to provide a supernatant, and filtering the supernatant through a filter having a pore size of 0.5-2 μm.

Specifically, the second method may comprise the steps of: centrifuging the body fluid at 2,000-4,000 rpm for 5-30 minutes to provide a supernatant, and filtering the supernatant through a filter having a pore size of 2-5 μm; and centrifuging the filtered solution at 3,000-7,000 rpm for 5-20 minutes, followed by filtration through a filter having a pore size of 0.5-2 μm.

The second method may further comprise a step of irradiating visible light to the filtered solution and isolating mobile luterial particles, which are gathered toward the light, by pipetting. Herein, the luterial is autofluorescent and mobile, and thus luterial particles in the supernatant can be visualized by irradiation with visible light. The isolated luterial may be passed through a filter having a pore size of 20 nm, and an unfiltered portion may be washed out with PBS, thereby obtaining luterial. Because luterial has a long axis diameter of 20 nm or more, blood-derived substances smaller than luterial can be removed by the above-described procedure.

In another embodiment of method for isolating luterial according to the present invention, the method comprises (a)

laying body fluid on top of sucrose gradient with tiers of 5-70% of sucrose concentration; and (b) centrifuging the body fluid laid on top of the sucrose gradient in the step (a). According to the method for isolating luterial of the present invention, a target material might be separated from other materials based on the density (or specific gravity) of the target material, by using sucrose concentration gradient.

One embodiment of the present invention, the method might comprise adjusting sucrose gradient in a range of 5-70%, for example adjusting sucrose gradient to 8%, 15%, 40% and 60%. Plasma might be laid on top of the sucrose with concentration gradient, and then centrifuging is performed. If the concentration of sucrose is too low, centrifugation could not occur due to the low sucrose density compared to the density of luterial that should be isolated, and if the concentration of sucrose is too high, centrifugation could not occur due to the high sucrose density compared to the density of luterial that should be isolated, either. When referring to the result of experiments as mentioned in Examples of the present invention, luterial might be found in 0.99 or less fraction, and this would separate luterial from exosome showing density of at least 1.0.

One embodiment of the present invention, centrifuging might be desirably performed at 100,000 g or more, for example under 200,000 g for 0.5 min to 24 hrs, and luterial, which is present on upper section of supernatant with a sucrose density of 0.9 to 0.99, might be separated.

The luterial isolated by each of such two methods can be observed by a dark-field microscope or a confocal microscope, and can be divided according to size into 20-200 nm (developmental phase)/200-400 nm (maturation phase)/400-600 nm (mitosis phase)/600-800 nm (over-mitosis phase) by sequential use of 200 nm, 400 nm, 600 nm, 800 nm and 1000 nm filters.

In the present invention, the isolated luterial was characterized.

(1) Morphology

Luterials were found in the fraction with 0.99 or less density in 5-70%, preferably 15-60% sucrose density gradient, and showing distinctive density from other EVs or cells. Further, bursting at 200,000 g or more in spin of ultracentrifugation did not occur.

Luterials could survive under strong acid and/or strong alkali condition, and the motile luterials were extremely resistant to reagents that are commonly known to dissolve cellular membranes. Even after 60 min of incubation in TriZol, these luterials remained intact and motile when viewed under the dark field microscope.

As to the range of the diameter of luterials found in human blood, the blood samples were obtained from 7 healthy individuals with age ranging from 27 to 52 and subjected to ultracentrifugation at 140,000 g followed by filtration with 800 nm pore size. The resultant filtrate was then analyzed under Nanoparticle Tracking Analysis (NTA) using Nanosight. The diameter of the ultracentrifuge collected from the standard protocol ranged from 20-800 nm with an average of 176.6±37.3 nm. The ultracentrifuge was present at the concentration of $3.7±2.6×10^{12}$ units/ml of plasma. The concentration of the ultracentrifuge in plasma obtained from 6 cancer patients was significantly lower at $0.4±0.3×10^{12}$ units/ml (p=0.02; Mann-Whitney U test).

Luterials obtained from the healthy individuals manifested self-mobility with the speed of 275±12 nm/s (n=20). This innate mobility was significantly lower in cancer patients at 1.3±0.1 μm/s (n=27, p<0.001; Mann-Whitney U test).

Figure 12:
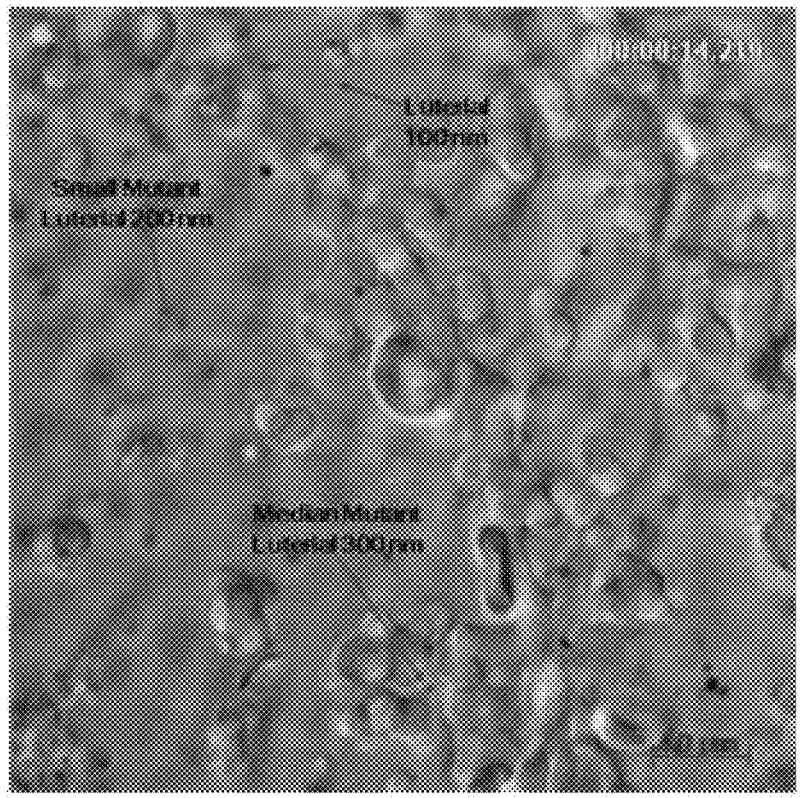
FIG. 12 is an image showing the results of measuring the sizes of luterial and mutated luterial.
Figure 14A:
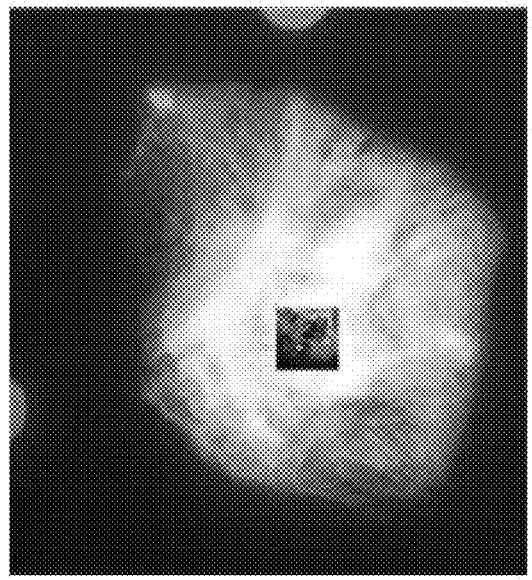
FIGS. 14A and 14B are atomic force microscope images of mutated luterials that are in a fusion status.
Figure 14B:
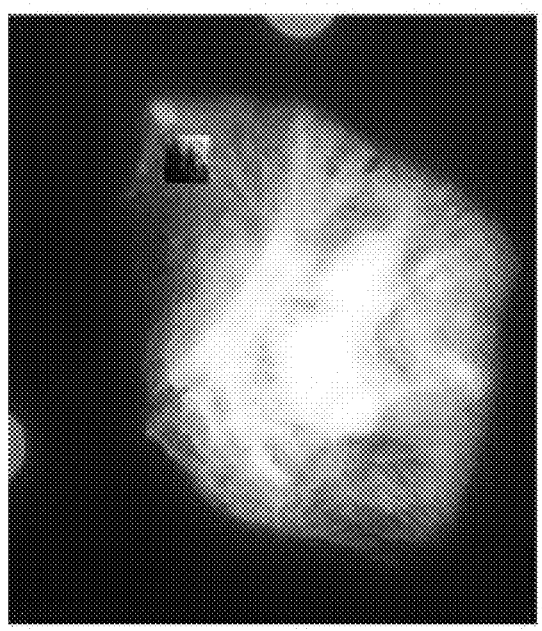
Figure 14C:
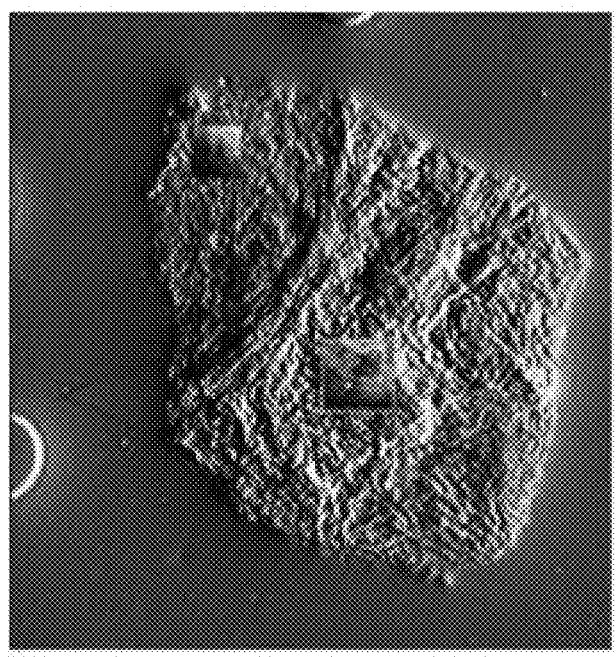
FIGS. 14C and 14D show the results of imaging the mutated luterials with an atomic force microscope after peeling off the membrane with a cantilever.
Figure 14D:
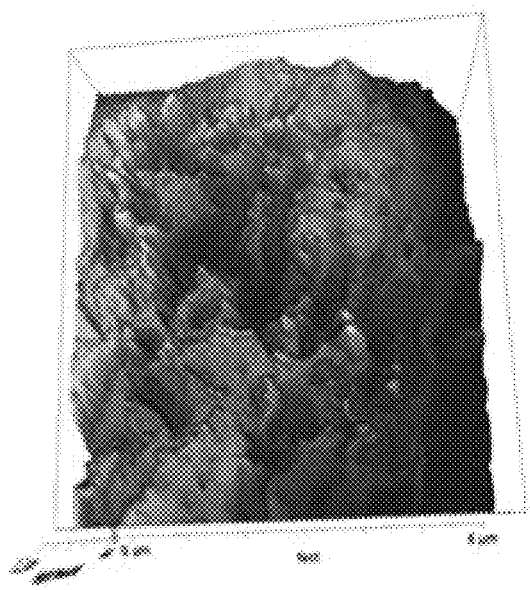

It was found that normal luterials have a size of 20-800 nm (FIG. 2 and FIG. 12), and grow up to a size of 800 nm in the absence of abnormal fusion. The patient-derived luterials have a size (long axis diameter of 800 nm or more) greater than that of healthy person-derived luterials, are mutated to form mutant luterials having a non-uniform morphology, and grow to a size of several thousands of nm when abnormal fusion persists.

In addition, luterial is circular or oval in shape, and shows a multiple ring-like membrane structure in SEM or TEM images, but had no internal cristae structure (FIG. 1).

(2) Fluorescent Staining

It is known that mitochondria are positively stained by Janus green B and fluorescent dyes, including Rhodamine 123, Mitotracker, Acridine Orange, and DAPI, and it was found that luterial is also stained by the same dyes as those for mitochondria. Fluorescence images indicated that the luterial, but not exosomes, showed a reaction similar to that of mitochondria in fluorescent staining test and showed autofluorescence (FIGS. 2A, 2B, 2F and 2J, and FIG. 3 through FIG. 6).

(3) Properties

Figure 9:
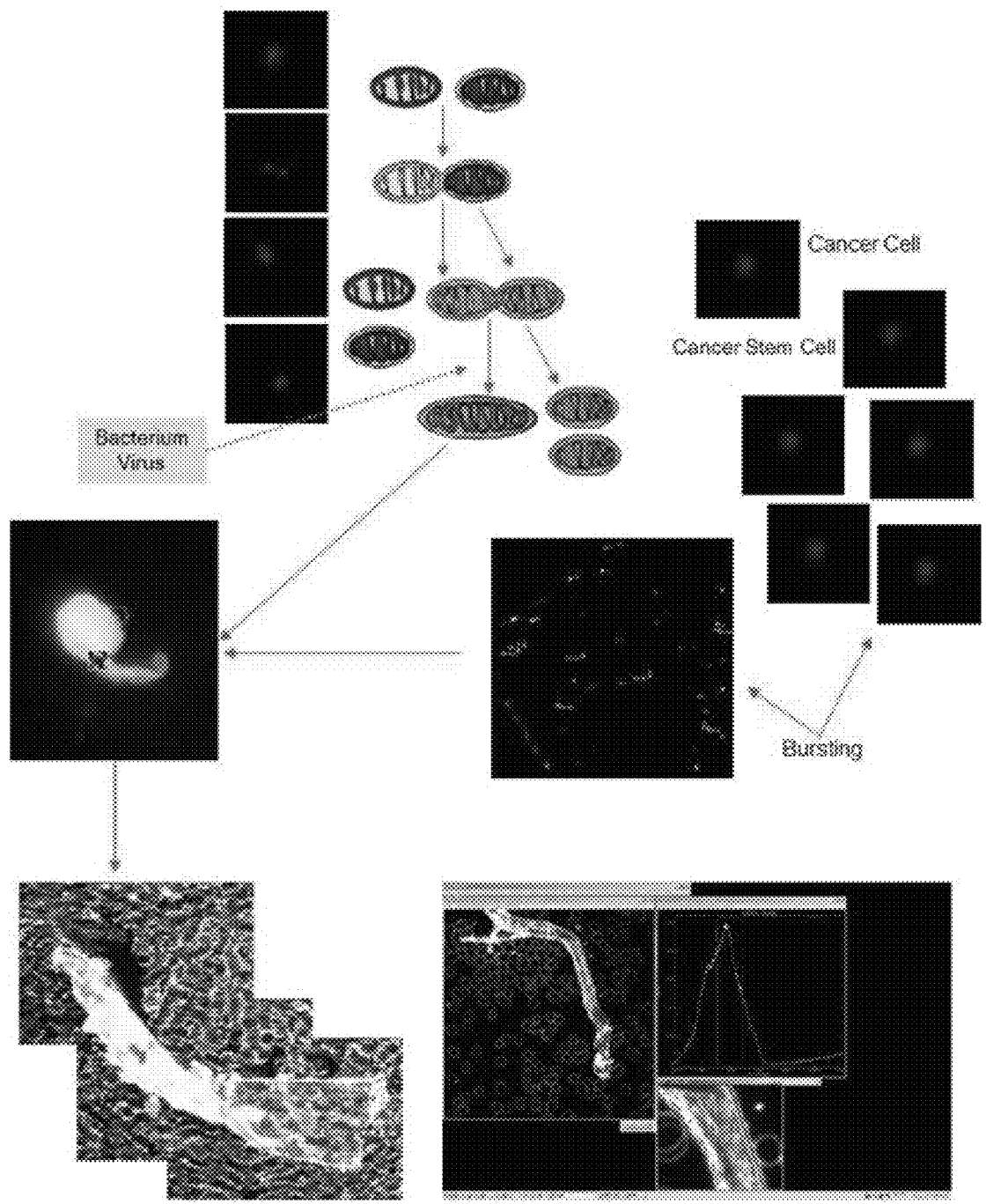
FIG. 9 shows the life cycling and characteristics of mutated luterial.
Figure 10B:
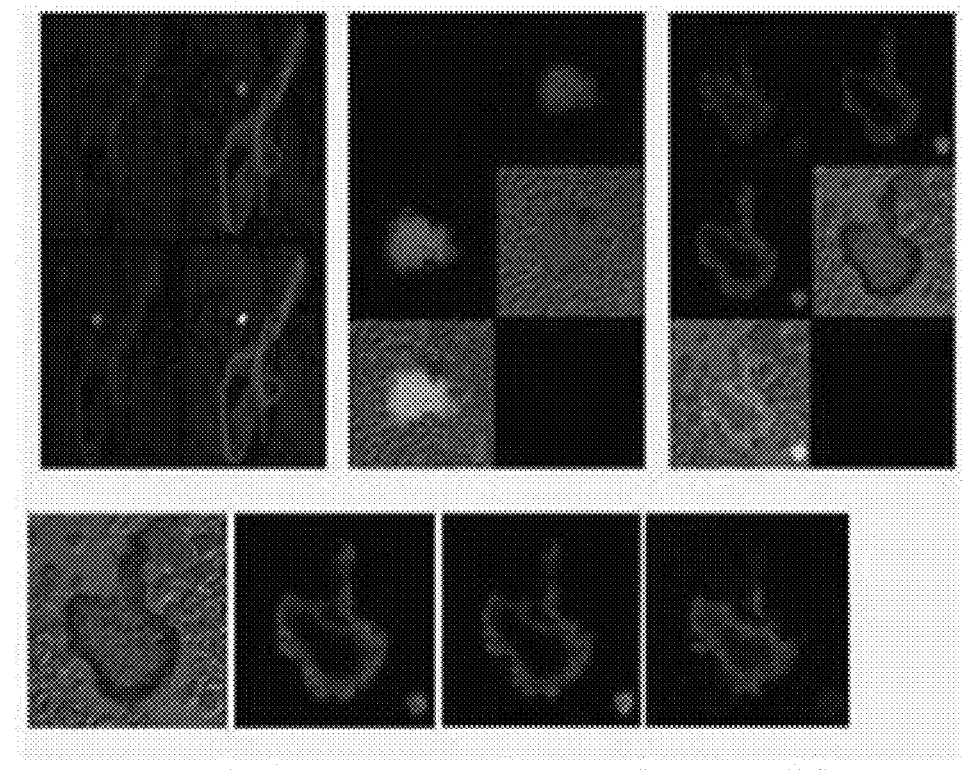
Figure 11:
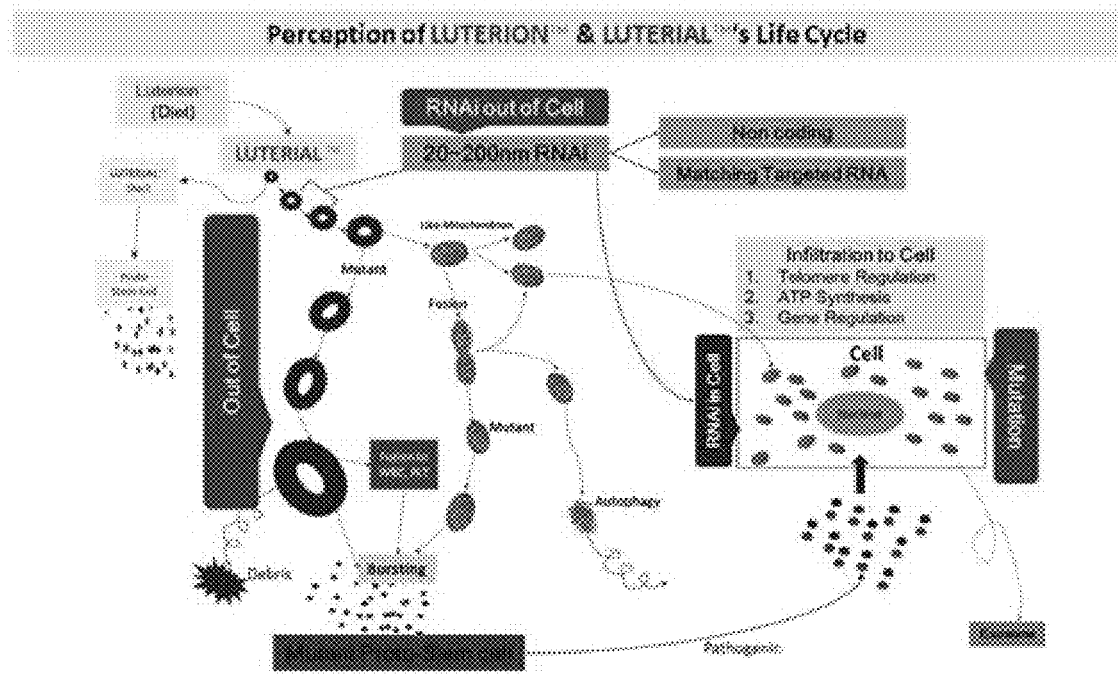
FIG. 11 shows the life cycle of luterial.

Unlike exosomes and microvesicles, luterials were adherent and mobile and underwent fusion or fission events. It was found that mutant luterial did burst under certain conditions, had sternness after bursting, and could be present inside or outside cells (FIG. 8, FIG. 9 and FIG. 11). Specifically, luterials could survive outside the cells and this makes for luterials be different from cellular mitochondria, which are present inside cells.

(4) ATP Production

Figure 18:
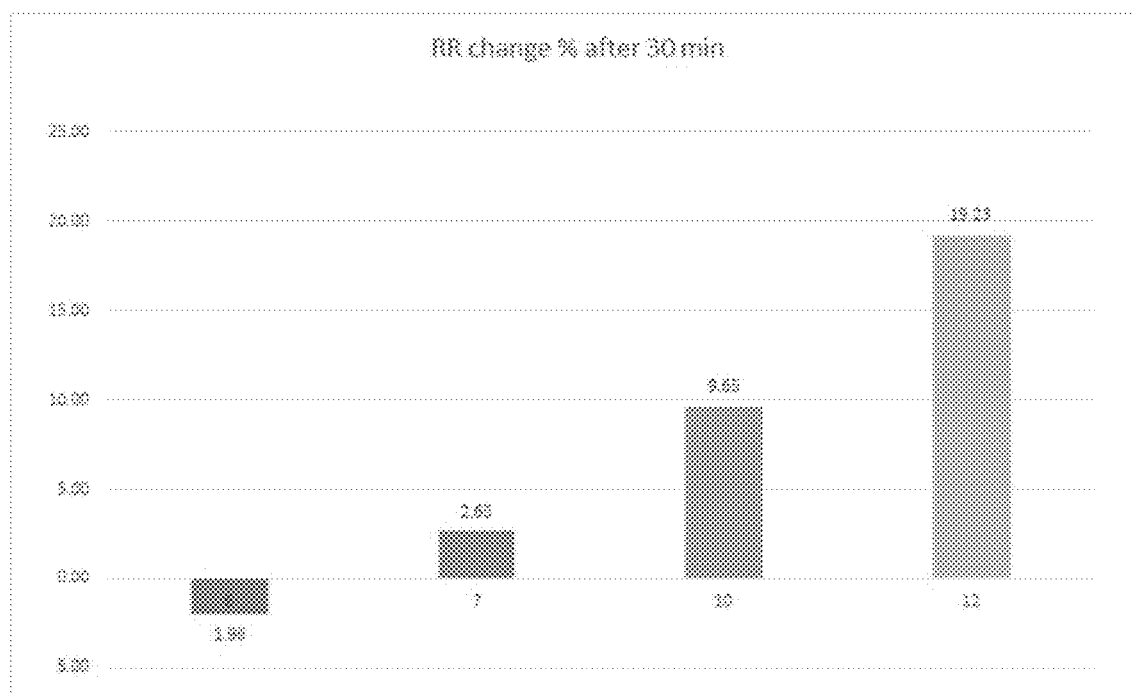
FIG. 18 shows the results of measuring ATP content in media having different luterials added thereto by use of a luciferin-luciferase reaction and a luminometer (SSH: three-star ring; SSF: fisetin; 12 h: activated at 37° C. for 12 hours before an experiment).

ATP production in luterial having a size of 200-400 nm was demonstrated using luciferin-luciferase reaction and a luminometer. A media containing luterial showed an increase in ATP concentration compared to a media without luterial, indicating that luterial has the ability to produce ATP. SSH and SSF were further added to the media and their effects on ATP production by luterial were examined. A mediacontaining SSF induced higher ATP production by luterialcompared to a mediawith SSH, thus finding a medium mix that is capable of efficiently increasing the ATP production by luterial (FIG. 18).

(5) Content of Nucleic Acids

It was found by DAPI and acridine orange (AO) staining that luterial contains not only RNA, but also DNA. Specifically, AO is known to stain RNA with orange AO at an excitation wavelength of 460 nm and an emission wavelength of 650 nm, and DNA with green at an excitation wavelength of 502 nm and an emission wavelength of 525 nm. DNA was extracted and subjected to Atomic Force Microscope and its image was processed under NanoScope analysis software. The result indicated that the height of DNA contained within luterials is approximately 5 nm.

DAPI is known to positively stain for DNA. Luterial according to the present invention was confirmed to contain RNA and DNA using the staining test as described above (FIG. 5 and FIG. 6). RNA in luterial were further isolated and purified using an extraction kit, and then subjected to agarose gel electrophoresis after qRT-PCR against human GAPDH gene transcripts. It was found that the expression level of human GAPDH gene changed depending on the size of the luterial (FIG. 2H, FIGS. 16A-16B and FIG. 17).

(6) 16S rRNA Sequencing

The gDNA of luterial was extracted using a FastDNA SPIN Kit (MP Biomedicals, Cat 6560-200), and then the 16S rRNA gene was amplified using the primers shown in Tables 1 and 2 below.

In addition, the 1461 amplified gene fragments were analyzed for their homology using GenBank database (NCBI database). As a result, luterials derived from blood and sperm showed 16S rRNA sequences having homology with those of genes derived from β-proteobacteria, γ-proteobacteria, Acidobacteria, Cyanobacteria, Actinobacteria, Firmicutes and eukaryotes, and showed integrative characteristics corresponding to those of an intermediary between a prokaryote and an eukaryote (FIGS. 24A through 24D and FIGS. 25A through 25D).

It was observed that, in an optimal condition (blood pH: 7.2-7.4), blood-derived luterial showed homology with genes derived from β-proteobacteria and γ-proteobacteria (FIGS. 24A through 24D) and had a size of 20-800 nm.

In normal conditions, sperm-derived luterial showed homology with genes derived from β-Proteobacteria and γ-Proteobacteria, Bacteroidetes and Chordata.

On the contrary, in an acidic condition, not only genes derived from β-proteobacteria and γ-proteobacteria as in normal conditions, but also other diverse bacteria-derived genes and eukaryote-derived genes were expressed. The luterial mainly expressed the 16S rRNA characteristics of Streptophyta and planctomy (FIGS. 25A through 25D) and grew to a size of 400-2000 nm.

TABLE 3

Forward primers

| Taxon | Name | Sequence(Adaptor-key-linker-target sequence) | SEQ ID NOs: |
|---|---|---|---|
| Bacteria | B16S-F | 5'-CCTATCCCCTGTGTGCCTTGGCAGTC-TCAG-AC-GAGTTTGATCMTGGCTCAG-3' | 1 |
| Bifidobacterium | Bif16S-F | 5'-CCTATCCCCTGTGTGCCTTGGCAGTC-TCAG-AC-GGGTTCGATTCTGGCTCAG-3' | 2 |

TABLE 4

Reverse primers

| Taxon | Name | Sequence(Adaptor-key-linker-target sequence) | SEQ ID NO: |
|---|---|---|---|
| Bacteria | B16-7-4 | 5'-CCATCTCATCCCTGCGTGTCTCCGAC-TCAG-AGAGCTG-AC-WTTACCGCGGCTGCTGG-3' | 3 |
| Bacteria | B16-7-7 | 5'-CCATCTCATCCCTGCGTGTCTCCGAC-TCAG-TCAGATG-AC-WTTACCGCGGCTGCTGG-3' | 4 |
| Bacteria | B16-7-8 | 5'-CCATCTCATCCCTGCGTGTCTCCGAC-TCAG-CGATGAG-AC-WTTACCGCGGCTGCTGG-3' | 5 |
| Bacteria | B16-7-12 | 5'-CCATCTCATCCCTGCGTGTCTCCGAC-TCAG-TCTGCAG-AC-WTTACCGCGGCTGCTGG-3' | 6 |
| Bacteria | B16-7-13 | 5'-CCATCTCATCCCTGCGTGTCTCCGAC-TCAG-AGCGATG-AC-WTTACCGCGGCTGCTGG-3' | 7 |
| Bacteria | B16-8-3 | 5'-CCATCTCATCCCTGCGTGTCTCCGAC-TCAG-ATGCTGAG-AC-WTTACCGCGGCTGCTGG-3' | 8 |
| Bacteria | B16-8-4 | 5'-CCATCTCATCCCTGCGTGTCTCCGAC-TCAG-TACAGCAG-AC-WTTACCGCGGCTGCTGG-3' | 9 |
| Bacteria | B16-8-18 | 5'-CCATCTCATCCCTGCGTGTCTCCGAC-TCAG-ATCGTGTG-AC-WTTACCGCGGCTGCTGG-3' | 10 |
| Bacteria | B16-8-21 | 5'-CCATCTCATCCCTGCGTGTCTCCGAC-TCAG-CTACACAG-AC-WTTACCGCGGCTGCTGG-3' | 11 |
| Bacteria | B16-9-4 | 5'-CCATCTCATCCCTGCGTGTCTCCGAC-TCAG-CGTGTACTG-AC-WTTACCGCGGCTGCTGG-3' | 12 |
| Bacteria | B16-9-5 | 5'-CCATCTCATCCCTGCGTGTCTCCGAC-TCAG-CTGTCTACG-AC-WTTACCGCGGCTGCTGG-3' | 13 |
| Bacteria | B16-9-8 | 5'-CCATCTCATCCCTGCGTGTCTCCGAC-TCAG-AGTCACTAG-AC-WTTACCGCGGCTGCTGG-3' | 14 |
| Bacteria | B16-9-12 | 5'-CCATCTCATCCCTGCGTGTCTCCGAC-TCAG-AGCTCACTG-AC-WTTACCGCGGCTGCTGG-3' | 15 |
| Bacteria | B16-10-6 | 5'-CCATCTCATCCCTGCGTGTCTCCGAC-TCAG-ATCACGTGCG-AC-WTTACCGCGGCTGCTGG-3' | 16 |
| Bacteria | B16-10-7 | 5'-CCATCTCATCCCTGCGTGTCTCCGAC-TCAG-ATAGCTCTCG-AC-WTTACCGCGGCTGCTGG-3' | 17 |

TABLE 4-continued

Reverse primers

| Taxon | Name | Sequence(Adaptor-key-linker-target sequence) | SEQ ID NO: |
|---|---|---|---|
| Bacteria | B16-10-8 | 5'-CCATCTCATCCCTGCGTGTCTCCGAC-TCAG-AGTGAGCTCG-AC-WTTACCGCGGCTGCTGG-3' | 18 |
| Bacteria | B16-10-9 | 5'-CCATCTCATCCCTGCGTGTCTCCGAC-TCAG-AGTCTGACTG-AC-WTTACCGCGGCTGCTGG-3' | 19 |
| Bacteria | B16-11-1 | 5'-CCATCTCATCCCTGCGTGTCTCCGAC-TCAG-TCATATACGCG-AC-WTTACCGCGGCTGCTGG-3' | 20 |
| Bacteria | B16-11-2 | 5'-CCATCTCATCCCTGCGTGTCTCCGAC-TCAG-TAGATAGTGCG-AC-WTTACCGCGGCTGCTGG-3' | 21 |
| Bacteria | B16-11-3 | 5'-CCATCTCATCCCTGCGTGTCTCCGAC-TCAG-ACGTCTCTACG-AC-WTTACCGCGGCTGCTGG-3' | 22 |
| Bacteria | B16-11-4 | 5'-CCATCTCATCCCTGCGTGTCTCCGAC-TCAG-CTAGAGACACT-AC-WTTACCGCGGCTGCTGG-3' | 23 |

(7) Differences from Exosomes and Mitochondria

Table 5 below summarizes the differences of luterials from exosomes and mitochondria.

TABLE 5

| No. | Category | Exosomes | Luterials | Mitochondria |
|---|---|---|---|---|
| 1 | Size | 20~120 nm | 20~800 nm | 400~1,000 nm |
| 2 | Fluorescence | (CD63antibody)GFP+ | (CD63antibody)GFP− | (CD63antibody)GFP− |
| 3 | Fluorescence | Mitotracker Red− | Mitotracker Red+ | Mitotracker Red+ |
| 4 | Fluorescence | Janus Green B− | Janus Green B+ | Janus Green B+ |
| 5 | Fluorescence | Rhodamine 123− | Rhodamine 123+ | Rhodamine 123+ |
| 6 | Mobility | − | 13-25 μm/sec | − |
| 7 | Growth in Culture | − | + | − |
| 8 | Natural Growth | − | + | − |
| 9 | ATP Synthesis | − | + | + |
| 10 | Auto-fluorescence | − | + | N/A |
| 11 | Fusion | + | + | + |
| 12 | Kiss-and-run (Fission and Fusion) | − | + | + |
| 13 | Sequencing | 18SrRNA 28S rRNA | 16SrRNA (GammaProtebacteria Beta Proteobacteria Bacteroidetes | 16srRNA Alpha Proteobacteria |
| 14 | Habitat | Out of cell | In-and-out of Cell | In cell |

Figure 19:
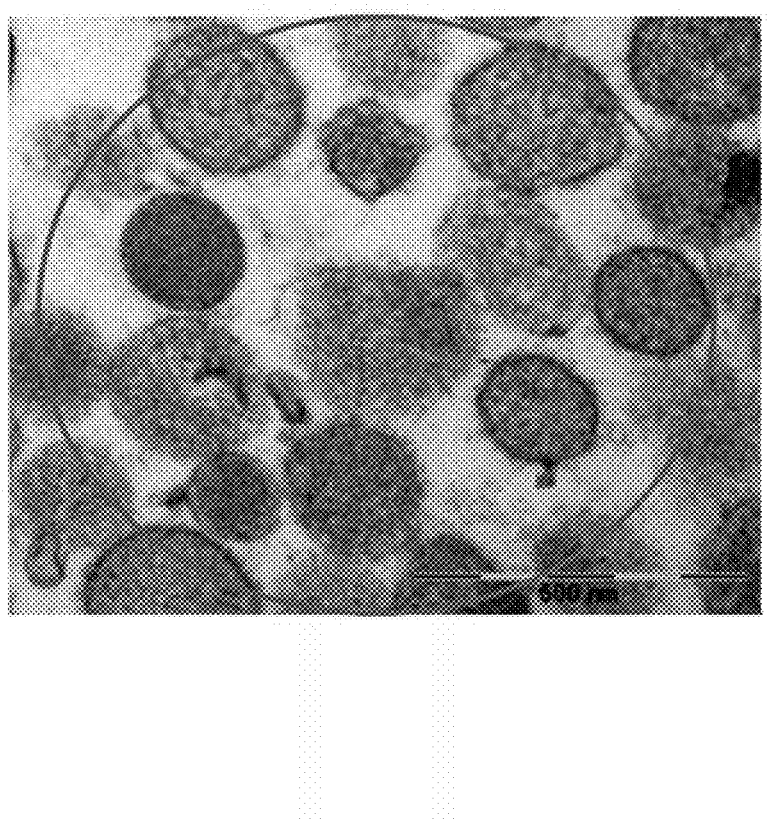
FIG. 19 is a photograph showing a difference between luterial and exosome.

Luterials have an average size of 200-800 nm, which is smaller than that of mitochondria (400-1,000 nm) and greater than that of exosomes (20-120 nm), and exosomes have unclear membranes and a relatively light internal color, whereas luterials have distinct membranes or a packed internal structure (FIG. 19). In addition, luterials have a morphology completely different from those of exosomes and microvesicles (FIG. 20).

In fluorescent staining, luterials unlike exosomes show a reaction similar to that of mitochondria. Luterials are present inside and outside of cells while exosomes are present outside of cells only. Luterials can be supplied by taking foods, whereas mitochondria are intracellular substances that cannot be provided by intake of foods.

Figure 31:
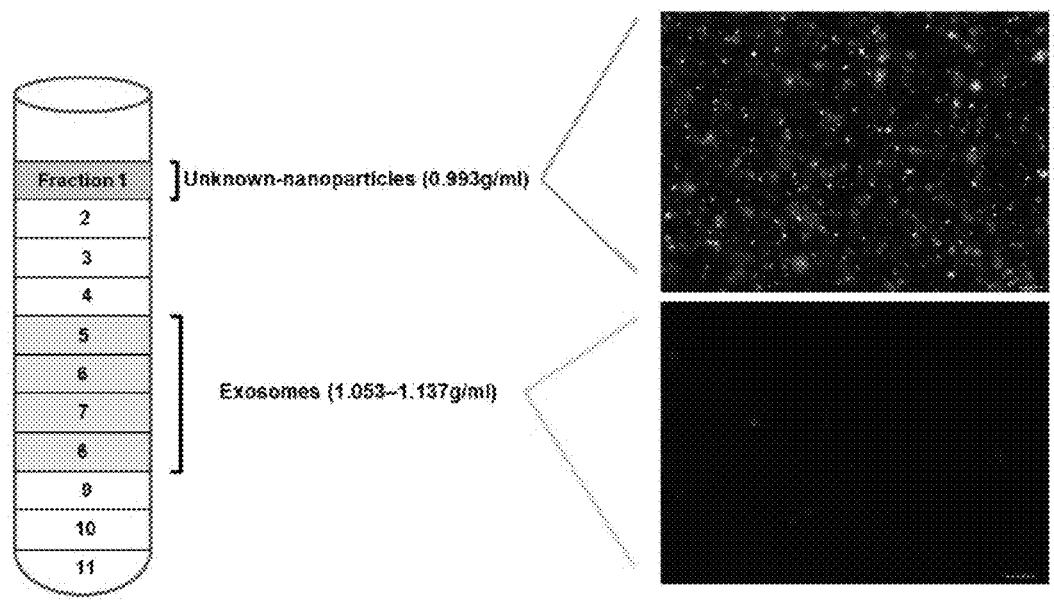
FIG. 31 shows different fractions of luterial and exosomes according to the sucrose gradient assay, when collecting luterial by using sucrose density gradient (unknown-nanoparticle=luterial).

The human blood plasma filtered with 800 nm filter was spun on a sucrose gradient to identify the fraction that contained the motile luterials when viewed under the dark-field microscope. The Fraction 1 (0.993 g/ml) collected from the top most layer where LDL/HDL was found contained most of the luterials. In the rest of the fractions including the Fractions 5~8 (1.053~1.137 g/ml) where exosomes are reported to be found, the luterials were extremely scarce as compared to Fraction 1 (FIG. 31). These separations under the sucrose gradient suggest that luterials are unique from other known EVs in that their density is much less than that of EVs that are known to date.

To further verify that luterials are different from exosomes, Fraction 1 (luterials) and Fraction 5 (exosome) samples were subjected to Western blot and examined the presence of the known exosome markers. The exosome markers, CD63, CD9, TSG101 and Flotillin-1 appeared in the exosome fraction, but none in the fraction containing luterials, further confirming the distinction of luterials from exosomes. Additionally, both the supernatant and pellet fractions of the blood samples after ultracentrifugation at 140,000 g were subjected to immunogold labelling with anti-CD63.

Figure 30:
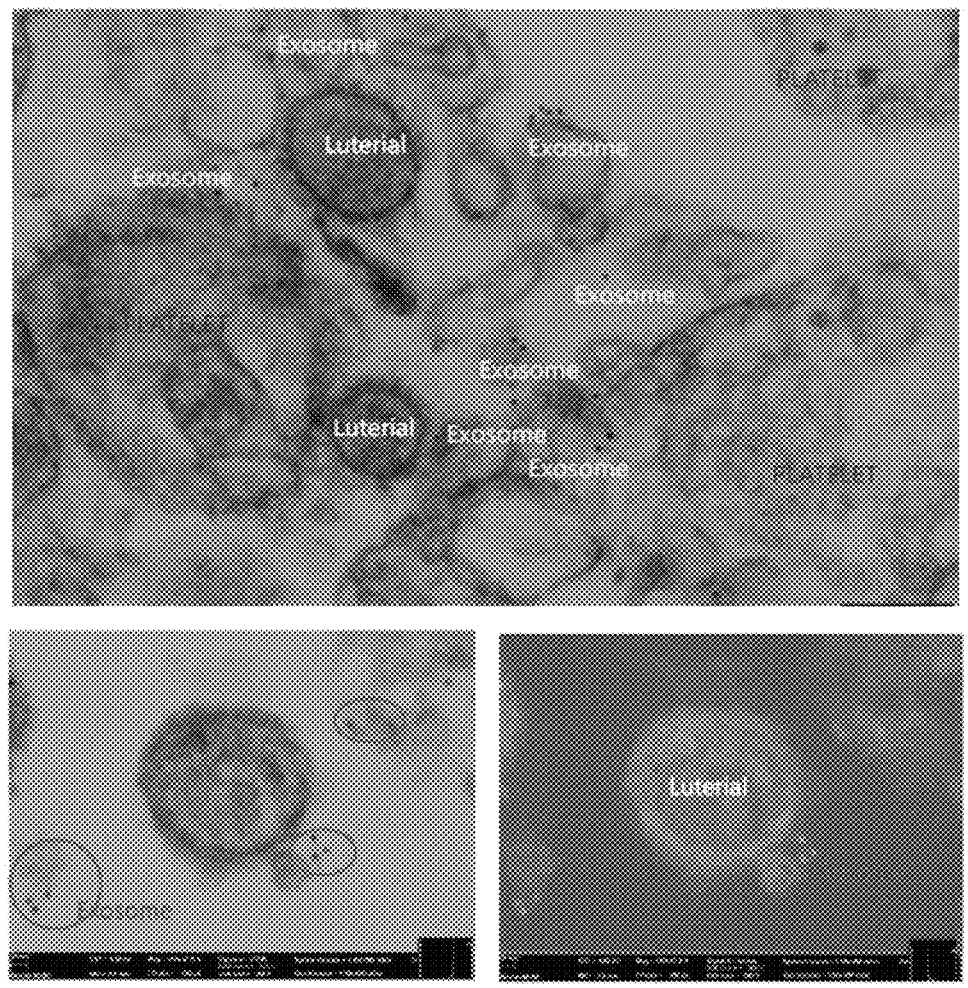
FIG. 30 shows results of comparing exosome expressing CD63 marker with luterial, in which CD63 marker is not expressed.
Figure 32:
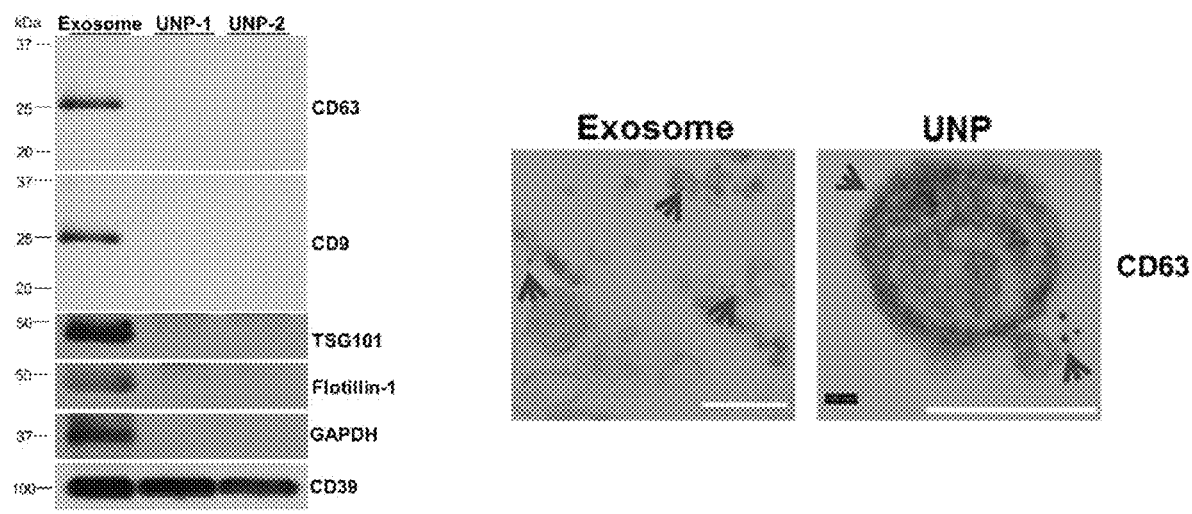
FIG. 32 shows results of confirming the expression of luterial specific marker characteristics in fraction 1 including luterial isolated through sucrose gradient assay and fractions 5-8 including exosome (UNP=luterial).
Figure 33:
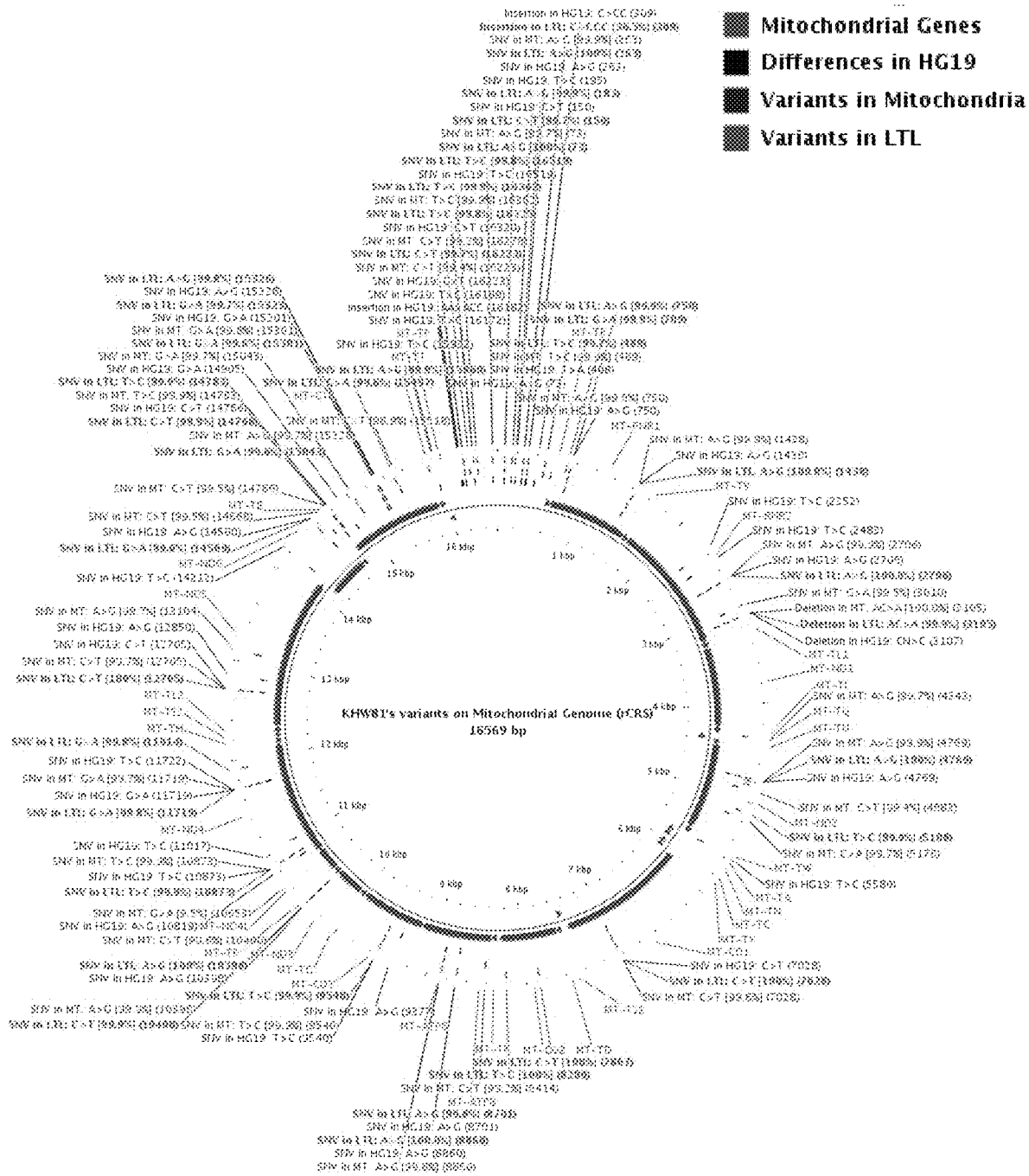
FIGS. 33 to 42 show capillary sequencing results indicating sequence of luterial and point variations in luterial specific bases, which are distinctive from sequences of mitochondria.
Figure 34:
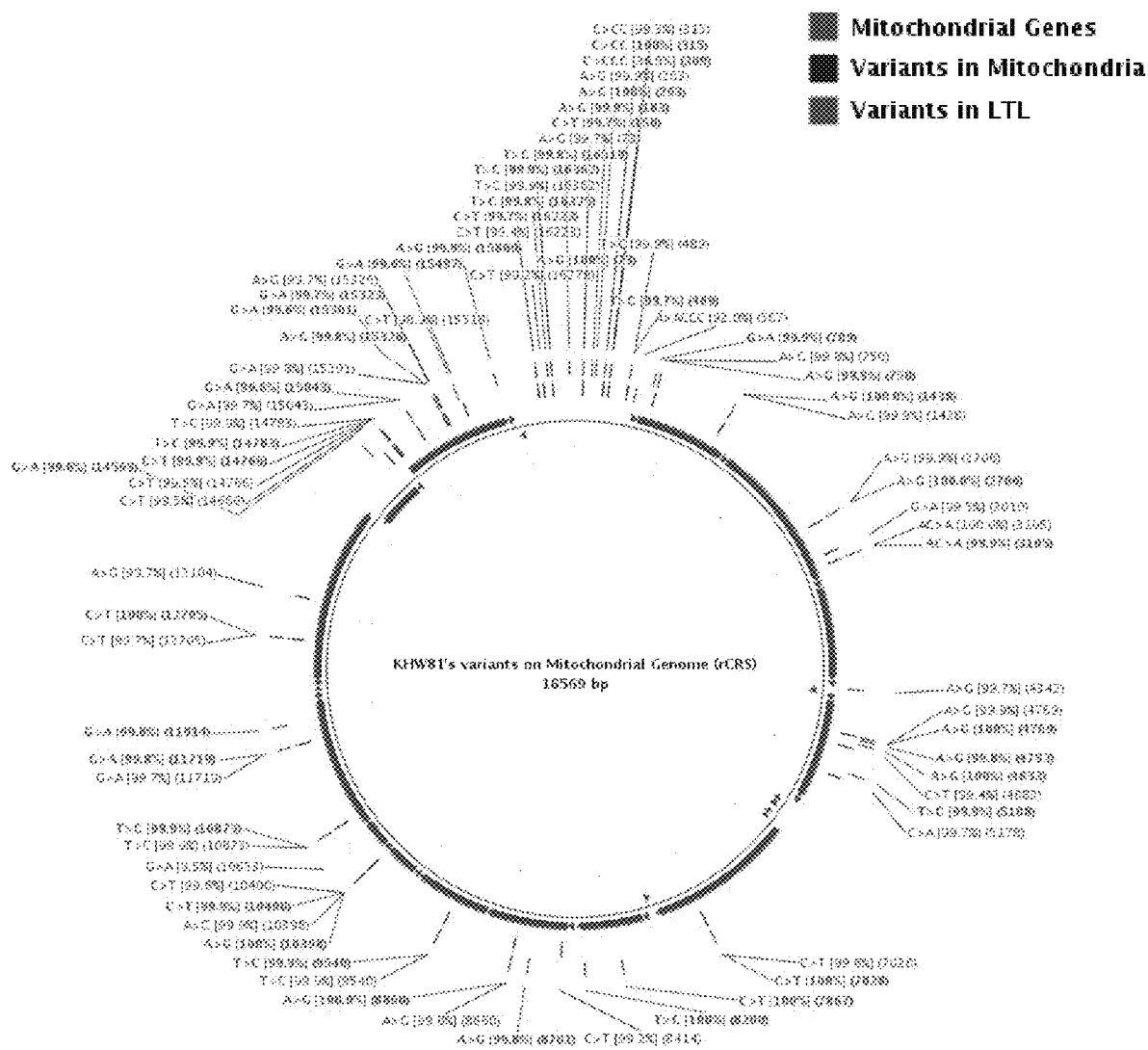
Figure 35:
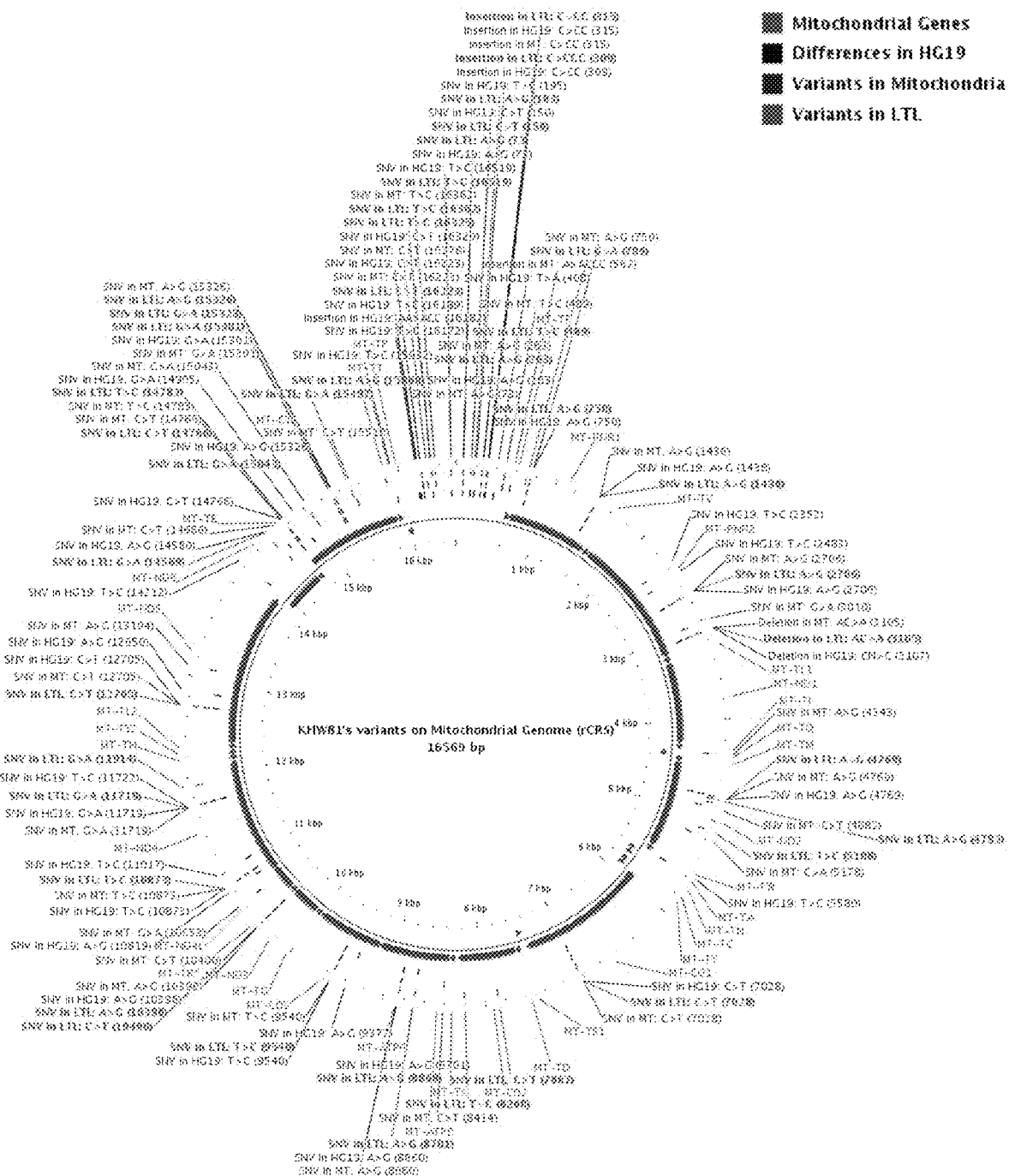
Figure 36:
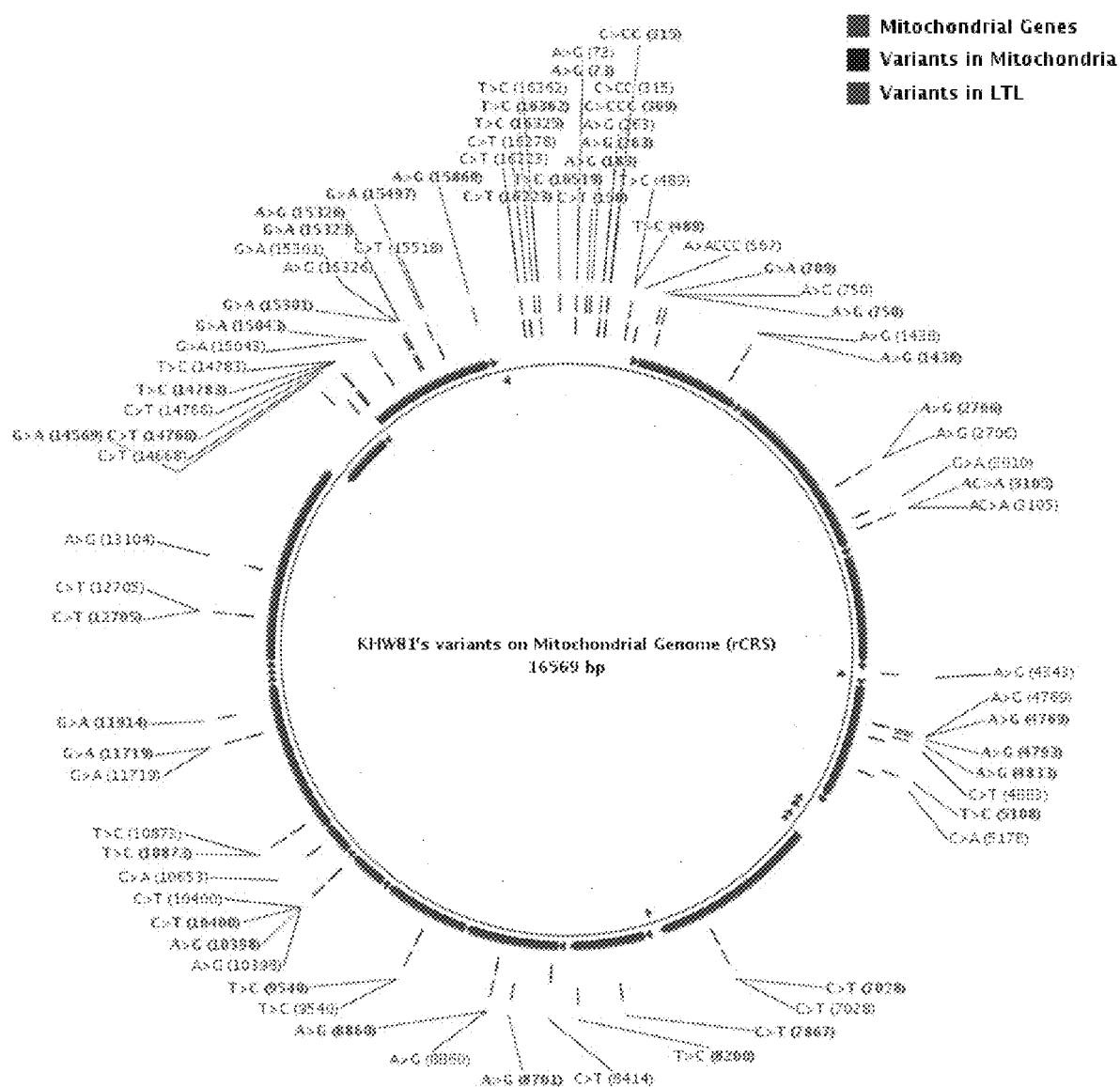
Figure 37:
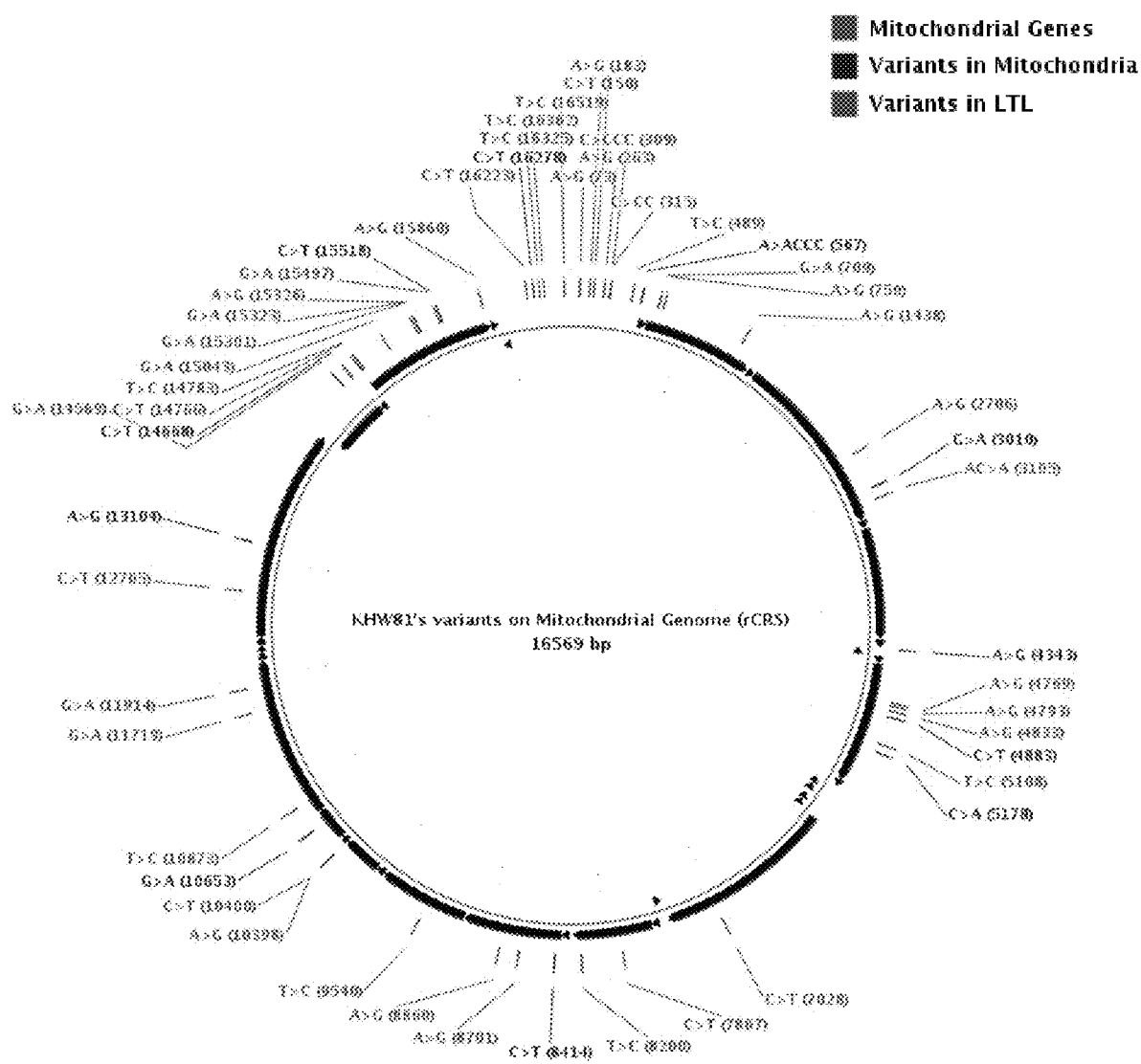
Figure 38:
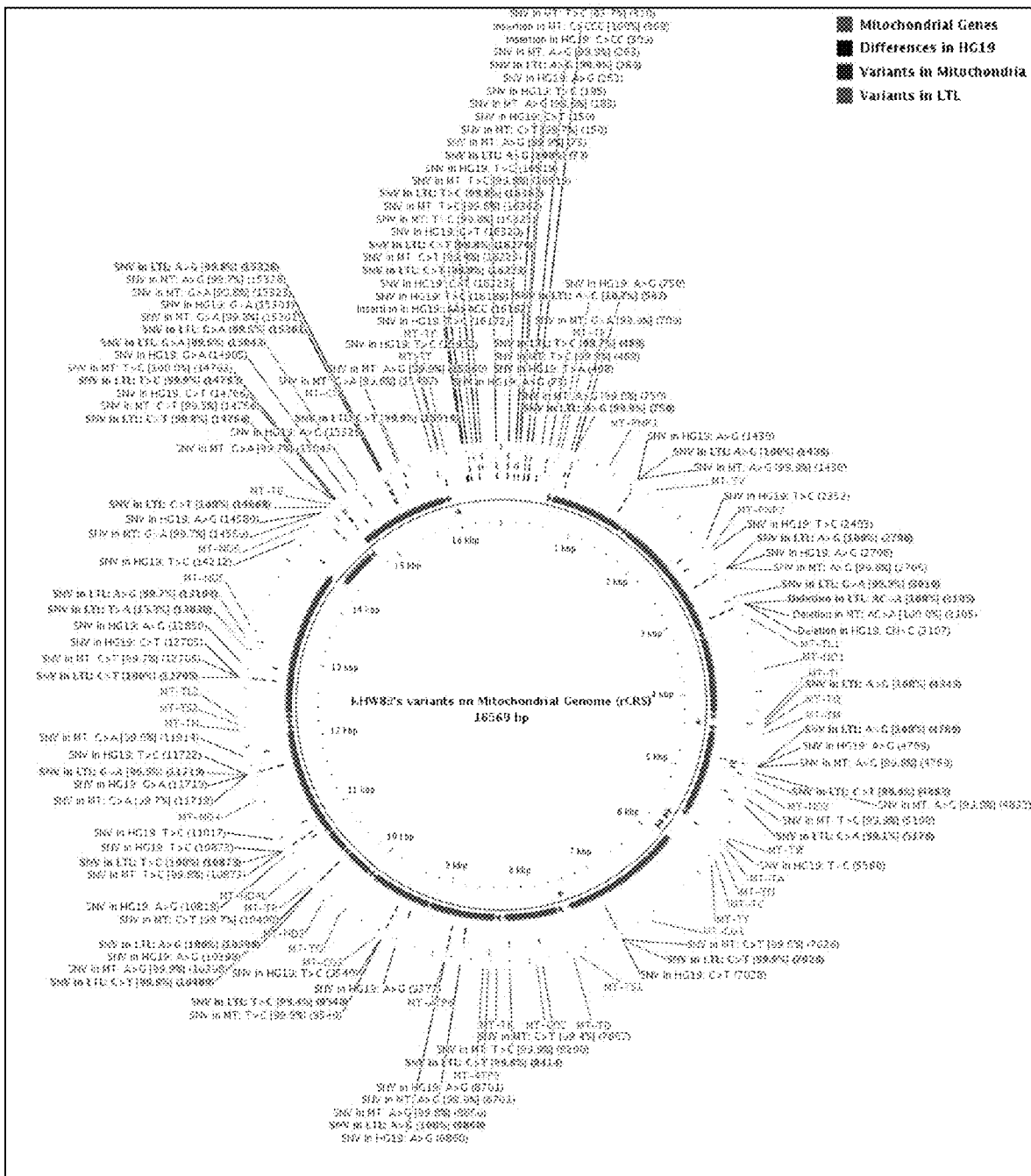
Figure 39:
Figure 40:
Figure 41:
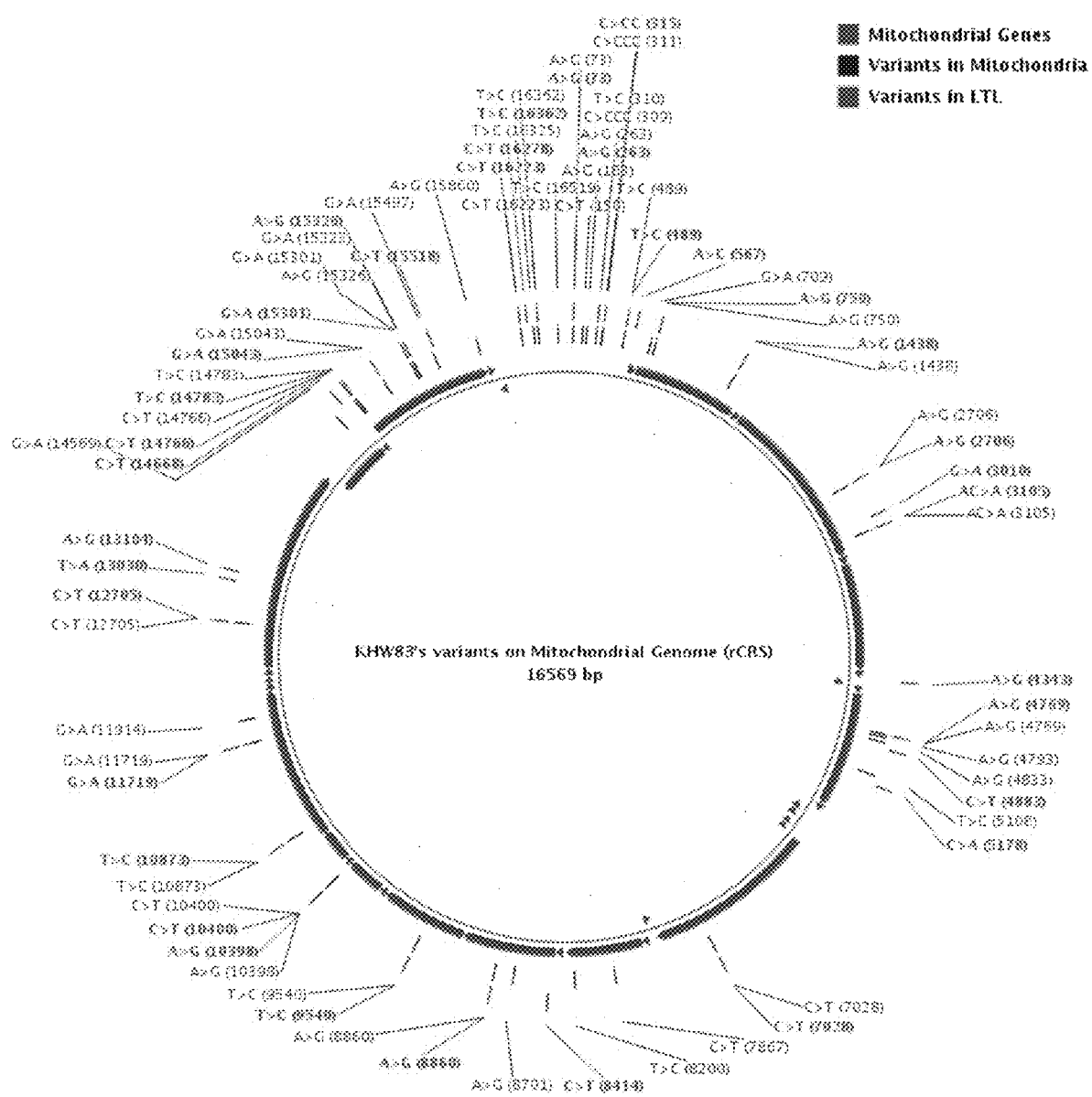
Figure 42:
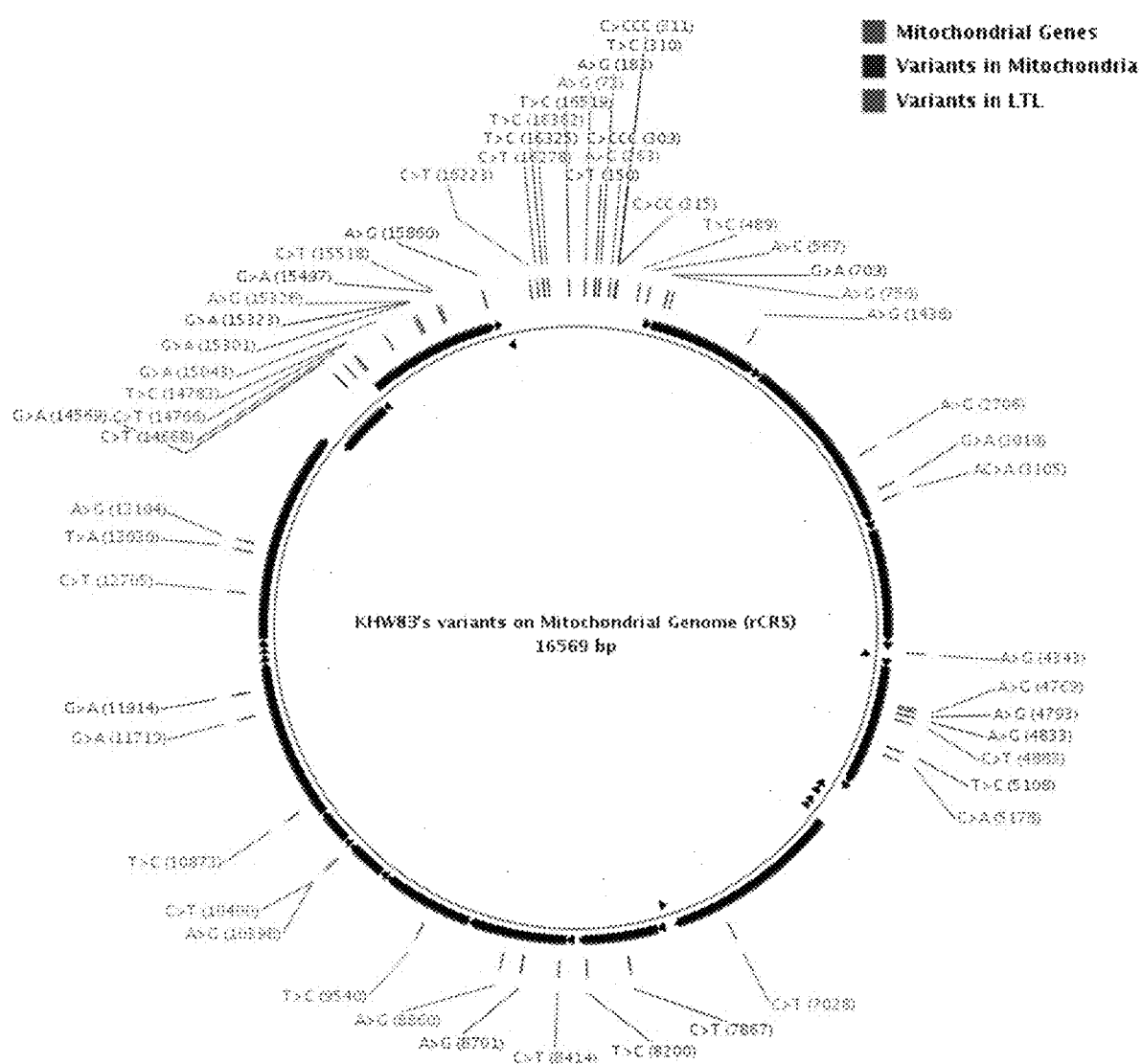

While a positive labelling of CD63 was detected with the pelleted sample containing exosomes, no labelling was detected with the supernatant portion containing the luterials (FIG. 30 and FIG. 32). The motile luterials appeared to undergo fission, an event that resembles the feature observed in mitochondria. Fissional split of a single nanoparticle was observed in multiple modes of microscopy, including the light field microscope, SEM imaging and NTA capture. Furthermore, the "Kiss-and-Run"-like motion, a well-described behavior of mitochondria seemed to duplicate with luterials, as detected under the instant capturing of two "kissing" nanoparticles using SEM, STEM and dark field microscope.

While mitochondria and luterials manifested the similar motional characteristics, their morphological features seemed to deviate from each other. The high resolution STEM image of the luterials revealed that it lacked the cristae structure and defined double-layered membranes that were clearly evident in mitochondria.

Unlike exosomes and mitochondria, luterials are mobile, and can grow naturally, the growth thereof can be maintained by culture, and show autofluorescence. Furthermore, luterials, exosomes and mitochondria all undergo fusion events, but in exosomes, kiss-and-run motion and ATP production are absent. Moreover, exosomes are present outside the cells and mitochondria are present inside the cells, whereas luterials can be present inside or outside the cells (FIG. 11).

All three mitochondrion-specific dyes such as MitoTracker-RED, Rhodamine 123 and Janus Green B positively stained luterials, but not exosomes. A well-known mitochondrion-specific marker anti-VDAC showed a positive binding to the luterials, but not to exosomes. Platelet mitochondria was used as a positive control, which exhibited the positive staining with anti-VDAC. Also, fluorescent staining against an ATP-related protein CD39 which was confirmed to be present in luterials by the Western blot.

The DNA extracts of luterials were further subjected to qRT-PCR using seven known probes for ATP-related proteins, ND1 (OXPHOS complex I), CO1 (OXPHOS complex IV), ATP6 (OXPHOS complex V), ATP8 (OXPHOS complex V), RNR1, RNR2 and 7S. The luterials expressed transcripts for all seven genes comparable to those expressed in mitochondria isolated from MRC-5 lung fibroblast cell lines.

Luterials express at least one marker selected from the group consisting of CD14, CD24, CD29, CD34, CD39, CD44, CD45 (CD45RA/CD45RO), CD73, CD90, CD105, CD133, CD173, CD326, CD332, and OCT4. These markers are not expressed in mitochondria, and markers such as CD63 and/or CD81, which are not expressed in luterials, are expressed in exosome and luterial specific markers are not expressed in exosome. These differences in expression of markers might be a distinct feature that separated these motile luterials from other known EVs like exosomes or motochondria. The results of 16S rRNA sequencing indicated that mitochondria showed homology with α-proteobacteria, whereas luterials showed homology with γ-proteobacteria, β-proteobacteria, Bacteroidetes, Firmicutes and eukaryotes.

The whole genome sequencing for mtDNA of the platelets and DNA of luterials obtained from two other donors was performed using Next Generation Sequencing followed by BLAST search against NCBI mitochondria database. DNA sequence from platelet mitochondria and luterials shared >99% homology, yet with the base variation evident in both donors between cellular mitochondria and luterials. A common point variation in 16 bases of the luterials in comparison to rCRS among all three donors of the capillary and whole genome sequencing experiments. Those common point variations in 16 bases may be the potential markers for the luterials. Luterial specific point variations compared to those of mitochondria are in positions of 150, 183, 309, 4793, 4833, 5108, 7867, 8200, 8701, 11914, 14569, 15323, 15497, 15860, 16325 and 16519 of sequence as set forth in SEQ ID NO:24. Luterial specific point variations at 16 positions might be described as follows:

T in position 150,
G in position 183,
CC or CCC in position 309,
G in position 4793,
G in position 4833,
CC or CCC in position 5108,
T in position 7867,
C in position 8200,
G in position 8701,
A in position 11914,
A in position 14569,
A in position 15323,
A in position 15497,
G in position 15860,
C in position 16325, and
C in position 16519 of sequence as set forth in SEQ ID NO:24.

| Position | Point Variations | |
| --- | --- | --- |
| | Mitochondria | Luterial |
| 150 | C | T |
| 183 | A | G |
| 309 | C | CC, CCC |
| 4793 | A | G |
| 4833 | A | G |
| 5108 | T | CC, CCC |
| 7867 | C | T |
| 8200 | T | C |
| 8701 | A | G |
| 11914 | G | A |
| 14569 | G | A |
| 15323 | G | A |
| 15497 | G | A |
| 15860 | A | G |
| 16325 | T | C |
| 16519 | T | C |

In another aspect, the present invention is focused on the body fluid-derived luterial having one or more of the following characteristics:

(a) it shows a positive staining with Janus green B, Acridine Orange and Rhodamine 123 in a fluorescence test;

(b) in an optimal environment (pH 7.2-7.4), it expresses genes homologous to beta-proteobacteria and gamma-proteobacteria, and has a size of 30-800 nm;

(c) in an acidic environment, it expresses genes homologous to not only beta-proteobacteria and gamma-proteobacteria, but also eukaryote Streptophyta, and grows to a size of 400 nm-2000 nm or more;

(d) it is involved in ATP production in normal conditions;

(e) it is a cell or cell-like structure completely different from mitochondria or exosomes; (0 it is circular or oval in shape in a normal condition, and patient-derived luterial has a size (long axis diameter: 800 nm or more) greater than that of normal luterial and is mutated to form mutant luterial having a non-uniform morphology;

(g) it has a double-layered, multiple layered ring-like membrane structure or a mixed form of double-layered and multiple layered membrane structure, and is adherent;

(h) it can be present inside or outside cells;

(i) it is mobile and undergoes fusion and/or fission events;

(j) mutant luterial bursts in a certain condition and has sternness after bursting;

(k) it has a function of regulating p53 gene and telomeres, having a distinct feature to activate telomerase activity in normal cell and inhibit telomerase activity in cancer cell;

(l) express at least one protein selected from the group consisting of CD14, CD24, CD29, CD34, CD39, CD44, CD45 (CD45RA/CD45RO), CD73, CD90, CD105, CD133, CD173, CD326, CD332, OCT4, ND1 (OXPHOS complex I), CO1 (OXPHOS complex IV), ATP6 (OXPHOS complex V), ATP8 (OXPHOS complex V), RNR1, RNR2 and 7S; and (m) found in the fraction with 0.99 or less density in 15-60% sucrose density gradient Meanwhile, the size (diameter), area, morphology and nano-tracking speed of luterial differ depending on the presence or absence of disease in an individual, and thus one or more of the above-described characteristics make it possible to diagnose disease or predict disease prognosis. This can be seen from the fact that luterial derived from a healthy person having no disease and luterial derived from a person having disease have different sizes, morphologies, nano tracking speeds, etc.

Normal luterials in healthy persons merely form double spores undergoing fission, but luterials (mutant luterials) in patients with chronic disease or cancer have characteristics in that they fuse or coagulate with one another or burst to adhere to cells such as erythrocytes or cancer cells, thereby changing their morphology and size abnormally (FIG. 8, FIG. 9, and FIGS. 10A-10B). Mutant luterials are highly adherent, and thus the fusion thereof is accelerated by the above-described cycle to increase their size to about 600-800 nm or more, and any of such mutant luterials may also have a size of 200 µm (200,000 nm) or more. The present inventors found that the morphology of luterials is consistent depending on the kind or progress of cancer, and the content of this finding was filed for a patent (Korean Patent Application No. 10-2013-0082060).

Thus, it is possible to diagnose disease or predict disease prognosis by observing the morphological or biochemical characteristics of luterials, indicating that luterials can be used in unlimited applications.

Luterials have a normal form, a flagellum form, a mass form, a rod form, or a combination form. Herein, the normal form may be a form that does not undergo additional modification such as fusion or bursting, with a long axis diameter-to-short axis diameter ratio of 1:1-3:1. The luterials can show a shape close to a circular shape. They appear as small spots in microscopic observation.

The flagellum form may be a form that results from the modification or fusion of luterials to have flagella-like structure attached outside. The present inventors found that the percentage of the flagellum form dramatically increased as cancer progresses to terminal cancer and that this flagellum form luterials were observed in 99.1% of the patients diagnosed as stage 4 cancer (Korean Patent Application No. 2013-0082060). If the percentage of the flagellum-form luterial reaches 80-100%, it would work as a tumor marker to indicate a terminal stage cancer. The survival period of such patients is about 1-4 months, and particularly, patients dominated with flagellum form luterials cannot survive for a long period.

The mass form (M shape) is a form that was changed from the normal form due to the bursting or fusion of luterials. It is an irregular bulky shape whose long axis diameter-to-short axis diameter ratio is not great. Preferably, it may have a long axis diameter-to-short axis diameter ratio of 3:1-5:1. Various forms of the mass form are observed.

The rod form (R shape) refers to a form resulting from the bursting, modification or fusion of luterials. It has a long axis diameter-to-short axis diameter ratio greater than that of the mass shape. Preferably, it may have a long axis diameter-to-short axis diameter ratio of 5:1-12:1. It includes a rod 1 form consisted of circular or oval single chains; and a rod 2 form consisted of two or more single chains bonded to one or another. The rod 1 form refers to the single luterial that has grown to a rod shape. It may result from the bursting and/or mutation. The rod 2 form refers to a rod shaped luterial formed from fusion of two or more luterials. It may result from one or more of bursting, mutation and fusion. The flagellum form may be included in a broad sense in the scope of the rod form, but it would be different from the rod form in that it has a flagellum-like structure. Thus, luterial form should be first determined whether it is of the rod form and then depending on the presence of the flagellum-like structure it should be further categorized into the flagellum form.

The combination form may be a combination of the rod shape and the mass shape. It may mean that a portion of a single micro particulate matter has the rod shape and the other portion thereof has the mass shape.

The rod form may be one selected from the group consisting of: a rod 1 form consisted of a single circular or oval shape; and a rod 2 form consisted of two or more single chains bonded to one another. The combination form may be a combination of the rod shape and the mass shape.

As described above, the morphology of luterials in vivo changes depending on the development and progress of disease, and thus it is possible to diagnose disease or predict disease prognosis by observing the morphological characteristics of luterials. In addition, the morphological change of luterials is also associated with changes in the content of nucleic acids in the luterials and the sequence of the luterials, and thus enabling diagnosis of disease from nucleic acid expression pattern analysis (16S rRNA sequencing) of luterials. For example, it is possible to diagnose disease (particularly cancer) by comparing the 16S rRNA sequence of normal luterial with that of patient-derived luterial. Particularly, co-expression of Streptopyta gene and eukaryote gene can be used as a marker for diagnosing and predicting carcinogenesis.

However, luterials isolated from body fluids discharged from patients or normal people are difficult to observe because they tend to disappear in vitro within a short time or change their shape. In addition, in an abnormal environment, normal luterials are changed into mutant luterials within 24 hours, making it difficult to accurately diagnose or treat diseases. However, according to the culture method of the present invention, luterials can be cultured such that their size does not exceed certain size (500 nm).

Therefore, in another aspect, the present invention is directed to a method for culturing luterial, comprising: adding water to luterial; and culturing the luterial at a temperature of 18 to 30° C. (preferably 20 to 25° C.) under irradiation with IR light.

The water that is added in the culture process may be saline or PBS solution, but is not limited thereto. The body fluid-derived luterial before culture may be obtained according to the isolation method of the present invention and may have a size of 20-200 nm. The luterial cultured according to the culture method of the present invention may have a size of 300-800 nm. Herein, the luterial can be controlled to a size of 500 nm or less under microscopic observation. After completion of the culture, the luterial may be sorted according to size, and cooled and stored at −80° C. or stored under nitrogen or may also be stored at a temperature above zero. For storage, a preservative may be added to the luterial.

The luterial cultured as described above can be stored for a certain period of time without changing the characteristics of the luterial, and can be effectively used to diagnose disease and predict disease prognosis. As used herein, the expression "without changing the characteristics of luterial" means that the morphology or size of luterial is maintained at a level similar to that before culture in media. In addition, it means that the activity of luterial, such as mobility (e.g., nano-tracking speed), is maintained at a value similar to that before culture.

Specifically, luterial cultured according to the culture method of the present invention may be used for the following purposes. Mutant luterials have an abnormally increased morphology or size due to fusion or coagulation, unlike normal luterials (FIG. 8, FIG. 9, and FIGS. 10A-10B). By culturing the mutant luterials, a substance capable of inhibiting or preventing the mutation of luterials can be screened from the candidate substances by observing whether the changes in cultured luterial mutants.

Furthermore, a substance that promotes the fission of mutant luterials can be screened by treating cultured mutant luterials with a candidate substance or means. Since mutant luterials show patterns of fusion or coagulation events (FIG. 8, FIG. 9 and FIG. 11), by treating the mutant luterials with a candidate substance and examining whether it promotes the fission of mutant luterials to have the size of normal luterials, it would be possible to screen for a substance that inhibits the mutation of luterials or converts mutant luterials to normal luterials, that is, a substance that prevents disease caused from mutant luterials.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Observation of Luterials on Dark-Fields in Peripheral Blood

Whole blood samples were obtained from the fingertip by punching with a lancet. One drop (~1 μL) of blood was placed on a coverslip and mounted on a glass slide. Images were observed and captured under dark-field using a Nikon Ni-E microscope (Nikon, Tokyo, Japan). We abided by international human research guide lines and regulations of IRB Committee. All of research was conducted after IRB approval (IRB04009 and IRB09001) at Dankook University, Yongin-si, South Korea.

Example 2: Isolation of Blood-Derived Luterials

Fresh human plasma samples from donors were obtained before use. The luterials were obtained by centrifugation (Eppendorf, Hamburg, Germany), ultracentrifugation (Beckman Coulter, Calif., USA) and Nano-filtration systems (Whatman, N.J., USA). Isolated exosomes were processed with luterials except Nano-filtration steps. Mitochondria from platelets were purified using Mitochondria Isolation Kit for Cultured Cells kit (Thermo Scientific, Waltham, USA). The luterials were reaffirmed using Atomic Force Microscopes (FastScan-Bio, Bruker, Santa Barbara, USA) after purification.

50 cc of blood was collected from a non-small cell lung cancer patient and passed through a filter having a pore size of 0.8 μm or more, and unfiltered substances were removed. The filtered blood was repeatedly centrifuged at 1,200-5,000 rpm for 5-10 minutes to remove general microvesicles such as exosomes collected in pellets, and the supernatant was collected. The supernatant was irradiated with visible light, and the gathered luterial particles with mobility were isolated by pipetting. Because luterial is autofluorescent and mobile, luterial particles could be visualized by irradiation with visible light as described above. At this time, mobile luterial particles were isolated by pipetting under observation with a dark-field microscope or a confocal microscope. The isolated luterials were filtered through a filter having a pore size of 20 nm, and only an unfiltered portion was washed with PBS, thereby obtaining luterials. According to the above procedures, luterials having a long axis diameter of 20-800 nm could be obtained, which could be observed through a dark-field microscope or a confocal microscope.

The size distribution and concentration of the luterials were determined using an Nanosight NS300 instrument (Malvern Instruments Ltd, Malvern, UK) equipped with a green (532 nm) laser and sCMOS camera and blur, minimum track length and minimum expected particle size were set to auto. The temperature set to 25° C. The data were analysed using the NTA 3.0 (build 0068) software with the detection threshold set to 3 and screen gain at 10. Isolated luterials were diluted 1,000-10,000-fold with PBS and the luterial concentration and size distribution were measured.

The obtained luterials were sorted according to size into 20-200 nm (developmental phase)/200-400 nm (maturation phase)/400-600 nm (mitosis phase)/600-800 nm (over-mitosis phase). According to a similar method, a library of luterials with various sizes as shown in FIG. 21 was constructed, and the morphologies of luterials with various sizes are shown in FIGS. 2A through 2J.

Isolated luterials were attached on cleaved mica for 30 minutes. The mica was washed thoroughly with distilled and deionized water and dried in a desiccator. To record images, FastScan-Bio Atomic Force Microscopy (Bruker, Santa Barbara, USA) was used under tapping mode for AFM imaging by Cantilever probe (BunkerAFMprobes Inc., Camarillo, USA) with spring constant (N/m)=10-25 and frequency (kHz)=800-2000 under air conditions. Scan rate was 2 Hz and pixel was 512×512 at room temperature. The images were rendered by NanoScope analysis software. Purified genomic DNA from luterials in 40 mM HEPES and 10 mM $NiCl_2$ buffer was adsorbed to freshly cleaved mica for 10 min. The mica was washed with deionized water and dried in a desiccator.

FastScan-Bio Atomic Force Microscope (Bruker, Santa Barbara, USA) was used under tapping mode for AFM imaging by Cantilever probe (BunkerAFMprobes Inc., Camarillo, USA) with spring constant (N/m)=0.4-1.2 and frequency (kHz)=200-400 under air condition. Scan rate was 1 Hz and pixel was 512×512 at room temperature. The images were rendered by NanoScope analysis software.

As for Scanning Electron Microscopy (SEM), luterials were fixed with freshly made Karnovsky's fixative (2% glutaraldehyde, 2% paraformaldehyde in 0.1M Phosphate buffer) overnight at 4° C. After fixation, pelleted samples were resuspended and spread on coverslips coated with 1:10 diluted poly-L-lysine. The coverslips were then washed twice with PBS for 30 minutes and postfixed with 1% $OsO_4$ for 2 hours. After washes and dehydration, the samples were incubated in 98% isoamyl acetate overnight at 4° C. Finally, the coverslips were dried by using a Critical Point Dryer (Quorum, model K850) and coated with Gold by sputter coating (Quorum, model Q150R ES). Pictures were taken by MERLIN SE2 and In-lens mode (Carl Zeiss, Oberkochen, Germany)

As to Scanning Transmission Electron Microscopy (STEM), For improved visualization of the luterials, samples were dialyzed to remove plasma proteins using Float-A-Lyzer G2 Dialysis Device (MWCO 300, Spectrum Laboratories, Inc. CA. USA) for 14 days. During dialysis, PBS were exchanged every 24 hours. Dialyzed samples were then concentrated by centrifuging samples with Centrifugal Filters (MWCO 3K, Merck Millipore, Darmstadt, German) at 3,000 g for 120 minutes. Samples were prefixed with Karnovsky's fixative (2% Glutaraldehyde, 2% Paraformaldehyde in 0.1M Phosphate buffer) for overnight at 4° C. The fixed sample pellet was added in 2% agarose. Samples were washed with PBS and postfixed with 1% OsO4 and then processed for dehydration, infiltration and embedding in Poly/Bed 812 (Polysciences). Semithin sections (150-200 nm) were cut using an ultra-microtome (RMC, PT-XL) and stained with 1% toluidine blue to identify the location of samples. Ultrathin sections (70-80 nm) were cut, and collected on collodion coated copper grids (200 mesh) and then double stained with 2% Uranyl acetate and Reynold's lead citrate solution to adjust the contrast. Images were captured by smart SEM® and ATLAS, MERLIN (Carl Zeiss, Oberkochen, Germany) and JEM-1011 (Jeol. Tokyo, Japan).

For pre-embedded immunogold labelling, samples were washed with PBS (pH 6.9) and treated 0.1% Saponin in PBS for 10 minutes at room temperature. After several washes, samples were prefixed with Karnovsky's fixative (2% Glutaraldehyde, 2% Paraformaldehyde in 0.1M Phosphate buffer) for overnight at 4° C. Next day, the samples were reacted with 0.2% tannic acid (Sigma Inc. USA) for 10 minutes at room temperature, and then washed several times. The samples were immunolabelled with anti-CD63 antibody (Santa Cruz Bio., Texas, USA) and anti-VDAC antibody (Cell signaling, Danvers, USA) overnight at 4° C., washed with PBS and incubated with 10 nm protein A-gold conjugated antirabbit or anti-mouse secondary antibody (Sigma, Saint Louis, USA) for 2 hours at 4° C. followed by several washes with PBS. Samples were fixed with 1.5% glutaraldehyde (EM grade, Sigma) for 10 minutes at room temperature. After washes in PBS, samples were postfixed with 1% OsO4 for 30 minutes at room temperature and processed for dehydration and infiltration and finally embedded in Poly/Bed 812 (Polysciences). Semi-thin sections (150-200 nm) were cut using an ultra-microtome (RMC, PT-XL) and stained with 1% toluidine blue to identify the location of samples. Ultrathin sections (70-80 nm) were cut, and collected on formavar/carbon coated nickel grids (200 mesh) and then double stained with 2% Uranylacetate and Reynold's lead citrate solution to adjust the contrast. Images were captured by smart SEM® and ATLAS, MERLIN (Carl Zeiss, Oberkochen, Germany).

Example 3: Isolation of Semen-Derived Luterials

Semen was centrifuged at 2000-4000 rpm for 5-30 minutes, and the supernatant was filtered through a filter having a pore size of 2-5 μm. The filtered solution was centrifuged at 3000-7000 rpm for 5-20 minutes, followed by filtration through a filter having a pore size of 0.5-2 μm. Because luterials are autofluorescent and mobile, luterial particles can be visualized when the filtered solution was irradiated with visible light. At this time, mobile luterial particles were isolated by pipetting under observation with a dark-field microscope or a confocal microscope. The isolated luterials were filtered through a filter having a pore size of 20 nm, and only an unfiltered portion was washed with PBS, thereby obtaining luterials which could be observed through a dark-field microscope or a confocal microscope.

Example 4: Mobility and Distance Measurements in Peripheral Blood on Microscopy

To track the mobility of the luterials, the recorded real-time videos under the dark-field were used. The speed and moving distance of the luterials were measured by Nikon NIS software (Nikon, Tokyo, Japan). The speed of these luterials was summarized by mean and standard error. Statistical analysis of differences in mobility and moving distance between normal healthy individuals and cancer patients was performed by Mann-Whitney U test using SAS Software (version 9.3, NC, USA). All statistical significances were indicated by P value <0.05. We used Leica TCS-SP8 microscope (Leica, Wetzlar, Germany) and Nikon Ni-E microscope (Nikon, Tokyo, Japan) to video record fission and fusion of the luterials in peripheral blood.

Example 5: Isolation of DNA and RNA

Genomic DNA from the purified luterials was extracted with the TRIzol (Invitrogen, Carlsbad, USA) and collected via chloroform extraction and alcohol precipitation according to the manufacturer's instruction. Isolated genomic DNA was purified using a NucleoSpin gDNA Clean-up kit (MACHEREY-NAGEL, DUren, Germany). For total RNA collection, the RNA was extracted using the TRIzol, followed by the miRCURY™ RNA Isolation Kit (Exiqon, Vedbaek, Denmark). The rest of the procedure was processed according to the manufacturer's instruction. Quantification of DNA and RNA was performed by Qubit (Life Technologies, Carlsbad, USA) and Nanodrop (Tecan F200, Männedorf, Switzerland).

Example 6: Characteristics of Luterials (1) Structure

Among the luterials obtained in Example 1, luterials having a size of about 20-400 nm were imaged with a confocal laser scanning microscope (Zeiss), a transmission electron microscope, a scanning electron microscope, an atomic force microscope and a confocal scanner (Leica TCS-SP8). As a result, it was shown that the luterials also had a double-layered, multiple layered ring-like membrane structure or a mixed form of double-layered and multiple layered membrane structure and a non-completed internal cristae structure, similar to mitochondria, and were observed in the same wavelength range as that for mitochondria. In addition, it could be observed that the luterials were circular or oval in shape (FIG. 1, FIG. 2H, FIG. 13 and FIG. 14).

(2) Staining Characteristics

Among the luterials obtained in Example 1, luterials having a size of about 20-800 nm were stained with Mitotracker, Rhodamine 123, Acridine Orange and Janus green B, and tested for their positive staining. The results showed that even the plant-derived luterials were also stained by Mito-tracker, Rhodamine 123, Acridine Orange and Janus green B (FIGS. 2A, 2B, 2F and 2J; and FIG. 3 through FIG. 6).

(3) Autofluorescence

Figure 5:
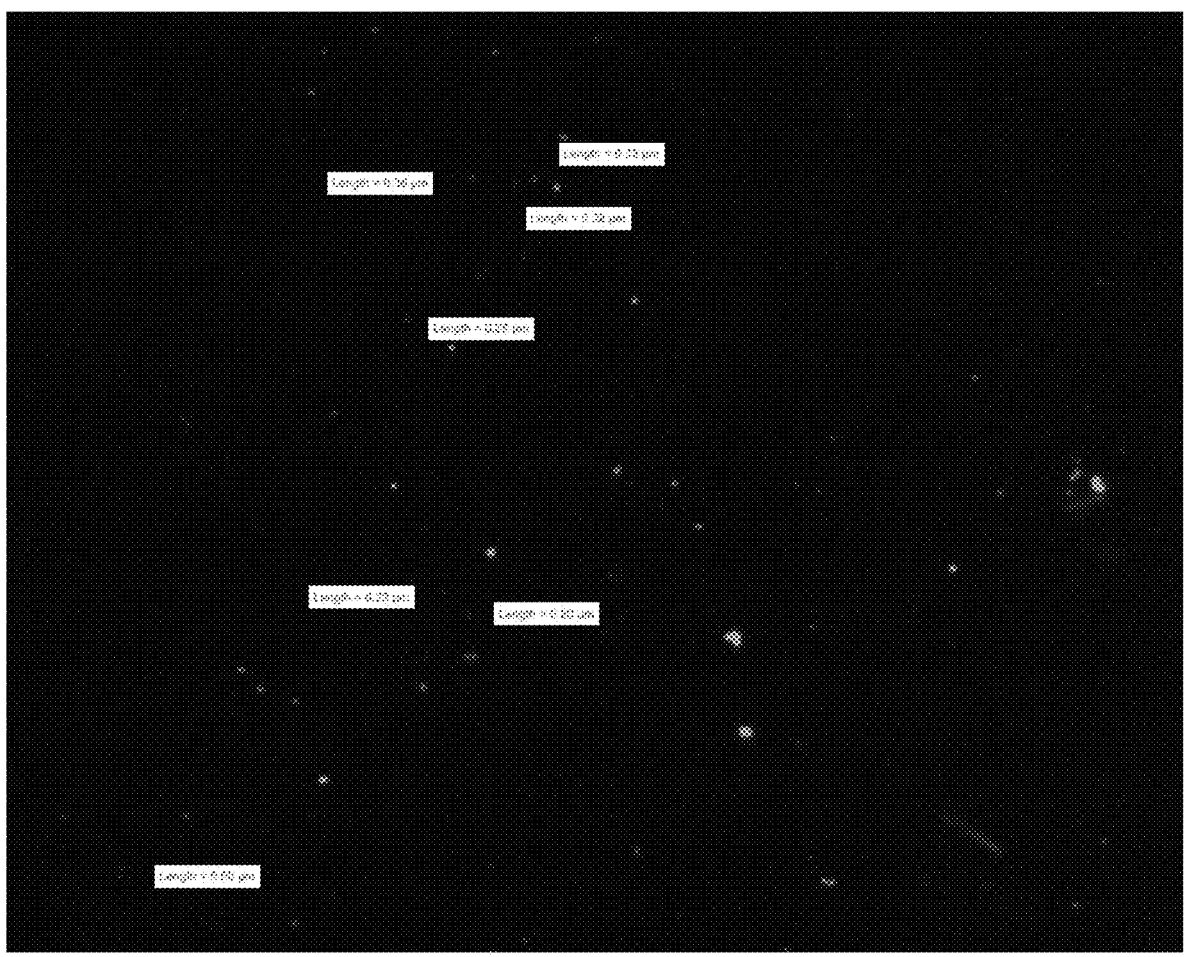
FIG. 5 is an image showing the results of staining luterial with Acridine Orange and then observing whether the luterial would be positively stained.
Figure 6:
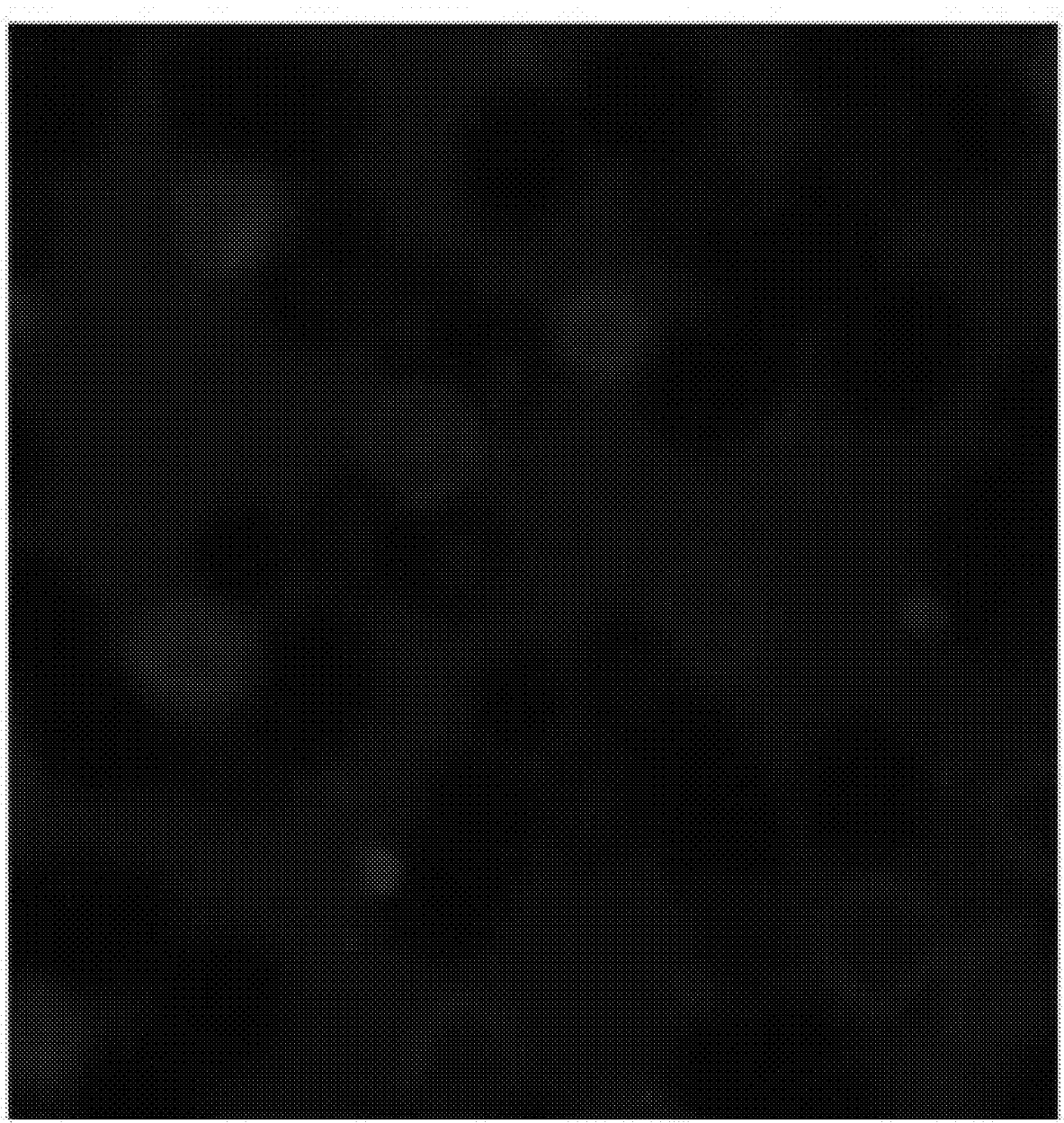
FIG. 6 is an image showing the results of staining luterial with DAPI (4',6-diamidino-2-phenylindole) and then observing whether the luterial would be positively stained.

Among the luterials obtained in Example 1, luterials having a size of about 20-800 nm were analyzed through fluorescence images. The result showed that luterials responded to light (FIG. 5).

(4) Mobility

Figure 7A:
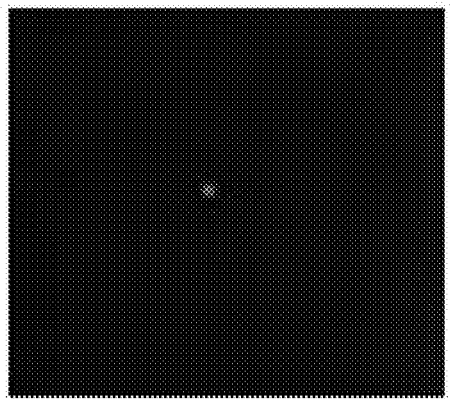
FIGS. 7A through 7C depict images showing the results of measuring the mobility of luterial using nano-trackers (FIG. 7A: before measurement.
Figure 7B:
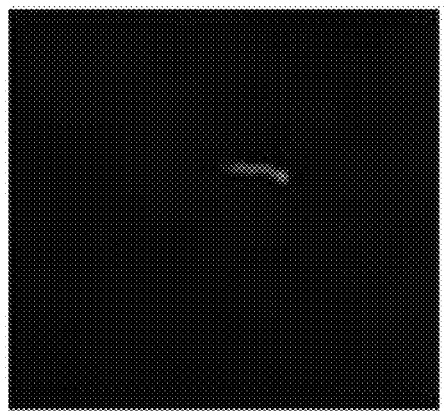
Figure 7C:
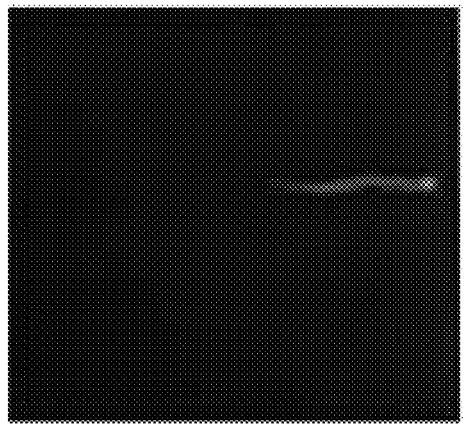

The mobility of luterials obtained in Example 1 was measured by nano-tracking (3i Inc., USA) analysis. Specifically, luterials were observed with a bright-field microscope, tracking was set in the center of the luterial, and nano-tracking was performed. Then, the real-time movement trajectory of the luterial was recorded and the speed per second of the luterial was calculated (FIGS. 7A through 7C).

As a result, the nano-tracking speed of the luterials according to the present invention was measured to be about 13-25 μm/sec.

(5) Analysis of whether luterials contain RNA and DNA

The luterials having a size of 200-400 nm, isolated in Example 1, were imaged with an atomic force microscope. As shown in FIG. 2H, FIG. 15, FIGS. 16A-16B and FIG. 17, luterials contain nucleic acids such as RNA or DNA.

In order to isolate total RNA and DNA from luterials having a size of 200-400 nm isolated in Example 1, a QIAGEN kit (RNeasy Micro Kit: Cat 74004) was used, followed by quantification using an Experion RNA (DNA) StdSens (Bio-Rad) chip.

Luterials were recovered by centrifugation (at 8,000 g for 1 hr 30 min), and then lysed by adding 50 μl of lysis buffer RLT plus (guanidine isothiocycanate, detergents) from the kit mixed with 3.5 μl of beta-mercaptoethanol and then passing them 5-10 times through a syringe equipped with a 20-gauge needle. The sample lysis buffer was then transferred to an AllPrep DNA spin column, followed by centrifugation (at ≥8000 g for 15 sec) to separate DNA remaining on the column from the RNA contained in the buffer that passed through the column.

Next, 350 μl of 70% ethanol was added to the same volume of the sample lysis buffer that passed through the column (RNA) and well mixed. Then 700 μl of the mixture was transferred to a RNease MinElute spin column and centrifuged (at ≥8000 g for 15 sec), and the buffer that passed through the column was removed. The column was washed sequentially with 350 μl of RW1, 500 μl of RPE buffer and 500 μl of 80% ethanol. All the centrifugation procedures (≥8000 g for 15 sec) used as described above were performed under the same conditions. To obtain RNA, 14 μl of RNeasy-free solution was added to the column and then centrifuged (at ≥8000 g for 60 sec), thereby isolating luterial RNA.

For isolation of genomic DNA (gDNA), a FastDNA SPIN Kit (MP Biomedical) was used. The isolated luterials were added to the tube, followed by addition of 978 μl of sodium phosphate buffer and 122 μl of MT buffer. The mixture was homogenized for 40 sec, and then centrifuged at 14,000 g for 10 min to collect the supernatant, after which 250 μl of PPS (Protein Precipitation Solution) was added to the supernatant and mixed for 10 min. After centrifugation at 14,000 g for 5 min, and the supernatant was transferred into a 15 ml tube, and this procedure was repeated twice. For DNA binding, the resulting supernatant was placed on a rotor for 2 minutes, and then placed on a silica matrix support for 3 minutes. 600 μl of the supernatant was carefully added to a SPIN filter and was centrifuged at 14,000 g for 1 min, and then the supernatant was discarded, and 500 μl of SEWS-M was added to the remaining pellets and resuspended. After centrifugation for 1 min, the supernatant was discarded, and centrifugation was repeated such that any buffer would not remain. Then, 50 μl of DES (DNase/Pyrogen-Free Water) was added to the remaining material, followed by centrifugation at 14,000 g for 1 min, and then genomic DNA was isolated.

Figure 16A:
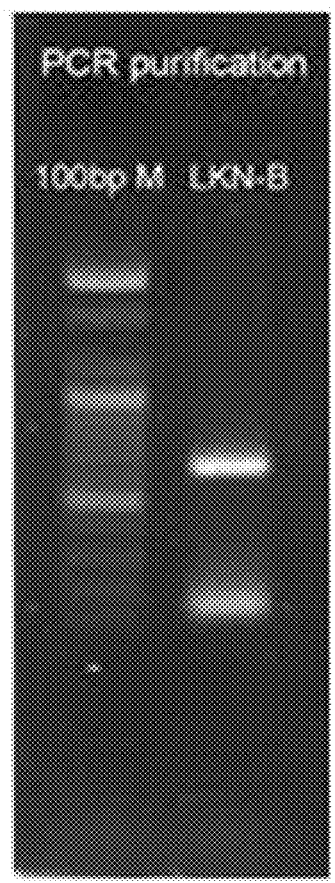
FIG. 16A shows the bioanalyzer results of analyzing whether luterial contains DNA.
Figure 16B:
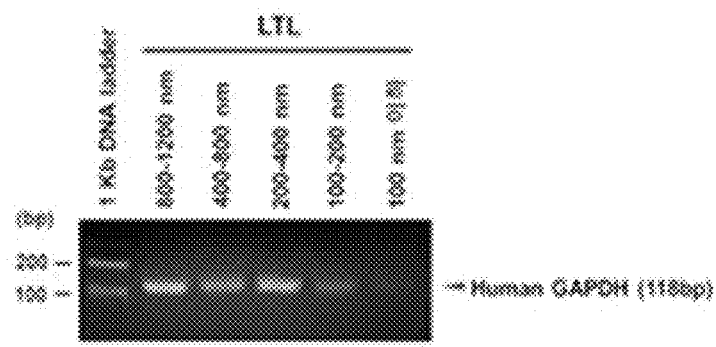
FIG. 16B shows the results of qRT-PCR, which indicate that the GAPDH gene expression of DNA changes depending on the size of luterial.
Figure 17:
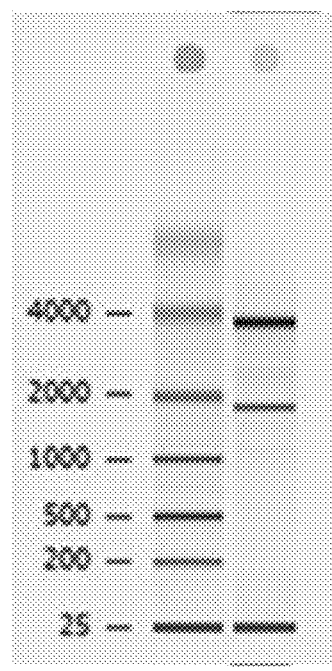
FIG. 17 shows the bioanalyzer results of analyzing whether luterial contains DNA.

Quantification was performed using an Experion RNA (DNA) StdSens (Bio-Rad) chip. The result, as shown in FIGS. 16A-16B and FIG. 17, indicated that the luterials contained RNA and DNA.

(6) 16S rRNA Sequencing 16S rRNA (ribosomal ribonucleic acid) is a DNA that interacts with various proteins to form ribosomes. Because the rate of change in the nucleotide sequence of 16S rRNA is significantly lower than those of the nucleotide sequences of most of other genes in the genome, it is recognized that the similarity of the 16S rRNA sequence reflects the phylogenetic distance between organisms.

① Blood-Derived Luterials

The luterials obtained in Example 1 were treated using a FastDNA SPIN kit (MP Biomedicals, Cat 6560-200) to extract gDNA. Using the extracted gDNA, the 16S rRNA of the luterial was amplified using a PCR-premix (iNtRON Biotechnology, Korea) and primers of SEQ ID NOs: 1 to 23.

The amplified PCR products were sequenced using a BigDye Terminator Cycle Sequencing Ready Reaction kit (Applied Biosystems, USA) and an automated DNA analyzer system (PRISM 3730XL DNA analyzer, Applied Biosystems). The amplified PCR products were a total of 1461 fragments. Among them, 1407 fragments showed homology with the proteobacteria-derived gene, 20 fragments showed homology with the Acidobacteria-derived gene, and 11 fragments showed homology with the Actinobacteria-derived gene (Table 6).

The fragments with the analyzed nucleotide sequences were combined using SeqMan software (DNASTAR), thereby obtaining the nucleotide sequence of 16S rRNA.

Figure 24A:
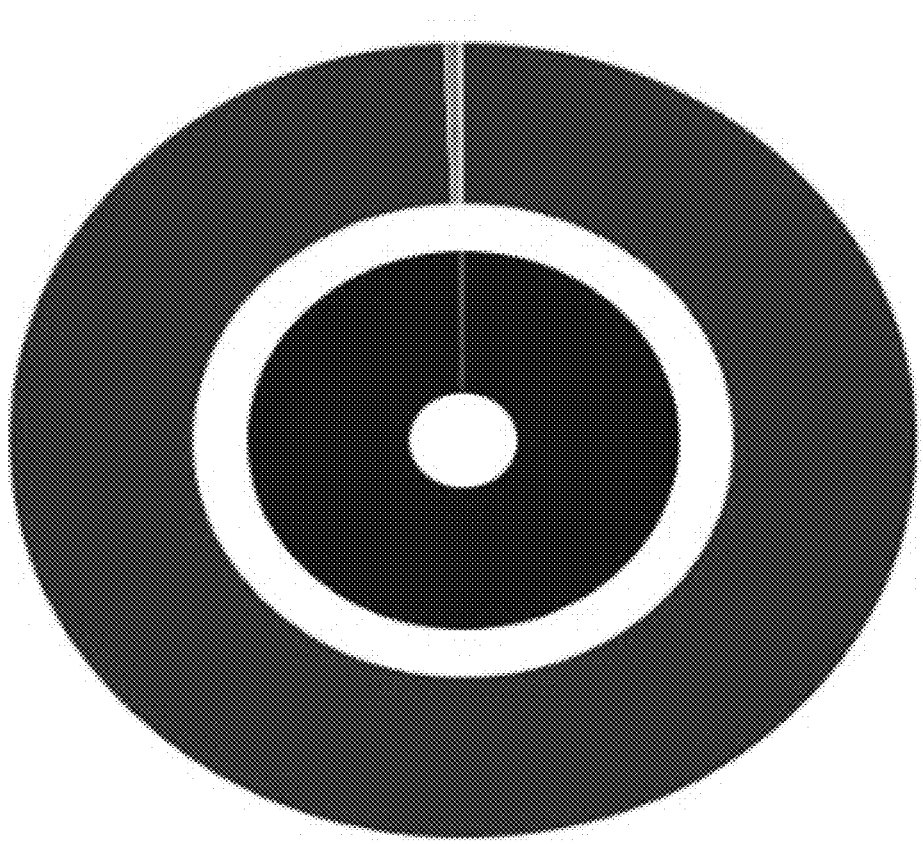
FIGS. 24A through 24D show percentage of bacterial homology of luterial DNA as determined by 16S rRNA sequencing of luterials having various sizes, derived from the blood of healthy persons (blood pH: 7.2-7.4) (FIG. 24A: 100 nm or less.
Figure 24B:
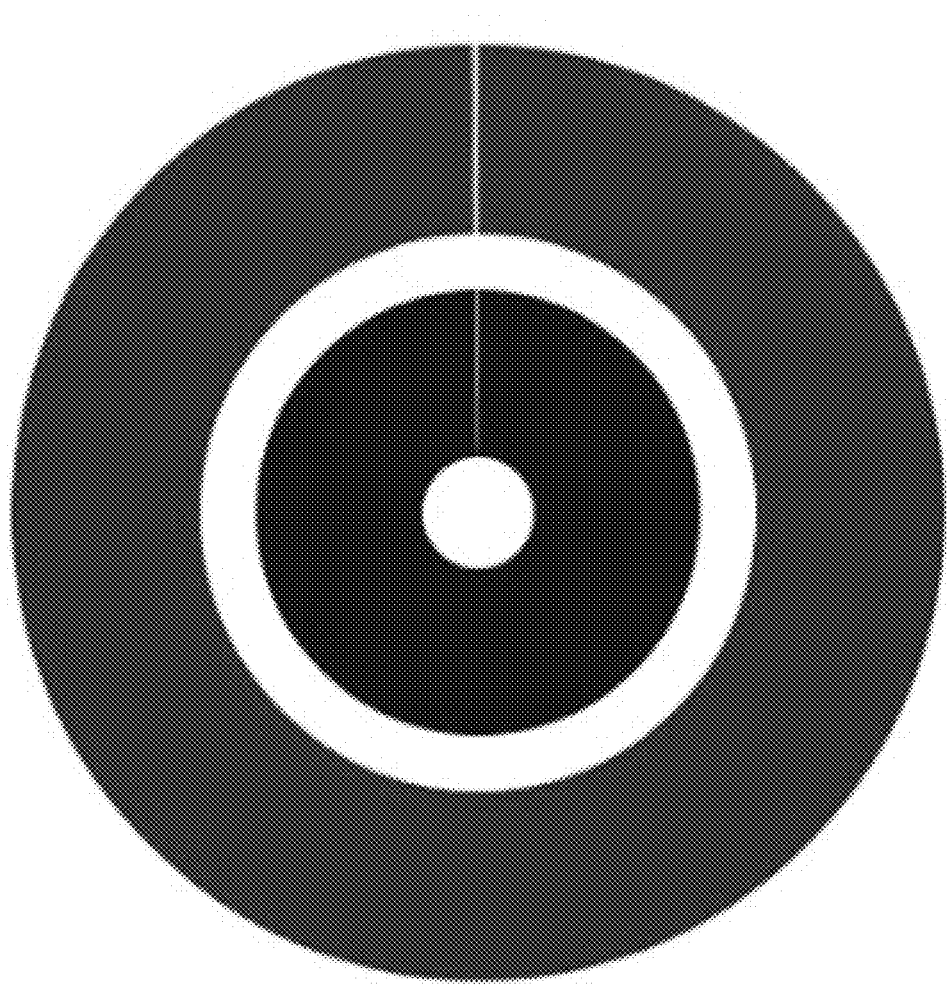
Figure 24C:
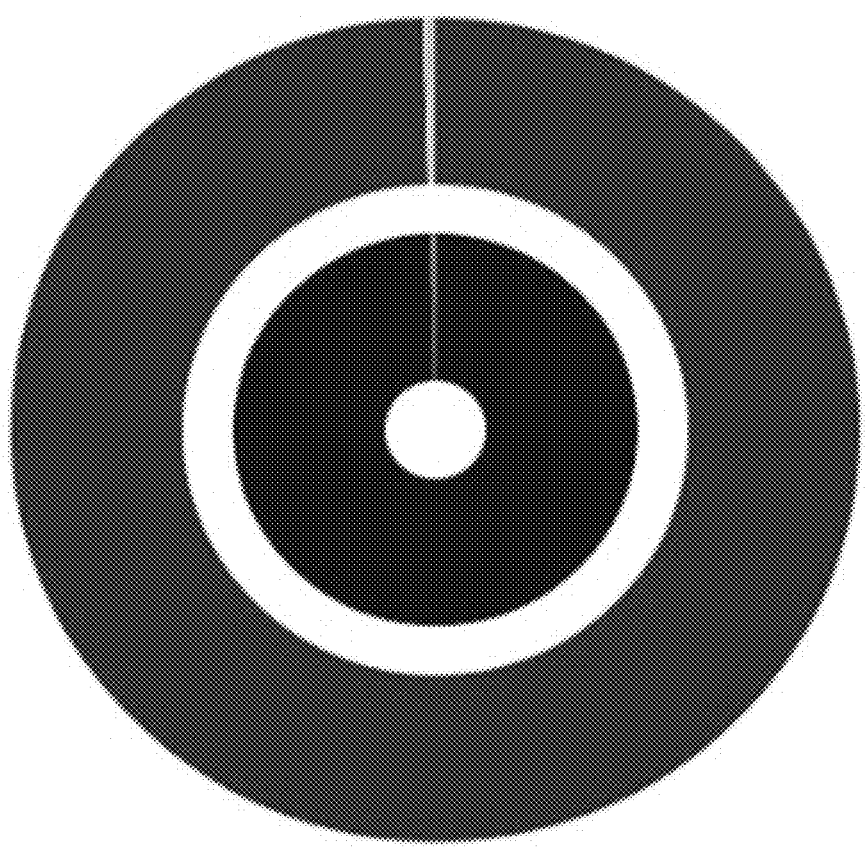
Figure 24D:
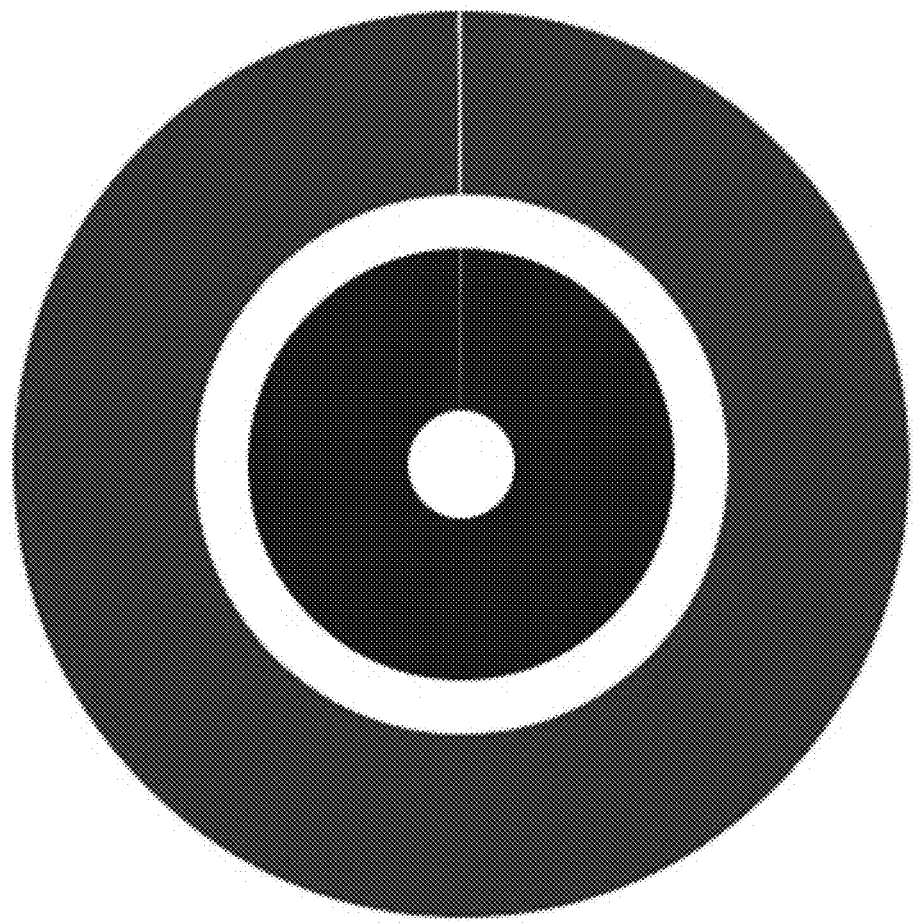

FIGS. 24A through 24D show bacterial homologies of luterial DNA of healthy individual as determined by 16S rRNA sequencing of luterials derived from the blood of healthy persons (blood pH: 7.2-7.4), and shows the results of analysis performed for luterials of various sizes (FIG. 24A: 100 nm or less, FIG. 24B: 100-200 nm, FIG. 24C: 200-400 nm, and FIG. 24D: 400-800 nm). There was no significant difference among the luterial sizes, and luterials all showed homology with the genes derived from Proteobacteria, Firmicutes and Bacteroidetes.

Figure 25B:
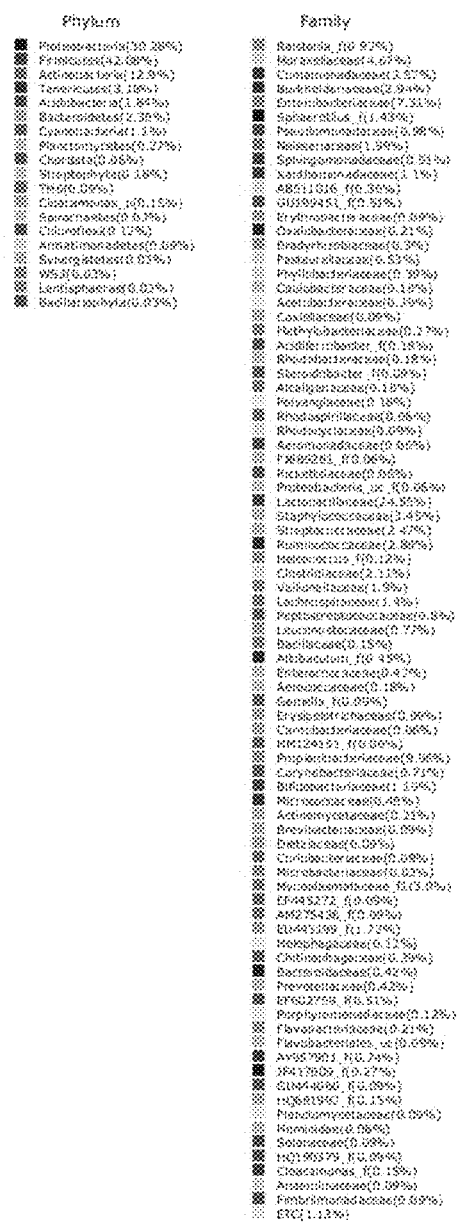
Figure 25C:
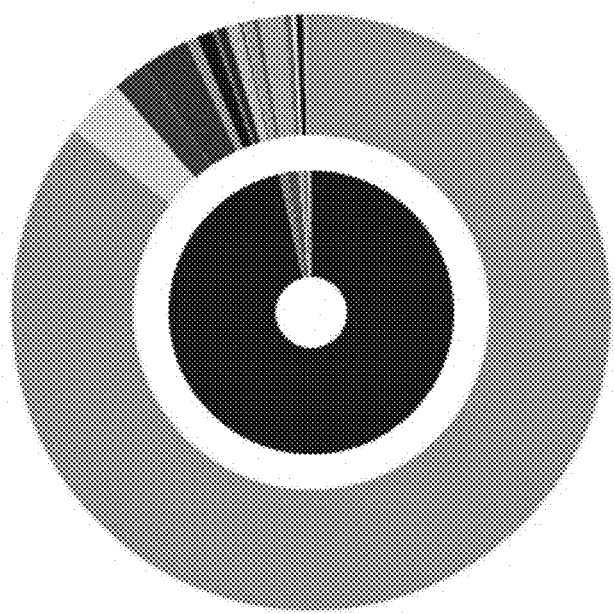
Figure 25D:
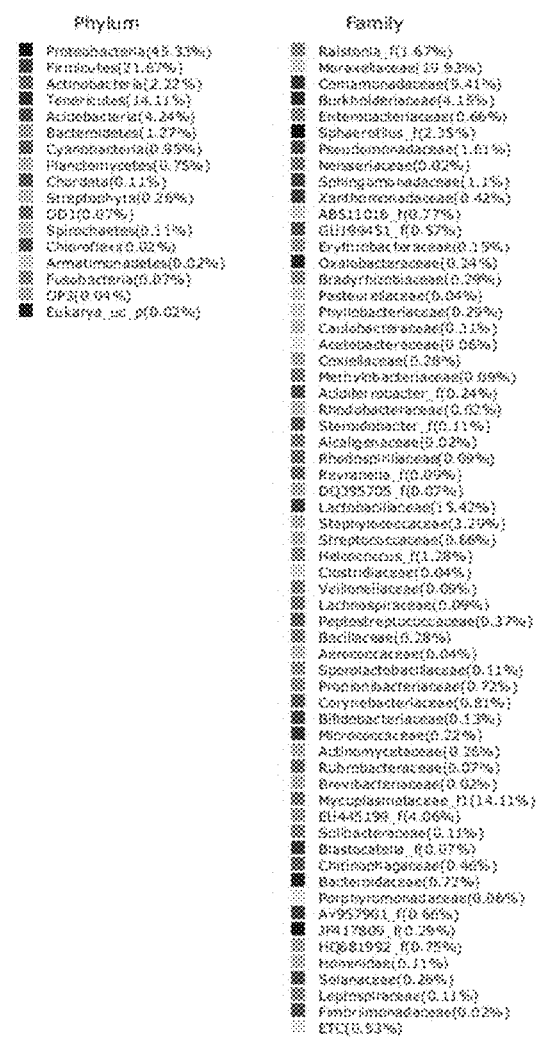

FIG. 25C shows bacterial homologies of luterial DNA obtained from the patients with disease. The 16S rRNA sequencing data of 200-400 nm luterials derived from blood of a patient with a fatigue or disease condition (blood pH: 7.0 or less) were used. Unlike in healthy conditions, luterial genes obtained from the patients showed homology with Streptophyta-derived genes.

Figure 26A:
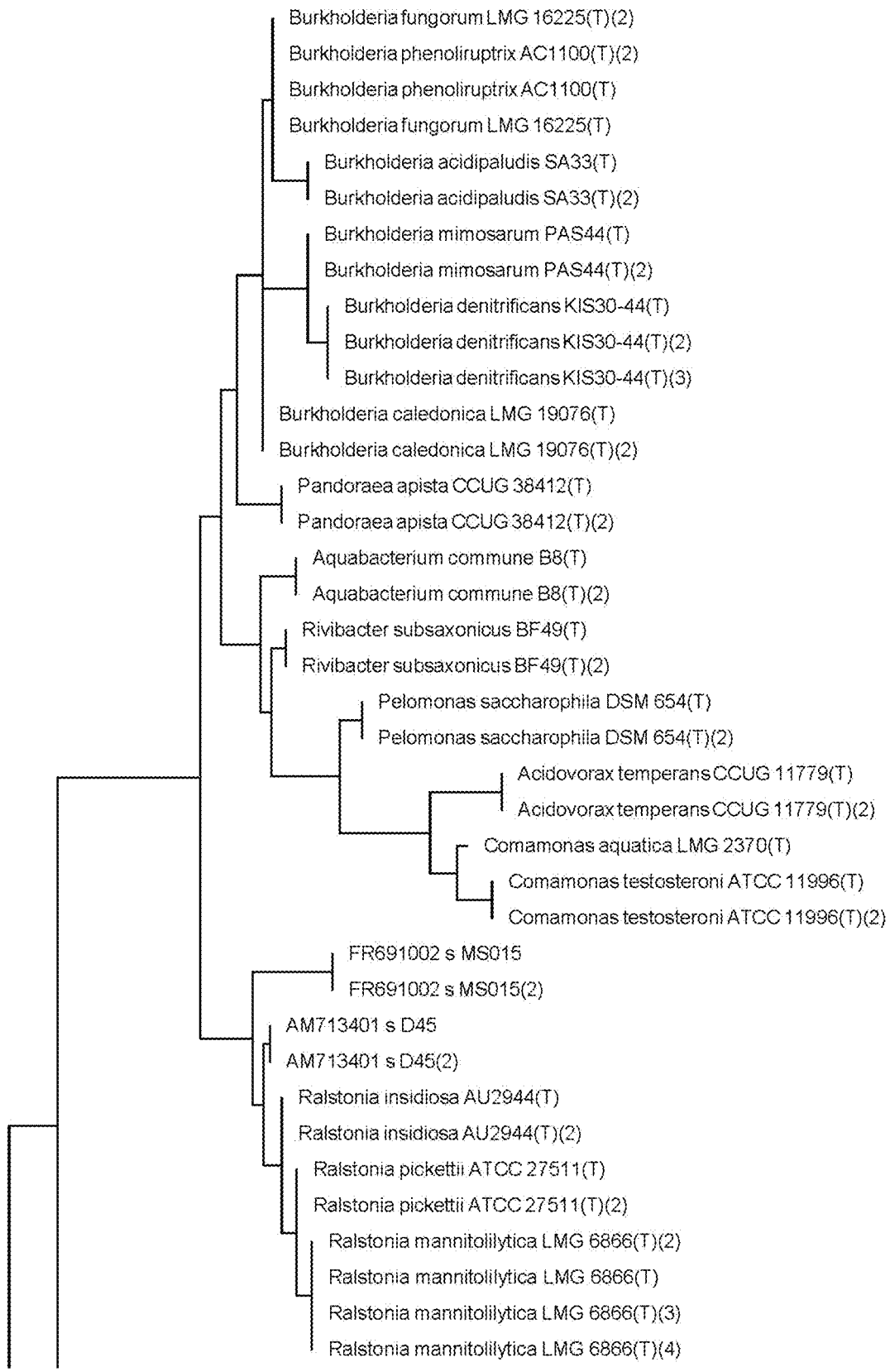
FIGS. 26A through 26C show phylogenetic trees based on the 16S rRNA sequence of blood-derived luterials.
Figure 26B:
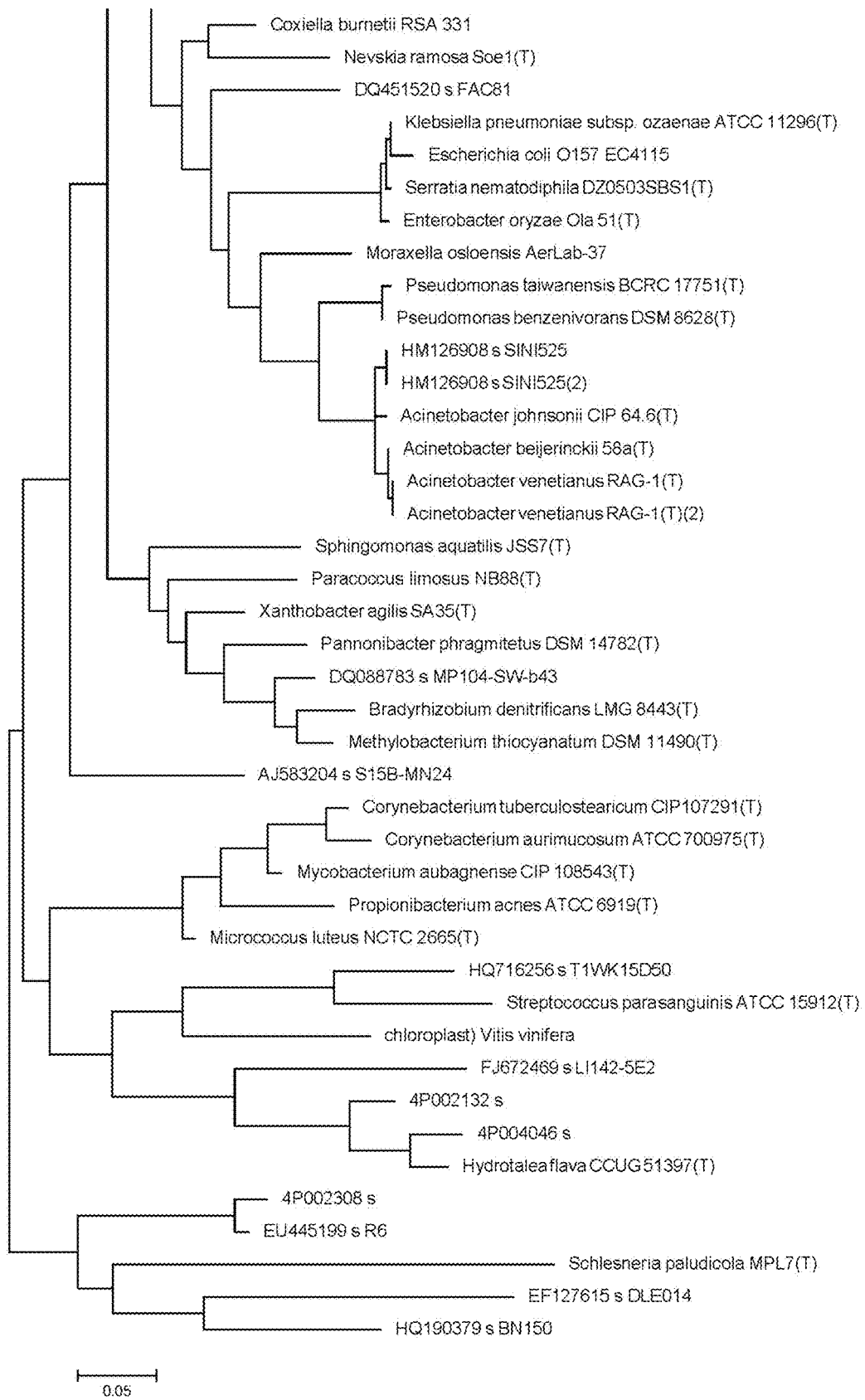
Figure 26C:
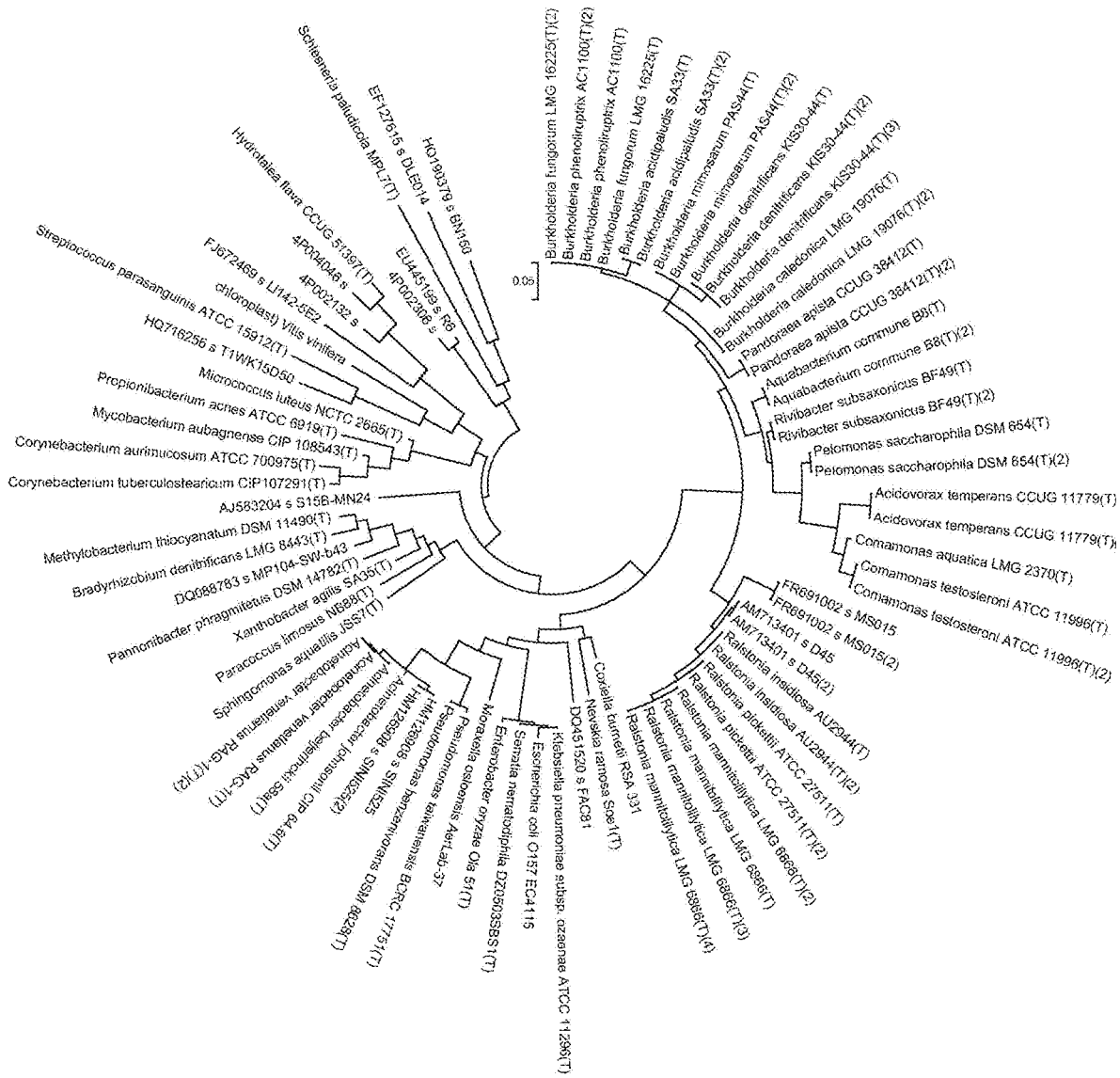

FIGS. 26A through 26C show phylogenetic trees based on the 16S rRNA sequence of blood-derived luterials.

TABLE 6

| Rank | Taxonomy | Name | LKL-B | SUM (Ratio) | LKL-B | Sum (Number) |
|---|---|---|---|---|---|---|
| Phylum | Bacteria;;;Proteobacteria | Proteobacteria | 96.3039 | 96.3039 | 1407 | 1407 |
| Phylum | Bacteria;;;Acidobacteria | Acidobacteria | 1.36893 | 1.36893 | 20 | 20 |
| Phylum | Bacteria;;;Actinobacteria | Actinobacteria | 0.75291 | 0.75291 | 11 | 11 |
| Phylum | Bacteria;;;Bacteroidetes | Bacteroidetes | 0.54757 | 0.54757 | 8 | 8 |
| Phylum | Bacteria;;;Cyanobacteria | Cyanobacteria | 0.41068 | 0.41068 | 6 | 6 |
| Phylum | Eukarya; Viridiplantae;;;Streptophyta | Streptophyta | 0.27379 | 0.27379 | 4 | 4 |
| Phylum | Bacteria;;;Firmicutes | Firmicutes | 0.20534 | 0.20534 | 3 | 3 |
| Phylum | Bacteria;;;TM6 | TM6 | 0.06845 | 0.06845 | 1 | 1 |
| Phylum | Bacteria;;;Planctomycetes | Planctomycetes | 0.06845 | 0.06845 | 1 | 1 |

It was shown that the 16S rRNA fragments of the blood-derived luterials showed homology with various bacteria, including beta-proteobacteria, gamma-proteobacteria, Bacteroidetes, Firmicutes and Streptophyta.

Generally, when the relatedness of gDNA in microbial-taxonomy is less than 70%, the microorganisms are recognized as independent strains. In addition, it was demonstrated by statistical analysis that, when the homology of the 16S rRNA sequence is less than 97%, the gDNA relatedness is less than 70%. Thus, cells having a homology of 97.0% or more with the 16S rRNA fragments of the luterials were analyzed. As shown in Tables 5 to 7 below, the blood-derived luterials showed a homology of 100% with gamma-proteobacteria, a homology of 97.53% with Firmicutes, and a homology of 97% or more with Bacteroidetes.

Meanwhile, as shown in Table 10, abnormal acidic luterials showed a homology of 99% or more with Streptophyta.

TABLE 7

Characteristics of Luterial by 16S rRNA Seq

| Raw data Seq Name | Sequence | Hit accession | Similarity | Taxonomic assignment |
|---|---|---|---|---|
| IOFBYRO01DTJ3I | ATTGAACGCTGGCGGCAGGCTTAACACA TGCAAGTCGAGCGGAGATGAGGTGCTTG CACCTTATCTTAGCGGCGGACGGTGAGT AATGCTTAGGAATCTGCCTATTAGTGGG GGGACAACATTCCGAAAGGGATGCTAAT ACCGCATACGTCCTACGGGAGAAAGCAG GGGATCTTCCGGACCTTGCGCTAATAGAT GAGCCTAAGTCGGATTAGCTAGTTGGTG GGGTAAAGGCCTACCAAGGCGACGATCT GTAGCGGGTCTGAGAGGATGATCCGCCA CACTGGGACTGAGACACGGCCCAGACTC CTACGGGAGGCAGCAGTGGGGAATATTG GACAATGGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | AM410704 | 100 | Bacteria;;; Proteobacteria;; Gammaproteobacteria;; Pseudomonadales;; Moraxellaceae;; *Acinetobacter*; *Acinetobacter junii*;; LMG 998-AM410704(T) |
| IOFBYRO01DUOG5 | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAATA CCGCATACGTCCTACGGGAGAAAGCAGG GGATCTTCCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | AM410704 | 100 | Bacteria;;; Proteobacteria;; Gammaproteobacteria;; Pseudomonadales;; Moraxellaceae;; *Acinetobacter*; *Acinetobacter junii*;; LMG 998-AM410704(T) |
| IOFBYRO01BHYT4 | TTGAACGCTGGCGGCAGGCTTAACACAT GCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGGAATGCTAAT ACCGCATACGTCCTACGGGAGAAAGCA | AM410704 | 100 | Bacteria;;; Proteobacteria;; Gammaproteobacteria;; Pseudomonadales;; Moraxellaceae;; *Acinetobacter; Acinetobacter junii*;; LMG 998-AM410704(T) |

TABLE 7-continued

Characteristics of Luterial by 16S rRNA Seq

| Raw data Seq Name | Sequence | Hit accession | Similarity | Taxonomic assignment |
|---|---|---|---|---|
| | GGGGATCTTCGGACCTTGCGCTAATAGA TGAGCCTAAGTCGGATTAGCTAGTTGGT GGGGTAAAGGCCTACCAAGGCGACGAT CTGTAGCGGGTCTGAGAGGATGATCCGC CACACTGGGACTGAGACACGGCCCAGAC TCCTACGGGAGGCAGCAGCGGGGAATA TTGGACAATGGGGGAACCCTGATCCAG CCATGCCGCGTGTGTGAAGAAGGCCTTA TGGTTGTAAAGCACTTTAAGCGAGGAGG AGGCTACTGAGACTAATACTCTTGGATAG TGGACGTTACTCGCAGAATAAGCACCGG CTAACTCTGTG | | | |
| IOFBYRO01CYAL1 | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAATA CCGCATACGTCCTACGGGAGAAAGCAGG GGATCTTCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGAACCCTGATCCAGCC ATGCCGCGTGTGTGAAGAAGGCCTTATG GTTGTAAAGCACTTTAAGCGAGGAGGAG GCTACTGAGACTAATACTCTTGGATAGTG GACGTTACTCGCAGAATAAGCACCGGCT AACTCTGTG | AM410704 | 100 | Bacteria;;; Proteobacteria;; Gammaproteobacteria;; Pseudomonadales;; Moraxellaceae;; *Acinetobacter*; *Acinetobacter junii*;; LMG 998-AM410704(T) |
| IOFBYRO01DRDH1 | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAACA CCGCATACGTCCTACGGGAGAAAGCAGG GGATCTTCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | AM410704 | 100 | Bacteria;;; Proteobacteria;; Gammaproteobacteria;; Pseudomonadales;; Moraxellaceae;; *Acinetobacter*; *Acinetobacter junii*;; LMG 998-AM410704(T) |
| IOFBYRO01BWKSQ | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAATA CCGCATACGTCCTACGGGAGAAAGCAGG GGATCTTCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | AM410704 | 100 | Bacteria;;; Proteobacteria;; Gammaproteobacteria;; Pseudomonadales;; Moraxellaceae;; *Acinetobacter*; *Acinetobacter junii*;; LMG 998-AM410704(T) |
| IOFBYRO01BWKSO | ATTGAACGCTGGCGGCAGGCTTAACACA TGCAAGTCGAGCGGAGATGAGGTGCTTG CACCTTATCTTAGCGGCGGACGGGTGAG TAATGCTTAGGAATCTGCCTATTAGTGGG GGACAACATTCCGAAAGGAATGCTAATA | AM410704 | 100 | Bacteria;;; Proteobacteria;; Gammaproteobacteria;; Pseudomonadales;; Moraxellaceae;; *Acinetobacter*; *Acinetobacter* |

TABLE 7-continued

Characteristics of Luterial by 16S rRNA Seq

| Raw data Seq Name | Sequence | Hit accession | Similarity | Taxonomic assignment |
|---|---|---|---|---|
| | CCGCATACGTCCTACGGGAGAAAGCAGG GGATCTTCGGACCTTGCGCTAATAGATG AGCCTAAGTCGGATTAGCTAGTTGGTGG GGTAAAGGCCTACCAAGGCGACGATCTG TAGCGGGTCTGAGAGGATGATCCGCCAC ACTGGGACTGAGACACGGCCCAGACTCC TACGGGAGGCAGCAGTGGGGAATATTG GACAATGGGGGAACCCTGATCCAGCCA TGCCGCGTGTGTGAAGAAGGCCTTATGG TTGTAAAGCACTTTAAGCGAGGAGGAGG CTACTGAGACTAATACTCTTGGATAGTGG ACGTTACTCGCAGAATAAGCACCGGCTA ACTCTGTG | | | *junii*;; LMG 998-AM410704(T) |
| IOFBYRO01A8KAW | TATTAGTGGGGGACAACATTCCGAAAGG AATGCTAATCCGCATACGTCCTACGGGA GAAAGCAGGGGACCTTCGGGCCTTGCGC TAATAGATGAGCCTAAGTCGGATTAGCT AGTTGGTGGGGTAAAGGCCTACCAAGGC GACGATCTGTAGCGGGTCTGAGAGGATG ATCCGCCACACTGGGACTGAGACACGGC CCAGACTCCTACGGGAGGCAGCAGTGGG GAATATTGGACAATGGGGGGAACCCTG ATCCAGCCATGCCGCGTGTGTGAAGAAG GCCTTATGGTTGTAAAGCACTTTAAGCGA GGAGGAGGCTACTAGTATTAATACTACTG GATAGTGGACGTTACTCGCAGAATAAGC ACCGGCTAACTCTGTG | AKIQ01000085 | 100 | Bacteria;;; Proteobacteria;; Gammaproteobacteria;; Pseudomonadales;; Moraxellaceae;; *Acinetobacter*; *Acinetobacter venetianus*;; RAG-1-AKIQ01000085(T) |

TABLE 8

*Firmicutes*

| Raw data Seq Name | Sequence | Hit accession | Similarity | Taxonomic assignment |
|---|---|---|---|---|
| IOFBYRO01ANZSO | GGCGGCGTGCCTAATACATGCAAGTAGA ACGCTGAAGCTTGGTGCTTGCACCGAGC GGATGAGTTGCGAACGGGTGAGTAACGC GTAGGTAACCTGCCTCTTAGCGGGGGAT AACTATTGGAAACGATAGCTAATACAGCA TAAAAGTCGATATCGCATGATATTGATTT GAAAGGTGCAATTGCATCACTAAGAGAT GGACCTGCGTTGTATTAGCTAGTTGGTG AGGTAACGGCTCACCAAGGCGACGATAC ATAGCCGACCTGAGAGGGTGATCGGCCA CACTGGGACTGAGACACGGCCCAGACTC CTACGGGAGGCAGCAGTAGGGAATCTTC GGCAATGGGGGCAACCCTGACCGAGCA ACGCCGCGTGAGTGAAGAAGGTTTTTCG GATCGTAAAGCTCTGTTGTAAGAGAAGAA CGAGTGTGAGAGTGGAAAGTTCACACTG TGACGGTAACTTACCAGAAAGGGACGGC TAACTACGTG | ADVN01000004 | 97.53 | Bacteria;;; Firmicutes;; Bacilli;; Lactobacillales;; Streptococcaceae;; *Streptococcus*; *Streptococcus parasanguinis*;; ATCC 15912-ADVN01000004(T) |

TABLE 9

*Bacteroidetes*

| Raw data Seq Name | Sequence | Hit accession | Similarity | Taxonomic assignment |
|---|---|---|---|---|
| IOFBYRO01BUV34 | TGAACGCTAGCGGCAGGCTTAATACATG CAAGTCGTGGGGCAGCACAGAATAGCAA TATTTGGGTGGCGACCGGCAAACGGGTG CGGAACACGTACACAACCTTCCGATAAG TGGGGATAGCCCAGAGAAATTGGATT AATACCCCGTAACATATAGAGATGGCATC GTCTTTATATTATAGCTTCGGTGCTTATT GATGGGTGTGCGTCTGATTAGGTAGTTG | 4P004046 | 99.79 | Bacteria;;; Bacteroidetes;; Sphingobacteria;; Sphingobacteriales;; Chitinophagaceae;; 4P004046_g; 4P004046_s;; 4P004046 |

TABLE 9-continued

*Bacteroidetes*

| Raw data Seq Name | Sequence | Hit accession | Similarity | Taxonomic assignment |
|---|---|---|---|---|
| | GCGGGGTAACGGCCCACCAAGCCTACG ATCAGTAGCTGATGTGAGAGCATGATCA GCCACACGGGCACTGAGACACGGGCCC GACTCCTACGGGAGGCAGCAGTAAGGAA TATTGGACAATGGGCGCAAGCCTGATCC AGCCATGCCGCGTGAAGGATGAATGTCC TCTGGATTGTAAACTTCTTTTATTTGGGA CGAAAAAGAGCATTCTTGCTCACTTGACG GTACCAAGTGAATAAGCACCGGCTAACT CCGTG | | | |
| IOFBYRO01AEZDS | GATGAACGCTAGCGATAGGCCTAACACA TGCAAGTCGAGGGGCAGCACATGAAGTA GCAATACTGATGGTGGCGACCGGCGCA CGGGTGAGTAACACGTATGCAACCTACC TTCAACAGGAGAATAACCCGTCGAAAGA CGGACTAATACTCCATAACACAGGGATC CCACATGGGAATATTGTTAAAGATTTAT CGGTTGAAGATGGGCATGCGCTCCATTA GCTAGTTGGTGAGGTAACGGCTCACCAA GGCAACGATGGATAGGGGAACTGAGAG GTTTATCCCCCACACTGGTACTGAGACA CGGACCAGACTCCTACGGGAGGCAGCA GTGAGGAATATTGGTCAATGGAGGCAAC TCTGAACCAGCCACGTCGCGTGAAGGAT GACGGCCCTACGGGTTGTAAACTTCTTTT GTAAGGGAATAAAGTTAGTTACGTGTAAC TATTTGCATGTACCTTACGAATAAGGATC GGCTAACTCCGTG | FJ672469 | 97.34 | Bacteria;;; Bacteroidetes;; Bacteroidia;; Bacteroidales;; Porphyromonadaceae;; AB243818_g; FJ672469_s;; FJ672469 |
| IOFBYRO01BP52Z | GATGAACGCTAGCGATAGGCCTAACACA TGCAAGTCGAGGGGCAGCACATGAAGTA GCAATACTGATGGTGGCGACCGGCGCA CGGGTGAGTAACACGTATGCAACCTACC TTCAACAGGAGAATAACCCGTCGAAAGA CGGACTAATACTCCATAACACAGGGATC CCACATGGGAATATTGTTAAAGATTTAT CGGTTGAAGATGGGCATGCGCTCCATTA GCTAGTTGGTGAGGTAACGGCTCACCAA GGCAACGATGGATAGGGGAACTGAGAG GTTTATCCCCCACACTGGTACTGAGACA CGGACCAGACTCCTACGGGAGGCAGCA GTGAGGAATATTGGTCAATGGAGGCAAC TCTGAACCAGCCACGTCGCGTGAAGGAT GACGGCCCTACGGGTTGTAAACTTCTTTT GTAAGGGAATAAAGTTAGTTACGTGTAAC TATTTGCATGTACCTTACGAATAAGGATC GGCTAACTCCGTG | FJ672469 | 97.34 | Bacteria;;; Bacteroidetes;; Bacteroidia;; Bacteroidales;; Porphyromonadaceae;; AB243818_g; FJ672469_s;; FJ672469 |
| IOFBYRO01BBMIP | TGAACGCTAGCGGCAGGCTTAATACATG CAAGTCGTGGGGCAGCACAGAATAGCAA TATTTGGGTGGCGACCGGCAAACGGGTG CGGAACACGTACACAACCTTCCGATAAG TGGGGGATAGCCCAGAGAAATTTGGATT AATACCCCGTAACATATAGAGATGGCATC GTCTTTATATTAGCTTCGGTGCTTATT GATGGGTGTGCGTCTGATTAGGTAGTTG GCGGGGTAACGGCCCACCAAGCCTACG ATCAGTAGCTGATGTGAGAGCATGATCA GCCACACGGGCACTGAGACACGGGCCC GACTCCTACGGGAGGCAGCAGTAAGGAA TATTGGACAATGGGCGCAAGCCTGATCC AGCCATGCCGCGTGAAGGATGAATGTCC TCTGGATTGTAAACTTCTTTTATTTGGGA CGAAAAAGAGCATTCTTGCTCACTTGAC GGTACCAAGTGAATAAGCACCGGCTAAC TCCGTG | 4P004046 | 99.79 | Bacteria;;; Bacteroidetes;; Sphingobacteria;; Sphingobacteriales;; Chitinophagaceae;; 4P004046_g; 4P004046_s;; 4P004046 |
| IOFBYRO01BBHTW | ATGGACGCTAGCGGCAGGCTTAATACAT GCAAGTCGTGGGGCAGCACAGAATAGCA ATATTTGGGTGGCGACCGGCAAACGGGT GCGGAACACGTACACAACCTTCCGATAA GTGGGGGATAGCCCAGAGAAATTTGGAT TAATACCCCGTAACATATAGAGATGGCAT CGTCTTTATATTAGCTTCGGCGCTTATT | 4P004046 | 99.58 | Bacteria;;; Bacteroidetes;; Sphingobacteria;; Sphingobacteriales;; Chitinophagaceae;; 4P004046_g; 4P004046_s;; 4P004046 |

TABLE 9-continued

Bacteroidetes

| Raw data Seq Name | Sequence | Hit accession | Similarity | Taxonomic assignment |
|---|---|---|---|---|
| | TGATGGGTGTGCGTCTAATTAGGTAGTT GGCGGGGTAACGGCCCACCAAGCCTAC GATCAGTAGCTGATGTGAGAGCATGATC AGCCACACGGGCACTGAGACACGGGCC CGACTCCTACGGGAGGCAGCAGTAAGG AATATTGGACAATGGGCGCAAGCCTGAT CCAGCCATGCCGCGTGAAGGATGAATGT CCTCTGGATTGTAAACTTCTTTTATTTGG GACGAAAAAGAGCATTCTTGCTCACTTG ACGGTACCAAGTGAATAAGCACCGGCTA ACTCCGTG | | | |
| IOFBYRO01BQCEI | GATGAACGCTAGCGATAGGCCTAACACA TGCAAGTCGAAGGGGCAGCACATGAAGT AGCAATACTGATGGTGGCGACCGGCGCA CGGGTGAGTAACACGTATGCAACCTACC TTCAACAGGAGAATAACCCGTCGAAAGA CGGACTAATACTCCATAACACAGGGATC CCACATGGGAATATTGTTAAAGAGTTTA TCGGTTGAAGATGGGCATGCGCTCCATT AGCTAGTTGGTGAGGTAACGGCTCACCA AGGCAACGATGGATAGGGGAACTGAGA GGTTTATCCCCCACACTGGTACTGAGAC ACGGACCAGACTCCTACGGGAGGCAGC AGTGAGGAATATTGGTCAATGGAGGCAA CTCTGAACCAGCCACGTCGCGTGAAGGA TGACGGCCCTACGGGTTGTAAACTTCTT TGTAAGGGAATAAAGTTAGTTACGTGTAA CTATTTGCATGTACCTTACGAATAAGGAT CGGCTAACTCCGTG | FJ672469 | 97.34 | Bacteria;;; Bacteroidetes;; Bacteroidia;; Bacteroidales;; Porphyromonadaceae;; AB243818_g; FJ672469_s;; FJ672469 |
| IOFBYRO01CGIIX | ATGAACGCTAGCGGCAGGCTTAATACAT GCAAGTCGAGGGGCAGCACGGTATAGC AATATATGGGTGCGACCGGCAAACGGG TGCGGAACACGTACACAACCTTCCGGTG AGCGGGGGATAGCCCAGAGAAATTTGGA TTAATACCCCATACTATAATGATCAGGCA TCTGGTTATTATCAAAGGCTTCGGCCGCT TATTGATGGGTGTGCGTCTGATTAGGTA GTTGGCGGGGTAGAGGCCCACCAAGCC TACGATCAGTAGCTGATGTGAGAGCATG ATCAGCCACACGGGCACTGAGACACGGG CCCGACTCCTACGGGAGGCAGCAGTAA GGAATATTGGACAATGGACGCAAGTCTG ATCCAGCCATGCTGCGTGAAGGATGAAT GCCCTCTGGGTTGTAAACTTCTTTTACAG GGGAAGAAAGTTATCTTTTTTAGGATATT TGACGGTACCCTATGAATAAGCACCGGC TAACTCCGTG | FN665659 | 97.8 | Bacteria;;; Bacteroidetes;; Sphingobacteria;; Sphingobacteriales;; Chitinophagaceae;; Hydrotalea; Hydrotalea flava;; CCUG 51397-FN665659(T) |
| IOFBYRO01BUV35 | TGAACGCTAGCGGCAGGCTTAATACATG CAAGTCGTGGGGCAGCACAGAATAGCAA TATTTGGGTGCGACCGGCAAACGGGTG CGGAACACGTACACAACCTTCCGATAAG TGGGGGATAGCCCAGAGAAATTTGGATT AATACCCCGTAACATATAGAGATGGCATC GTCTTTATATTATAGCTTCGGTGCTTATT GATGGGTGTGCGTCTGATTAGGTAGTTG GCGGGGTAACGGCCCACCAAGCCTACG ATCAGTAGCTGATGTGAGAGCATGATCA GCCACACGGGCACTGAGACACGGGCCC GACTCCTACGGGAGGCAGCAGTAAGGAA TATTGGACAATGGGCGCAAGCCTGATCC AGCCATGCCGCGTGAAGGATGAATGTCC TCTGGATTGTAAACTTCTTTTATTTGGGA CGAAAAGAGCATTCTTGCTCACTTGACG GTACCAAGTGAATAAGCACCGGCTAACT CCGTG | 4P004047 | 99.24906689 | Bacteria;;; Bacteroidetes;; Sphingobacteria;; Sphingobacteriales;; Chitinophagaceae;; 4P004046_g; 4P004046_s;; 4P004047 |

TABLE 10

*Streptophyta*

| Raw data Seq Name | Sequence | Hit accession | Similarity | Taxonomic assignment |
|---|---|---|---|---|
| IOFBYR001BVMU5 | GATGAACGCTGGCGGCATGCTTAACACA TGCAAGTCGGACGGGAAGTGGTGTTTCC AGTGGCGGACGGGTGAGTAACGCGTAA GAACCTGCCCTTGGGAGGGGAACAACA GCTGGAAACGGCTGCTAATACCCCGTAG GCTGAGGAGCAAAAGGAGGAATCCGCC CGAGGAGGGGCTCGCGTCTGATTAGCTA GTTGGTGAGGCAATAGCTTACCAAGGCG ATGATCAGTAGCTGGTCCGAGAGGATGA TCAGCCACACTGGGACTGAGACACGGCC CAGACTCCTACGGGAGGCAGCAGTGGG GAATTTTCCGCAATGGGCGAAAGCCTGA CGGAGCAATGCCGCGTGGAGGTAGAAG GCCCACGGGTCGTGAACTTCTTTTCCCG GAGAAGAAGCAATGACGGTATCTGGGGA ATAAGCATCGGCTAACTCTGTG | CAAP02016081 | 100 | Eukarya; Viridiplantae;; Streptophyta;; eudicotyledons;; core eudic otyledons;; Vitaceae;; Vitis; Vitis vinifera;; CAAP02016081 |
| IOFBYR001DG9Y3 | GATGAACGCTGGCGGCATGCTTAACACA TGCAAGTCGGACGGGAAGTGGTGTTTCC AGTGGCGGACGGGTGAGTAACGCGTAA GAACCTGCCCTTGGGAGGGGAACAACA GCTGGAAACGGCTGCTAATACCCCGTAG GCTGAGGAGCAAAAGGAGGAATCCGCC CGAGGAGGGGCTCGCGTCTGATTAGCTA GTTGGTGAGGCAATAGCTTACCAAGGCG ATGATCAGTAGCTGGTCCGAGAGGATGA TCAGCCACACTGGGACTGAGACACGGCC CAGACTCCTACGGGAGGCAGCAGTGGG GAATTTTCCGCAATGGGCGAAAGCCTGA CGGAGCAATGCCGCGTGGAGGTAGAAG GCCCACGGGTCGTGAACTTCTTTTCCCG GAGAAGAAGCAATGACGGTATCTGGGGA ATAAGCATCGGCTAACTCTGTG | CAAP02016081 | 100 | Eukarya; Viridiplantae;; Streptophyta;; eudicotyledons;; core eudic otyledons;; Vitaceae;; Vitis; Vitis vinifera;; CAAP02016081 |
| IOFBYR001BVXH2 | GATGAACGCTGGCGGCATGCTTAACACA TGCAAGTCGGACGGGAAGTGGTGTTTCC AGTGGCGGACGGGTGAGTAACGCGTAA GAACCTGCCCTTGGGAGGGGAACAACA GCTGGAAACGGCTGCTAATACCCCGTAG GCTGAGGAGCAAAAGGAGGAATCCGCC CGAGGAGGGGCTCGCGTCTGATTAGCTA GTTGGTGAGGCAATAGCTTACCAAGGCG ATGATCAGTAGCTGGTCCGAGAGGATGA TCAGCCACACTGGGACTGAGACACGGCC CAGACTCCTACGGGAGGCAGCAGTGGG GAATTTTCCGCAATGGGCGAAAGCCTGA CGGAGCAATGCCGCGTGGAGGTAGAAG GCCCACGGGTCGTGAACTTCTTTTCCCG GAGAAGAAGCAATGACGGTATCTGGGGA ATAAGCATCGGCTAACTCTGTG | CAAP02016081 | 100 | Eukarya; Viridiplantae;; Streptophyta;; eudicotyledons;; core eudic otyledons;; Vitaceae;; Vitis; Vitis vinifera;; CAAP02016081 |
| IOFBYR001CVD3E | GATGAACGCTGGCGGCATGCTTAACACA TGCAAGTCGGACGGGAAGTGGTGTTTCC AGTGGCGGACGGGTGAGTAACGCGTAA GAACCTGCCCTTGGGAGGGGAACAACA GCTGGAAACGGCTGCTAATACCCCGTAG GCTGAGGAGCAAAAGGAGGAATCCGCC CGAGGAGGGGCTCGCGTCTGATTAGCTA GTTGGTGGGCAATAGCTTACCAAGGCG ATGATCAGTAGCTGGTCCGAGAGGATGA TCAGCCACACTGGGACTGAGACACGGCC CAGACTCCTACGGGAGGCAGCAGTGGG GAATTTTCCGCAATGGGCGAAAGCCTGA CGGAGCAATGCCGCGTGGAGGTAGAAG GCCCACGGGTCGTGAACTTCTTTTCCCG GAGAAGAAGCAATGACGGTATCTGGGGA ATAAGCATCGGCTAACTCTGTG | CAAP02016081 | 99.77 | Eukarya; Viridiplantae;; Streptophyta;; eudicotyledons;; core eudic otyledons;; Vitaceae;; Vitis; Vitis vinifera;; CAAP02016081 |

② Semen-Derived Luterials

The semen-derived luterials obtained in Example 2 were subjected to gDNA extraction, PCR amplification and sequencing according to the above-described method. FIGS. 25A through 25D show bacterial homology of luterial DNA as determined by 16S rRNA sequencing of luterials derived from semen in both normal condition and a fatigue and disease condition (sperm pH: 7.0 or less). The analysis was performed with the luterials of various sizes (FIG. 25A: 100 nm or less, FIG. 25B: 100-200 nm, and FIG. 25D: 400-800 nm).

The normal semen-derived luterials showed homology with the genes derived from Proteobacteria, Firmicutes and Bacteroidetes, like the blood-derived luterials. Particularly, the luterials showed homology with the Chordata-derived gene.

Luterial DNA derived from semen in abnormal acidic conditions showed homology with the Streptophyta-derived gene.

(7) Measurement of ATP Content 10 mL of each of four media, including a control, luterial, luterial with SSH (12 hr) and luterial with SSF (12 hr), was placed in a tube, and glucose (100 mg/mL) and ADP substrate (1 mM) were added thereto, followed by culture in water bath at 37° C. At 30-min intervals after the start of the culture, 100 µl of a sample was collected, placed in a tube, and diluted 10-fold with 900 µl of distilled water. Then, 10 µl of the sample was transferred into a fresh tube, and 100 µl of luciferase reagent contained in the ATP kit was added thereto, and measurement was immediately performed five times using a luminometer.

As shown in FIG. 18, the media containing luterial showed an increase in the ATP concentration compared to the control media without luterial. Such results suggest that the luterial has the ability to produce ATP. In comparing the results between SSH and SSF media, the ATP concentration in the SSF-added group was higher than that in the SSH-added group (FIG. 18).

Example 7: Differences Between Exosome/Mitochondria and Luterials (1) Immunofluorescence The luterials, exosomes and mitochondria from platelets were attached on coverslips coated with poly-L-lysine, incubated with indicated primary antibodies conjugated with fluorescent probe for 30 minutes. After 3 washes with PBS, fluorescence-stained slides were mounted with a coverslip in anti-fading mounting medium and examined by Super resolution-SIM; Axio Observer.Z1 SR, with ELYRA PS.1 (Carl Zeiss, Oberkochen, Germany) and LSM-780 (Carl Zeiss, Oberkochen, Germany) and N-SIM (Nikon, Tokyo, Japan) confocal microscopy. Isolated mitochondria from platelets were performed by Mitochondria isolation kit (Thermo Fisher Scientific Inc., Waltham, USA) according to the manufacturer's instruction. Sources of immunofluorescence primary antibodies are as follows: Acridine Orange (Thermo Fisher Scientific Inc., Waltham, USA), MitoTracker Red (Invitrogen, Eugene, USA), MitoTracker Orange (Invitrogen, Eugene, USA), Rhodamine 123 (Sigma-Aldrich, Saint Louis, USA), Janus Green B (Thermo Fisher Scientific Inc., Waltham, USA), DAPI (Sigma-Aldrich, Saint Louis, USA), and CD39-PE (Miltenyi Biotec Bio., Auburn, USA).

(2) Immunoblots

Western blots were performed as follows: the unknown-nanoparticle and exosome lysates were collected from the appropriate fractions of the sucrose gradient assay. In short, 500 µl of blood plasma filtered with a 800 nm filter was laid on top of the sucrose gradient with tiers of 60%, 45%, 30% and 8% (w/w) of sucrose in PBS, 875 µl each. The samples were ultracentrifuged at 50,000 rpm for 38 min in a swing bucket rotor (MLS-50, Beckman Coulter) and 11 fractions were obtained, Fraction 1 composed of 500 µl from the top most layer. The remaining fractions 2-11 were collected from the top, 350 µl each. Proteins of the luterials (Fraction 1) and exosomes (Fractions 5-8) were prepared using TRIzol (Invitrogen) protein isolation procedure. Total lysates were separated by SDS-PAGE and transferred to PVDF membrane (Immobilon P, Millipore). Blots were blocked in Tris-buffered saline 0.1% (v/v) Tween-20 (TBS-T), and 5% (wt/v) non fat dry milk (Bio-Rad) for 1 hour on a shaker at room temperature. Primary antibodies were added to blocking solution and incubated overnight at 4° C. on a shaker. Blots were washed three times with 1×TBS-T and secondary antibodies were added into 3% TBS-T non fat dry milk and incubated for 1 hour at room temperature on a shaker. After several washes, enhanced chemiluminescence (ECL) reactions were performed as described by the manufacturer (Western Lightning Kit, Perkin Elmer). The following antibodies were used: anti-CD63 (sc-5275, Santa Cruz Bio.), CD9 (sc-13118, Santa Cruz Bio.), Tsg101 (sc-7964, Santa Cruz Bio.), Flotillin-1 (610821, BD Transduction Laboratories), CD39 (sc-18766, Santa Cruz Bio.) and GAPDH (2118S, Cell Signaling).

(3) Quantitative Reverse Transcription Polymerase Chain Reaction (qRT-PCR)

cDNA was prepared with a Superscript® III First-strand Synthesis Supermix for qRT-PCR kit (Invitrogen, Carlsbad, USA) according to the manufacturer's protocol and PCR was carried out with Taqman PCR conditions and probes (TaqMan® Gene Expression Assays, Applied Biosystems) against 7 mitochondrial gene transcripts. The following assays from Applied Biosystems were used to quantify the expression levels: MT-ND1 (Hs02596873_s1), MT-CO1 (Hs02596864_g1), MT-ATP6 (Hs02596862_g1), MT-ATP8 Hs02596863_g1), MT-RNR1 (Hs02596859_g1), MT-RNR2 (Hs02596860_s1), and MT-7S (Hs02596861_s1). GAPDH was used as an internal control. The relative expression of the qRT-PCR results was calculated according to the ΔΔ Ct methods as described by Livak K J, et al. (Analysis of relative gene expression data using real-time quantitative PCR and the 2(-Delta Delta C(T)) Method. Methods. 2001; 25(4):402-8.).

(4) Capillary Sequencing

To amplify whole mitochondrial genome, two primer sets (1st, HM594F (CTCCTCAAAGCAATACACTG: SEQ ID NO: 25) and HM8818R (TGGGTGGTTGGTGTAAATGA: SEQ ID NO: 26); 2nd, HM7910F (ACGAGTACACCGAC-TACGGC: SEQ ID NO: 27), HM796R (AG-GCTAAGCGTTTTGAGCTG: SEQ ID NO: 28) were designed based on the Revised Cambridge Reference Sequence (rCRS) for the Long-range PCR. Using the DNA of the unknown-nanoparticle isolated with LaboPass™ Plasmid Mini Kit (CosmoGen Tech, Seoul, South Korea) and TaKaRa LA Taq polymerase (TaKaRa Bio., Shiga, Japan), long range PCR was conducted with the following conditions; initial denaturation step (94° C. for 3 minutes), 20 cycles of 3-step cycling (94° C. for 20 seconds, 52° C. for 30 seconds, and 68° C. for 10 minutes), 15 cycles of 3-step cycling (94° C. for 20 seconds, 52° C. for 30 seconds, and 68° C. for 11 minutes), and final extension (68° C. for 10 minutes). Sequences of amplified long-range PCR products sized 8225 bp and 9458 bp were analyzed with capillary sequencing service from CosmoGene Tech (CosomoGene Tech, Seoul, South Korea) with ABI 3730XL DNA analyzer (Applied Biosystems, Foster City, USA) using newly designed 29 primers. The same procedures were performed for the mitochondrial DNA isolated from blood using Mitochondria Isolation Kit for Cultured Cells kit (Thermo Scientific, Waltham, USA) and LaboPass™ Plasmid Mini Kit (CosmoGen Tech, Seoul, South Korea).

Results for capillary sequencing of Luterial are described in FIG. 33 through FIG. 42.

(5) Next Generation Sequencing (NGS)

The DNA extract was prepared using IntegneX Apollo 324 system and sequenced by Illumina NextSeq 500 with 2×150 bp read length (Paired-End) in a single lane to maximize the amount of data. All procedures for sequencing were followed from Harvard FAS sequencing core protocol (http://sysbio.harvard.edu/csb/index.html). For Mitochondria search, raw sequence data were aligned using BWA (version 0.7.10)-MEM with mitochondria database from NCBI. Sequence depth and coverage of mitochondria were calculated using SAMtools (version 0.1.19) with parameter 'depth'. For Taxonomy Profiling, raw sequence data were first processed to filter out the adapters and low-quality reads based on the following criteria using sickle: Raw reads were trimmed to have quality score greater than 20 and minimum length of 60 bp; The passed short reads from pre-filtering of each DNA sample were assembled by the Ray Meta (version 2.3.0) assembler with the recommended parameters of '-k 31'; Scaffolds were filtered if the length is less than 500 bp. The raw sequence reads were aligned against the assembled scaffolds using BWA (version 0.7.6a)-MEM algorithm. Sequence depth of scaffolds was calculated using SAMtools (version 0.1.19) with parameter 'depth'. Also aligned read count was calculated using SAMtools (version 0.1.19) with parameter 'view'. Scaffolds and read counts of scaffold inputs were used to determine which organisms comprise the given sample. Scaffolds were classified by homology-based classification method using megaBLAST (version 2.2.23) with 'nt' database from NCBI. Scaffolds were classified by taxonomy ID using hierarchical data browser Krona. Krona chart of taxonomy abundance is shown as HTML summary report. The taxonomy annotation table is generated using in-house scripts with taxonomy database from NCBI.

As a result, all three mitochondrion-specific dyes such as MitoTracker-RED, Rhodamine123 and Janus Green B positively stained the luterials, but not exosomes. A well-known mitochondrion-specific marker anti-VDAC showed a positive binding to the luterials, but not to exosomes. Platelet mitochondria was used as a positive control, which exhibited the positive staining with anti-VDAC. Also, fluorescent staining against an ATP-related protein CD39 which was confirmed to be present in luterials by the Western blot.

The DNA extracts of luterials were further subjected to qRT-PCR using seven known probes for ATP-related proteins, ND1 (OXPHOS complex I), CO1 (OXPHOS complex IV), ATP6 (OXPHOS complex V), ATP8 (OXPHOS complex V), RNR1, RNR2 and 7S. The luterials expressed transcripts for all seven genes comparable to those expressed in mitochondria isolated from MRC-5 lung fibroblast cell lines.

The whole genome sequencing for mtDNA of the platelets and DNA of luterials obtained from two other donors was performed using Next Generation Sequencing followed by BLAST search against NCBI mitochondria database. DNA sequence from platelet mitochondria and luterials shared >99% homology, yet with the base variation evident in both donors between cellular mitochondria and luterials. A common point variation in 16 bases of the luterials in comparison to rCRS among all three donors of the capillary and whole genome sequencing experiments. Those common point variations in 16 bases may be the potential markers for the luterials. Luterial specific point variations compared to those of mitochondria are in positions of 150, 183, 309, 4793, 4833, 5108, 7867, 8200, 8701, 11914, 14569, 15323, 15497, 15860, 16325 and 16519 of sequence as set forth in SEQ ID NO:24 (FIG. 28). Luterial specific point variations at 16 positions might be described as follows:

T in position 150,
G in position 183,
CC or CCC in position 309,
G in position 4793,
G in position 4833,
CC or CCC in position 5108,
T in position 7867,
C in position 8200,
G in position 8701,
A in position 11914,
A in position 14569,
A in position 15323,
A in position 15497,
G in position 15860,
C in position 16325, and
C in position 16519 of sequence as set forth in SEQ ID NO:24.

| Position | Point Variations | |
|---|---|---|
| | Mitochondria | Luterial |
| 150 | C | T |
| 183 | A | G |
| 309 | C | CC, CCC |
| 4793 | A | G |
| 4833 | A | G |
| 5108 | T | CC, CCC |
| 7867 | C | T |
| 8200 | T | C |
| 8701 | A | G |
| 11914 | G | A |
| 14569 | G | A |
| 15323 | G | A |
| 15497 | G | A |
| 15860 | A | G |
| 16325 | T | C |
| 16519 | T | C |

Figure 22:
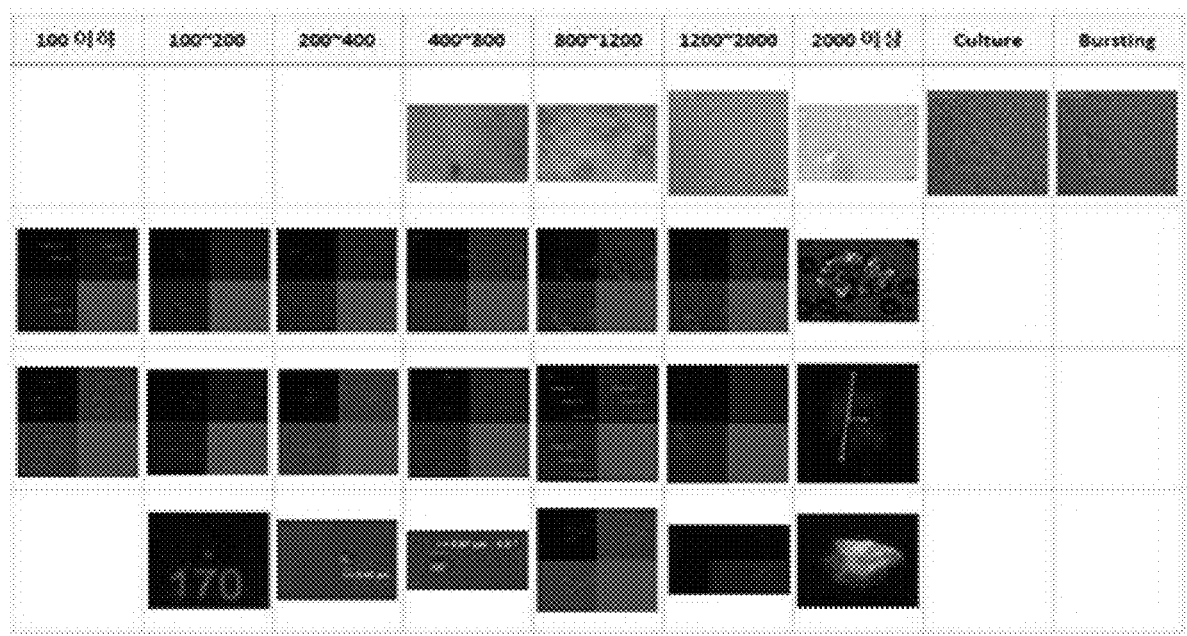
FIG. 22 depicts confocal laser scanning microscope images showing the change in size of luterial caused by culture.

Example 8: Culture of Luterials (1) Among luterials obtained in Example 2, luterials having a size of about 20-200 nm were irradiated with IR light after addition of PBS, and then cultured at 18 to 30° C. for about 3 hours. At about 1-hour intervals immediately after irradiation with IR light, the size of the luterials was measured with a microscope. After about 1-6 hours, luterials having a size of about 200 nm before culture grew to a size of about 500 nm. Thus, when water was added to blood-derived luterials which were then cultured at 18 to 30° C. under irradiation with IR light, the luterials could grow to a size of about 500 nm. Consistently, when luterials were additionally cultured, they grew to a size of several hundreds of μm and did also burst during the additional culture (FIG. 22).

(2) Among luterials obtained in Example 2, luterials having a size of about 400-800 nm were irradiated with IR light after addition of PBS, and then cultured at 18 to 30° C. for about 3 hours. At about 1-hour intervals immediately after irradiation with IR light, the size and status of luterials were measured with a microscope. After about 1-6 hours, it was shown that luterials having a size of about 400-800 nm before culture underwent fission without growth.

Figure 23:
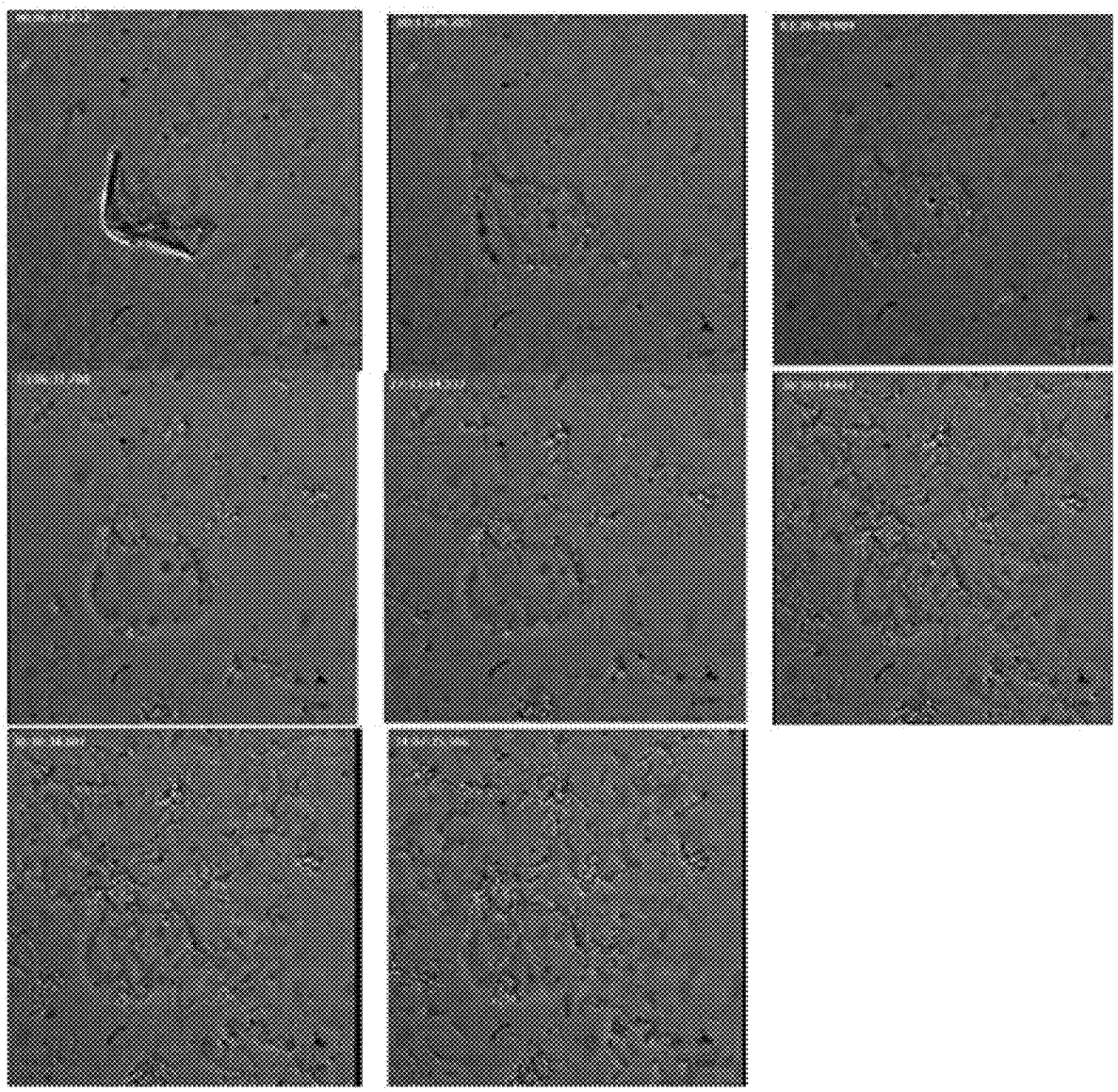
FIG. 23 depicts images showing the change in morphology and size of luterial caused by culture.

In addition, it was observed that, when mutant luterials having a size of 800 nm or more were further cultured, they changed to mutant luterials that are seen in the blood of cancer patients (FIG. 23).

Example 9: Anticancer Effect of Luterials

In order to measure inhibitory effects of luterials on the growth of two ovarian cell lines (SKOV3 and A2780), a yellow tetrazolium MTT (3-(4,5-dimethylthiazolyl-2)-2,5-diphenyltetrazolium bromide) assay was performed. The MTT assay is a method for measuring the growth of living cells, and is based on the principle that dehydrogenase in mitochondria of living cells produces violet formazan when the yellow water-soluble substance MTT is added. The production of violet formazan is known to be substantially proportional to the number of living cells having metabolic activity, and thus can be very effective in measuring the growth and differentiation of cells.

Specifically, 100 μl of cultured cancer cells were added to a 96-well plate at a concentration of $5 \times 10^4$ cells/ml and cultured in a humidified incubator (5% carbon and 95% oxygen) at 37° C. for 24 hours, and then treated with various concentrations of luterials having a size of 100-800 nm. After 48 hours of culture, 15 μl of a solution of MTT (5 mg/ml) in phosphate buffered saline (PBS) was added to each well, followed by culture for 4 hours. After the formation of formazan was confirmed, the medium was completely removed, and 100 μl of dimethyl sulfoxide (DMSO) was added to each well in order to dissolve formazan formed at the well bottom. Thereafter, the absorbance at 560 nm was measured using a microplate reader (GEMINI, Stratec Biomedical), and the inhibition rate of cell growth by luterials relative to 100% of the control cells was calculated.

Figure 27:
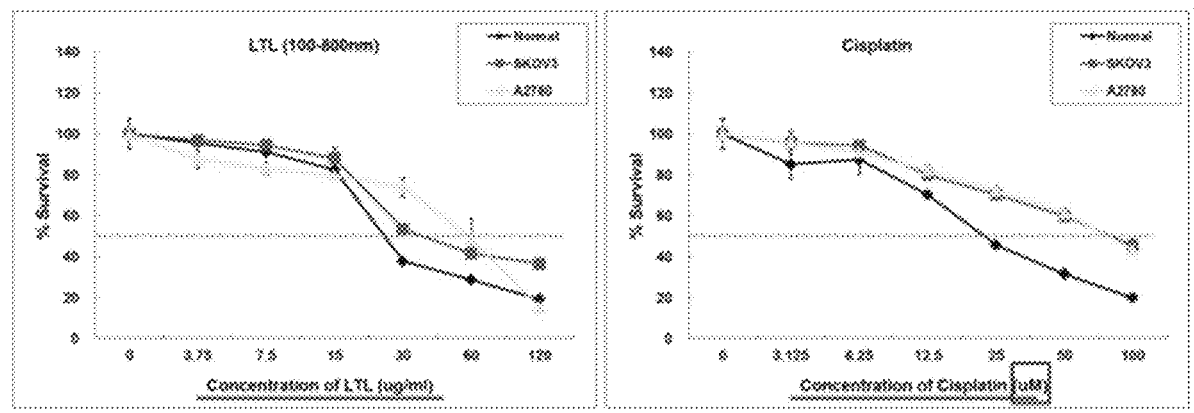
FIG. 27 shows cell viability measured by an MTT assay after treating ovarian cancer cell lines (SKOV3 and A2780) with varying concentrations of luterials having a size of 100-800 nm and the commercially available anticancer drug cisplatin.

As a result, the $IC_{50}$ values of luterials for the SKOV3 and A2780 cell lines were 30 μg/ml and 60 μg/ml, respectively. The $IC_{50}$ value of the commercially available anticancer drug cisplatin was 100 μM (FIG. 27). Luterials showed stronger cytotoxicity than the positive control drug for the two ovarian cancer cell lines, and showed cytotoxicity similar to that of the positive control drug for normal ovarian cells.

INDUSTRIAL APPLICABILITY

As described above, according to the present invention, the unidentified nano-sized particle luterial present in the body fluid of patients or normal persons can be effectively isolated, and the isolated luterial can be cultured so as to grow to a certain size. As such, luterial is useful for the diagnosis and treatment of disease. In addition, luterial shows a strong anticancer effect against cancer cell lines, and thus is useful as an anticancer agent.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for isolating luterial from body fluid, comprising:

(A) conducting at least one of the following with a body fluid:
  (i) obtaining the body fluid by collecting a supernatant after centrifuging of the body fluid to remove platelet and blood-derived substances having a size greater than that of platelet;
  (ii) filtering the body fluid with filters of various pore sizes to select for particles within a specific size range;
  (iii) centrifuging the body fluid at 100,000 g-200,000 g to collect the supernatant;

(B) conducting at least one of the following with a solution obtained from (A):
  (i) irradiating the solution with visible light to select for autofluorescent and mobile particles; or
  (ii) subjecting the solution to a density gradient fractionation to further separate the particles in the solution; and (C) recovering luterial from fluids obtained from conducting (A) and (B) by isolating a particle having one or more of the following characteristics:

(a) a positive staining reaction with Janus green B, Acridine Orange, DAPI, or Rhodamine 123 in a fluorescence test;
(b) in healthy condition expressing beta-proteobacteria-derived and gamma-proteobacteria-derived genes and having a size of less than 800 nm;
(c) in a diseased condition, expressing not only beta-proteobacteria or gamma-proteobacteria-derived genes, but also eukaryote Streptophyta genes and having a size of greater than 800 nm;
(d) exhibiting ATP production in normal conditions;
(e) a cell or cell-like structure completely different from mitochondria or exosomes;
(f) circular or oval in shape in a healthy condition, and non-uniform in morphology in a diseased condition;
(g) containing a membrane structure and is adherent;
(h) presence inside or outside cells;
(i) exhibiting mobility and undergoing fusion and/or fission events;
(j) mutant luterial bursting in a certain condition and having stemness after bursting;
(k) a function of regulating p53 gene and telomeres;
(l) expressing at least one protein selected from the group consisting of CD14, CD24, CD29, CD34, CD39, CD44, CD45 (CD45RA/CD45RO), CD73, CD90, CD105, CD133, CD173, CD326, CD332, OCT4, ND1 (OXPHOS complex I), CO1 (OXPHOS complex IV), ATP6 (OXPHOS complex V), ATP8 (OXPHOS complex V), RNR1, RNR2 and 7S; and
(m) presence in a fraction with 0.99 g/ml or less density in 15-60% sucrose density gradient.

2. The method of claim 1, wherein the luterial is present in blood (plasma, serum, Red blood cells, white blood cells, platelets, etc.) derived from mammals (including humans), saliva, lymphatic duct, breast milk (in particular, colostrum), umbilical cord blood, brain cells, spinal cord, bone marrow, majority of cells including hematopoietic cells, stem cells, reproductive cells (eggs, sperm, semen, vaginal fluid, etc.), in horns in case of animals with horns, and fluid from plants.

3. The method of claim 1, wherein the luterial comprises a polynucleotide sequence having at least 99% sequence identity to polynucleotide sequence of SEQ ID NO: 24 (sequence of human mitochondria genome map) or a complementary polynucleotide sequence thereto.

4. The method of claim 1, wherein the luterial comprises point variations to alleles tabulated below in one or more positions selected from the group consisting of 150, 183, 309, 4793, 4833, 5108, 7867, 8200, 8701, 11914, 14569, 15323, 15497, 15860, 16325 and 16519 of sequence as set forth in SEQ ID NO:24:

|  | Point Variations | |
| --- | --- | --- |
| Position | Mitochondria | Luterial |
| 150 | C | T |
| 183 | A | G |
| 309 | C | CC, CCC |
| 4793 | A | G |
| 4833 | A | G |
| 5108 | T | CC, CCC |
| 7867 | C | T |
| 8200 | T | C |
| 8701 | A | G |
| 11914 | G | A |
| 14569 | G | A |
| 15323 | G | A |
| 15497 | G | A |
| 15860 | A | G |
| 16325 | T | C |
| 16519 | T | C |

5. The method of claim 1, wherein luterial is classified according to size into 20-200 nm, 200-400 nm, 400-600 nm, 600-800 nm, and 800-1,000 nm by the sequential use of 200 nm, 400 nm, 600 nm, 800 nm, and 1000 nm sized filters.

6. The method of claim 1, wherein the step (A)(i) is performed by centrifuging the blood at 1,200-5,000 rpm for 5-10 minutes repeatedly.

7. The method of claim 6, wherein the step (A)(i) is performed at 100,000 g or more for 0.5 min to 24 hrs.

8. The method of claim 6, wherein luterial has a density of 0.9 to 0.99 g/ml in a sucrose density gradient of 5-70%.

9. The method of claim 1, wherein the step (A)(iii) separates out general microparticles including exosomes from luterials.

10. The method of claim 1, wherein step (B)(ii) isolates luterial by the steps comprising:
(a) laying the solution on top of sucrose gradient with tiers of 5-70% of sucrose concentration; and
(b) centrifuging the body fluid laid on top of the sucrose gradient in the step (a).

* * * * *

UNITED STATES PATENT AND TRADEMARK OFFICE
CERTIFICATE OF CORRECTION

PATENT NO. : 10,590,384 B2
APPLICATION NO. : 15/633283
DATED : March 17, 2020
INVENTOR(S) : Won Cheol Choi Page 1 of 1

It is certified that error appears in the above-identified patent and that said Letters Patent is hereby corrected as shown below:

In the Specification

Column 3, Line 20: "sternness" should be -- stemness --.

Column 12, Line 26: "sternness" should be -- stemness --.

Column 19, Line 3: "sternness" should be -- stemness --.

Signed and Sealed this
Twelfth Day of May, 2020

Andrei Iancu
*Director of the United States Patent and Trademark Office*